US012280998B2

(12) United States Patent
Gette et al.

(10) Patent No.: US 12,280,998 B2
(45) Date of Patent: Apr. 22, 2025

(54) APPARATUS AND METHOD FOR TREATING AND IN PARTICULAR STERILISING CONTAINERS

(71) Applicant: KRONES AG, Neutraubling (DE)

(72) Inventors: Viktor Gette, Wörth an der Donau (DE); Konrad Senn, Alteglofsheim (DE); Andreas Pense, Obertraubling (DE); Florian Fuchs, Regensburg (DE); Alexander Feigl, Mintraching (DE); Wolfgang Schoenberger, Brennberg (DE); Andreas Eichenseher, Regensburg (DE); Florian Hoffmann, Burglengenfeld (DE); Josef Knott, Schierling (DE); Andreas Vornehm, Offenberg (DE); Michael Neubauer, Grassau (DE); Stefan Kornprobst, Dietfurt a.d. Altmühl (DE)

(73) Assignee: KRONES AG, Neutraubling (DE)

( * ) Notice: Subject to any disclaimer, the term of this patent is extended or adjusted under 35 U.S.C. 154(b) by 0 days.

(21) Appl. No.: 18/088,171

(22) Filed: Dec. 23, 2022

(65) Prior Publication Data
US 2023/0202820 A1 Jun. 29, 2023

(30) Foreign Application Priority Data
Dec. 23, 2021 (DE) ...................... 10 2021 134 499.9

(51) Int. Cl.
B67C 3/24 (2006.01)
B67C 3/26 (2006.01)
(52) U.S. Cl.
CPC ............ B67C 3/242 (2013.01); B67C 3/2642 (2013.01)

(58) Field of Classification Search
CPC ..... B67C 3/242; B67C 3/2642; B67C 7/0053; B29C 49/36; B29C 49/42065;
(Continued)

(56) References Cited

U.S. PATENT DOCUMENTS 4,511,027 A    4/1985  Zamboni ........................ 198/478
5,046,599 A *  9/1991  Hamano ............... B67C 7/0046
                                                   198/481.1
(Continued)

FOREIGN PATENT DOCUMENTS

DE    102008012836    9/2009    ............. C23C 14/56
DE    102010018216    10/2011   ............. B65G 47/52
(Continued)

OTHER PUBLICATIONS

German Search Report, with machine translation, issued in German Application No. 10 2021 134 499.9, dated Sep. 9, 2022, 10 pgs.
(Continued)

Primary Examiner — Hemant Desai
Assistant Examiner — Mobeen Ahmed
(74) Attorney, Agent, or Firm — HAYES SOLOWAY P.C.

(57) ABSTRACT

Disclosed is a container treatment apparatus and treatment method, in particular a container sterilisation apparatus, having a plurality of transport devices for transporting a container along a predetermined transport path, at least one of the transport devices having at least one holding device for holding at least one container during container treatment and/or transport along the transport path, the transport device having a rotatable carrier and a plurality of holding elements arranged on this carrier, wherein a holding element in a first sector, in which a container is received, having a height with respect to a perpendicular projection of the transport path which is different from that in a second sector in which a container is dispensed, and wherein a sector in
(Continued)

which an at least partial compensation of the height difference of the holding elements takes place lies along a direction of rotation of the carrier after the second sector and before the first sector.

11 Claims, 18 Drawing Sheets

(58) Field of Classification Search
CPC ........ B29C 49/42073; B29C 49/42095; B29C 49/42418; B29C 49/42822; B29C 2949/0715; B65B 55/04; A61L 2/087; A61L 2/00; A61L 2202/23
See application file for complete search history.

(56) References Cited

U.S. PATENT DOCUMENTS

| | | | |
|---|---|---|---|
| 5,538,054 A | 7/1996 | Luhmann | G01F 23/292 |
| 6,354,427 B1 | 3/2002 | Pickel et al. | 198/470.1 |
| 7,739,859 B2* | 6/2010 | Colato | B67B 3/06 |
| | | | 53/167 |
| 8,240,459 B2 | 8/2012 | Bernhard | B65G 47/846 |
| 8,294,126 B2* | 10/2012 | Humele | H01J 33/00 |
| | | | 53/426 |
| 8,729,499 B2* | 5/2014 | Knott | B65B 55/08 |
| | | | 250/455.11 |
| 8,813,945 B2 | 8/2014 | Jogsch et al. | B65G 47/244 |
| 8,871,135 B2 | 10/2014 | Hausladen et al. | B29C 49/24 |
| 9,039,405 B2 | 5/2015 | Zacche et al. | B29C 49/68 |
| 9,181,043 B1* | 11/2015 | Goudy | B65G 29/00 |
| 9,233,800 B2 | 1/2016 | Senn et al. | B65G 47/082 |
| 9,343,190 B2 | 5/2016 | Scheuren et al. | |
| 9,434,498 B2 | 9/2016 | Schmid et al. | |
| 9,499,353 B2* | 11/2016 | Fahldieck | B67B 3/02 |
| 9,522,755 B2 | 12/2016 | Scheuren et al. | |
| 9,624,039 B2* | 4/2017 | Clüsserath | B67C 3/242 |
| 9,630,035 B2 | 4/2017 | Muehlstein et al. | A62C 2/22 |
| 9,908,651 B2 | 3/2018 | Ehmer et al. | |
| 10,077,179 B2 | 9/2018 | Linke et al. | |
| 10,196,253 B2* | 2/2019 | Clüsserath | B67C 7/0046 |
| 10,272,668 B2 | 4/2019 | Endou et al. | B41F 17/18 |
| 10,285,217 B2* | 5/2019 | Schoenberger | B29C 49/4205 |
| 10,519,018 B2 | 12/2019 | Zoni et al. | B67C 7/0053 |
| 11,027,956 B2 | 6/2021 | Hayakawa | |
| 11,365,067 B2 | 6/2022 | Meunier et al. | B65G 47/847 |
| 12,138,760 B2 | 11/2024 | Ehrismann et al. | B25B 5/04 |
| 2007/0289665 A1* | 12/2007 | Mazzon | B67C 7/0046 |
| | | | 141/165 |
| 2009/0045350 A1* | 2/2009 | Humele | H01J 33/00 |
| | | | 250/455.11 |
| 2010/0270477 A1 | 10/2010 | Nishino et al. | 250/455.11 |
| 2010/0282364 A1 | 11/2010 | Balzarin | 141/165 |
| 2010/0300577 A1 | 12/2010 | Wagner | B65B 3/04 |
| 2010/0326563 A1* | 12/2010 | Kobayashi | H05F 3/06 |
| | | | 141/11 |
| 2011/0012032 A1* | 1/2011 | Bufano | A61L 2/087 |
| | | | 250/492.3 |
| 2011/0016829 A1* | 1/2011 | Drenguis | B65B 55/08 |
| | | | 53/167 |
| 2013/0129566 A1 | 5/2013 | Knott et al. | A61L 2/087 |
| 2013/0202481 A1* | 8/2013 | Kobayashi | A01N 1/0294 |
| | | | 422/22 |
| 2013/0330437 A1 | 12/2013 | Zacche et al. | B65G 47/30 |
| 2014/0112826 A1 | 4/2014 | Knott et al. | 422/22 |
| 2014/0166436 A1 | 6/2014 | Blochmann | 198/379 |
| 2014/0216661 A1* | 8/2014 | Sugimoto | B65C 3/08 |
| | | | 156/443 |
| 2014/0299786 A1* | 10/2014 | Yokobayashi | B65G 47/847 |
| | | | 250/455.11 |
| 2014/0369885 A1* | 12/2014 | Krueger | B65B 65/003 |
| | | | 250/393 |
| 2015/0048074 A1 | 2/2015 | Schoenberger | H05B 1/023 |
| 2015/0069271 A1* | 3/2015 | Soellner | B65G 29/00 |
| | | | 250/492.3 |
| 2015/0069670 A1 | 3/2015 | Hoellriegl et al. | B29C 49/4205 |
| 2015/0071818 A1 | 3/2015 | Scheuren et al. | B65B 55/16 |
| 2015/0238643 A1* | 8/2015 | Knott | B65B 55/08 |
| | | | 250/454.11 |
| 2016/0083131 A1* | 3/2016 | Yokobayashi | A61L 2/26 |
| | | | 250/454.11 |
| 2016/0194157 A1 | 7/2016 | Senn et al. | B65G 35/00 |
| 2016/0376099 A1 | 12/2016 | Wagner et al. | B65D 90/22 |
| 2017/0043991 A1 | 2/2017 | Seewald-Raider | B67C 54/02 |
| 2017/0197401 A1 | 7/2017 | Endou | B41F 17/18 |
| 2019/0071259 A1* | 3/2019 | Bauer | B65C 9/02 |
| 2021/0094769 A1 | 4/2021 | Kammerl et al. | B65G 54/02 |
| 2022/0008573 A1* | 1/2022 | Bernard | A61L 2/087 |
| 2022/0153565 A1 | 5/2022 | Bauer et al. | B67C 3/24 |
| 2022/0176610 A1 | 6/2022 | Suppes et al. | B29C 49/46 |
| 2022/0234876 A1 | 7/2022 | Raith et al. | B67C 7/0013 |
| 2023/0167850 A1 | 6/2023 | Echtenacher et al. | F16C 19/16 |
| 2023/0249857 A1* | 8/2023 | Ribi | B65B 65/003 |
| | | | 53/48.1 |
| 2024/0076089 A1 | 3/2024 | Mayer | B65C 9/06 |

FOREIGN PATENT DOCUMENTS

| | | | | |
|---|---|---|---|---|
| DE | 102011055552 | 5/2013 | ............ | B65B 55/08 |
| DE | 102011056628 | 6/2013 | ............ | A61L 2/08 |
| DE | 102012005926 | 9/2013 | ............ | B65B 61/02 |
| DE | 102012110108 | 4/2014 | ............ | A61L 2/08 |
| DE | 102012221719 | 5/2014 | ............ | B65G 47/84 |
| DE | 102013109794 | 3/2015 | ............ | A61L 2/08 |
| DE | 102013109988 | 3/2015 | ............ | A61L 2/08 |
| DE | 102014116478 | 5/2016 | ............ | B67C 3/22 |
| DE | 102015209367 | 11/2016 | ............ | B65C 9/02 |
| DE | 102017118482 | 2/2019 | ............ | B29C 49/42 |
| DE | 102019134836 | 6/2021 | ............ | B65B 3/02 |
| DE | 102008011774 | 12/2021 | ............ | C23C 16/54 |
| DE | 102020130535 | 5/2022 | ............ | B67C 3/24 |
| EP | 2100717 | 9/2009 | ............ | B29C 49/64 |
| EP | 2269943 | 1/2011 | ............ | B67C 7/00 |
| EP | 2347884 | 7/2011 | ............ | B29C 49/24 |
| EP | 2724731 | 4/2014 | ............ | A61L 2/08 |
| EP | 2769922 | 8/2014 | ............ | B65B 55/08 |
| EP | 2837487 | 2/2015 | ............ | B29C 49/42 |
| EP | 2845610 | 3/2015 | ............ | A61L 2/08 |
| EP | 2848263 | 3/2015 | ............ | A61L 2/08 |
| EP | 2913066 | 9/2015 | ............ | A61L 2/08 |
| EP | 3431402 | 1/2019 | ............ | B65B 55/04 |
| EP | 3798193 | 3/2021 | ............ | C03C 17/00 |
| EP | 3919419 | 12/2021 | ............ | B25B 5/04 |
| EP | 4001209 | 5/2022 | ............ | B67C 7/00 |
| EP | 4008364 | 6/2022 | ............ | A61L 2/18 |
| EP | 4063313 | 9/2022 | ............ | B67C 7/00 |
| JP | 58100010 | 6/1983 | ............ | B65G 29/47 |
| JP | 20066726 | 1/2006 | ............ | A61L 2/08 |
| JP | 201386822 | 5/2013 | ............ | B65B 55/08 |
| JP | 2013126893 | 6/2013 | ............ | B65B 55/06 |
| JP | 2014129139 | 7/2014 | ............ | B65B 55/04 |
| JP | 2015140199 | 8/2015 | ............ | B65C 9/42 |
| WO | 2005108278 | 11/2005 | ............ | A61L 2/08 |
| WO | WO2006136187 | 12/2006 | ............ | C23C 14/56 |
| WO | 2009095182 | 8/2009 | ............ | A61L 2/08 |
| WO | WO 2013092735 | 6/2013 | ............ | A61L 2/08 |
| WO | WO2014185251 | 11/2014 | ............ | B65B 55/88 |
| WO | 2015036194 | 3/2015 | ............ | B65G 54/02 |
| WO | WO 2016173720 | 11/2016 | ............ | B57C 7/00 |
| WO | 2018138374 | 8/2018 | ............ | A61L 2/08 |
| WO | WO2019034628 | 2/2019 | ............ | B29C 49/42 |
| WO | 2019121723 | 6/2019 | ............ | B65G 47/64 |
| WO | WO2020001987 | 1/2020 | ............ | B65C 9/04 |
| WO | 2020094948 | 5/2020 | ............ | A61L 2/08 |
| WO | 2020126139 | 6/2020 | ............ | B67C 7/00 |
| WO | 2021113987 | 6/2021 | ............ | B65G 47/24 |

OTHER PUBLICATIONS

German Search Report, with machine translation, issued in German Application No. 10 2021 134 504.9, dated Sep. 13, 2022, 12 pgs.

(56) References Cited

OTHER PUBLICATIONS

German Search Report, with machine translation, issued in German Application No. 10 2021 134 507.3, dated Jul. 7, 2022, 11 pgs.
German Search Report, with machine translation, issued in German Application No. 10 2021 134 514.6, dated Sep. 14, 2022, 12 pgs.
German Search Report, with machine translation, issued in German Application No. 10 2021 134 529.4, dated Sep. 13, 2022, 10 pgs.
European Search Report, with machine translation, issued in European Application No. 22214159.0, dated May 19, 2023, 29 pgs.
European Search Report, with machine translation, issued in European Application No. 22214312.5, dated May 30, 2023, 17 pgs.
Extended European Search Report issued in EP Patent Appln. Serial No. 22214333.1-1101, dated Jun. 14, 2023, with machine English translation, 12 pages.
Extended European Search Report issued in EP Patent Appln. Serial No. 22214356.2-1101, dated Jun. 20, 2023, with machine English translation, 27 pages.
Notice of Reason for Refusal issued in Japanese Patent Appln. Serial No. 2022-201012, dated Mar. 4, 2024, with machine English translation, 8 pages.
Extended European Search Report issued in EP Patent Appln. Serial No. 22214121.0, dated Oct. 6, 2023, with machine English translation, 21 pages.
Office Action issued in U.S. Appl. No. 18/088,179, dated Oct. 5, 2023, 23 pages.
Office Action issued in Japanese Patent Appln. Serial No. 2022-201006, dated Nov. 14, 2023, with English translation, 15 pages.
European Search Report issued in EP Patent Appln. Serial No. 22214356.2, dated Nov. 30, 2023, with machine English translation, 28 pages.
Extended European Search Report issued in EP Patent Appln. Serial No. 22214159.0, dated Oct. 24, 2023, with machine English translation, 24 pages.
Notice of Rejection issued in Japanese Patent Appln. Serial No. 2022-200999, dated Nov. 14, 2023, with machine English translation, 22 pages.
Notice of Rejection issued in Japanese Patent Appln. No. 2022-201006, dated Apr. 30, 2024, with English translation, 14 pages.
Office Action issued in U.S. Appl. No. 18/088,179, dated Jul. 18, 2024, 11 pages.
Office Action issued in U.S. Appl. No. 18/088,188, dated Jul. 3, 2024, 14 pages.
Office Action issued in U.S. Appl. No. 18/088,161, dated Jul. 18, 2024, 11 pages.
U.S. Appl. No. 18/088,161, filed Dec. 23, 2022, Neubauer et al.
U.S. Appl. No. 18/088,179, filed Dec. 23, 2022, Neubauer et al.
U.S. Appl. No. 18/088,188, filed Dec. 23, 2022, Neubauer et al.
U.S. Appl. No. 18/088,235, filed Dec. 23, 2022, Kornprobst.
Office Action issued in U.S. Appl. No. 18/088,188, dated Dec. 5, 2024, 14 pages.
Office Action issued in U.S. Appl. No. 18/088,235, dated Oct. 15, 2024, 8 pages.

\* cited by examiner

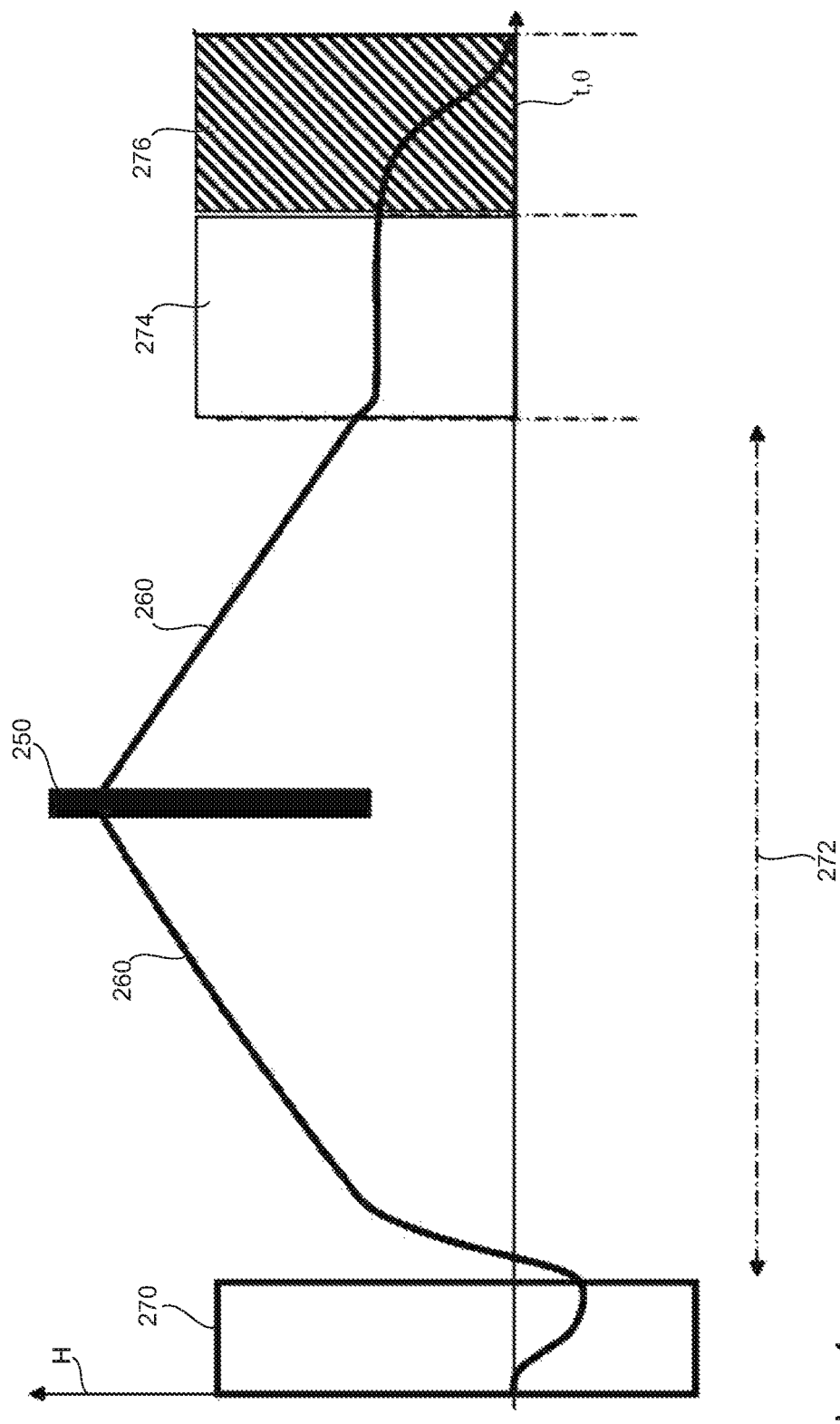

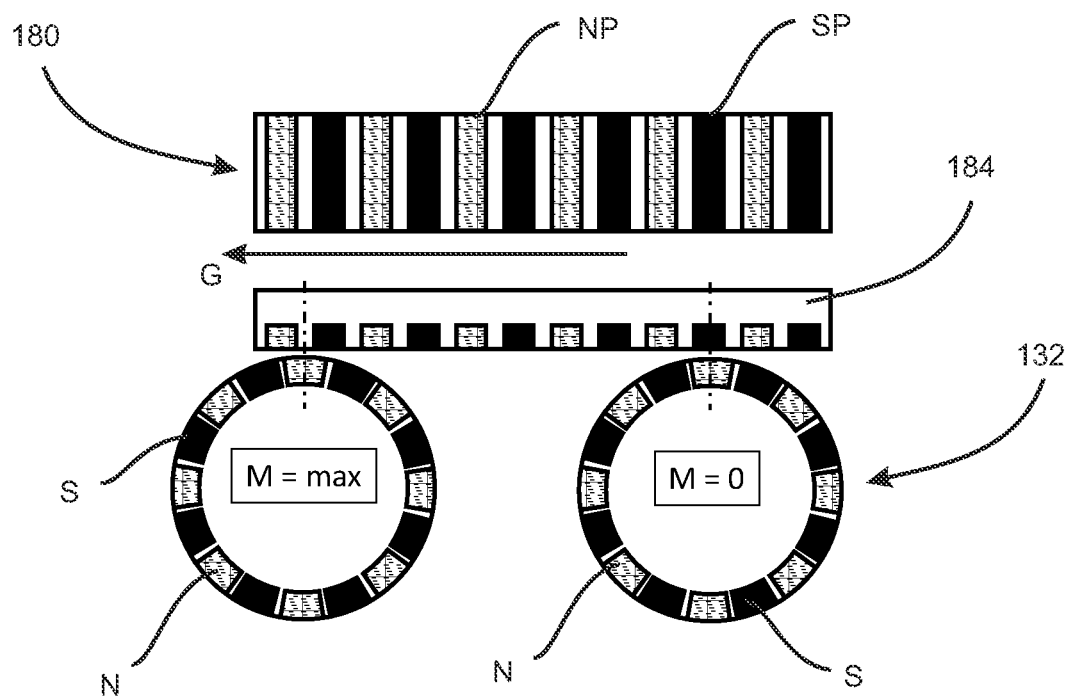
Fig. 17
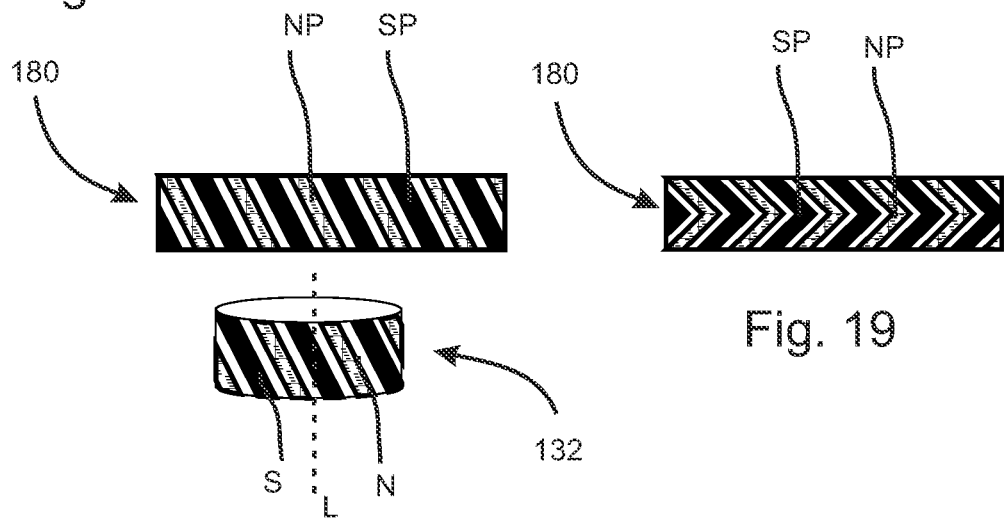
Fig. 18
Fig. 19
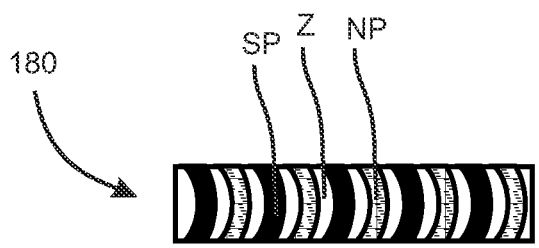
Fig. 20

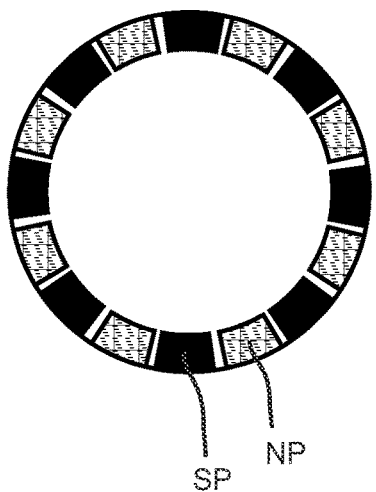
Fig. 21
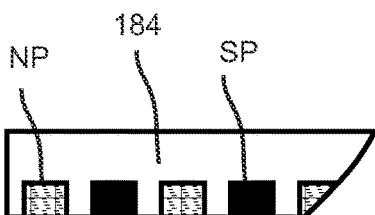
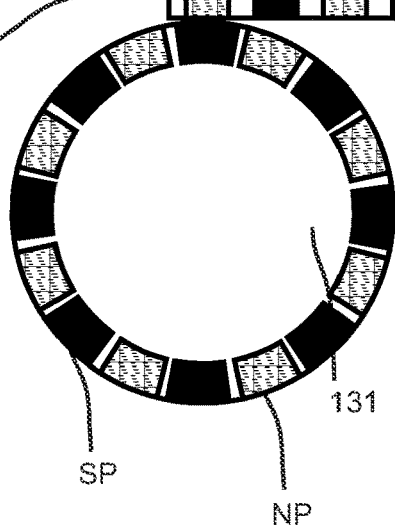
Fig. 22
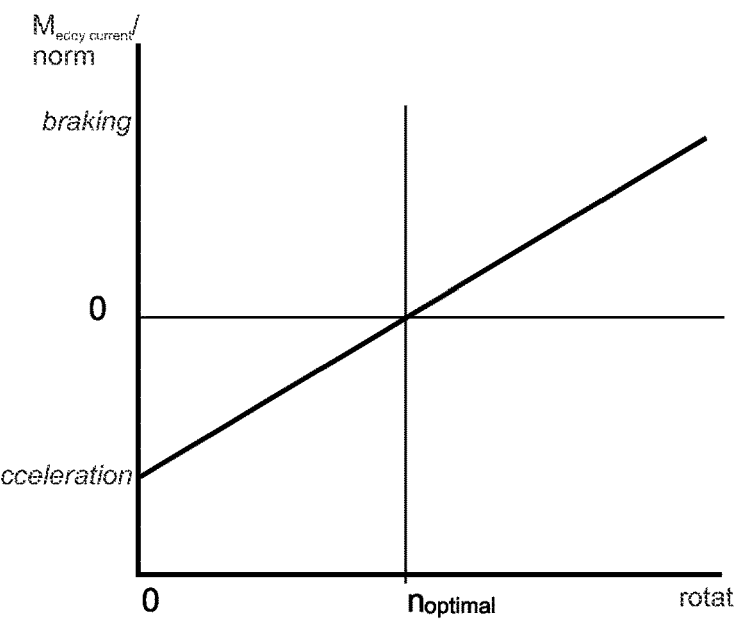
Fig. 23

APPARATUS AND METHOD FOR TREATING AND IN PARTICULAR STERILISING CONTAINERS

BACKGROUND OF THE INVENTION

The present invention relates to a container treatment apparatus, in particular a container sterilisation apparatus, having several transport devices for transporting a container along a predetermined transport path within a housing, wherein at least one of the transport devices is a container outer surface treatment device and at least one of the transport devices is a container inner surface treatment device, which each have at least one holding device for holding at least one container during container treatment and/or transport along the transport path. Furthermore, the invention relates to a method for treating containers, in particular for sterilising containers.

Various container treatment apparatus are known from the prior art. Often, preforms are treated in such a container treatment apparatus, which are formed for example into bottles or other containers in a subsequent step. This has the advantage that a comparatively small area has to be treated. This is particularly advantageous in sterilisation processes, as a smaller area has to be sterilised and sterilising agents and/or energy can be saved.

The sterilisation of containers is usually carried out in an at least largely closed housing in order to avoid contamination from the outside. In some systems, at least one sterilisation process includes an application with radiation. A radiation source provided for this purpose is also usually arranged at least in sections in a housing and emits the radiation into the interior of the housing, wherein the housing having shielding properties for this radiation. In this way, persons in the vicinity of such a sterilisation device can be protected from scattered radiation.

Especially when sterilising different areas of containers one after the other, the problem arises that all these devices should be arranged within the housing in order to avoid intermediate contamination of the already sterilised surfaces. If several such sterilisation units are arranged within a common housing, they form a so-called sterilisation module. Due to the many sterilisation units and the transport devices for transferring individual containers from one sterilisation unit to the next, this is often very voluminous and requires a large footprint.

It is known from the applicant's internal prior art to sterilise the outer and inner surfaces of plastic preforms after heating in an oven. The sterilisation of a container to be filled is, in addition to the actual filling process, the central process step in an aseptic filling line. Newer developments use ionising radiation to achieve a reduction in germs. In most applications, this radiation consists of accelerated electrons which are generated in a corresponding system and treat the containers to be sterilised, wherein systems used for sterilisation consist of an electron-generating device and a beam finger for sterilising the inner surfaces and an electron-generating device and a surface radiator for sterilising outer surfaces. The treatment devices for sterilising the outer surfaces and the sterilisation of the inner surfaces are each arranged on a carousel or transport starwheel, which are connected to a pitch distribution starwheel.

The X-ray radiation generated during sterilisation must be shielded from the environment by suitable shielding, so that the two treatment devices are embedded or enclosed in a radiation-shielding device. Such a shielding device is described in more detail in EP 2 845 610 A1, for example.

The embodiments described therein each also represent preferred embodiments of the housing of the present invention. The applicant expressly reserves the right to use features of this publication also to define preferred embodiments of the present invention. In order to ensure radiation shielding also at the inlet and outlet windows to the enclosed apparatus, an inlet star is connected upstream and an outlet star is connected downstream in each case. This results in an overall apparatus which is equipped with five stars or carousels.

However, this results in a very long transfer or a very long transport distance from the oven to the blow moulding machine or a long dwell time of the containers in the treatment module. This results in great difficulties when moulding plastic preforms into finished plastic containers, as the preforms cool down too much on the transport path. In addition, the frequent transfers within a poorly accessible radiation-shielding housing increase the risk of faulty transfers, especially during the transition from the infeed starwheel to the outer treatment module, since a punctual transfer from a holding clamp to a holding mandrel takes place here. Mistakes such as misalignment or similar can then lead to the loss of the preform or even damage to the transfer devices during the subsequent transfers. With higher outputs, the footprint of the system also increases, as this increases per existing star or carousel.

Therefore, there is a need to provide a container treatment apparatus, in particular a container sterilisation device, which can be realised in a more compact way and still offers a high throughput of containers. Such a container treatment apparatus should be as modular as possible and be compatible with other upstream or downstream container treatment apparatus such as a blow moulding device or a heating device. Furthermore, there is a need for a method for effective container treatment on a short transport path.

SUMMARY OF THE INVENTION

A solution to the underlying problem according to the invention is thus solved by a container treatment apparatus, in particular a container sterilisation device, having several transport devices for transporting a container along a predetermined transport path within a housing, wherein at least one of the transport devices is a container outer surface treatment device and at least one of the transport devices is a container inner surface treatment device. Both the container outer surface treatment device and the container inner surface treatment device each have at least one holding device for holding at least one container during container treatment and/or transport along the transport path.

It is essential for a first solution of the problem that a holding device of the container outer surface treatment device and/or of the container inner surface treatment device can be brought at least temporarily into the region of an opening of a housing wall in order to receive a container to be brought into the space surrounded by the housing or to discharge a container to be led out of the space surrounded by the housing. The possibility of being able to bring a holding device of the container outer surface treatment device and/or the container inner surface treatment device at least temporarily into the region of an opening of a housing wall in such a container treatment apparatus makes it possible to transfer the container directly to a container treatment device or to receive it from such a container treatment device. This makes it possible to dispense with a transport device which transfers the inserted container to the first container treatment device following along the transport path inside the housing and/or takes over the treated container from the last container treatment device inside the housing and discharges it from the housing.

Preferably, a holding device of the container outer surface treatment device and/or of the container inner surface treatment device is relatively movable with respect to a container treatment device. In addition or alternatively, in a particularly preferred embodiment, a position and/or orientation of a container in the area of the container outer surface treatment device and/or the container inner surface treatment device can be changed with respect to a vertical projection of the transport path. This movement of containers relative to each other or relative to the projection of the transport path enables, for example, the introduction of a beam finger or a nozzle into the interior of the container for container inner surface treatment. Likewise, for some applications, a relative movement in the area of the container outer surface treatment device can also be advantageous, for example to rotate and/or tilt a container relative to a nozzle or radiation source, in order to also make previously shaded surface areas accessible for the container outer surface treatment device.

In a preferred embodiment, the container outer surface treatment device and/or the container inner surface treatment device each have a rotatable carrier. Such rotatable carriers are often used in particular in the field of bottle handling, so that this embodiment offers a particularly good possibility of integrating the container treatment apparatus into existing systems or systems to be newly equipped. Preferably, the rotational axes of the container outer surface treatment device and the container inner surface treatment device run essentially parallel, in particular preferably exactly parallel. This design makes it possible to achieve particularly smooth running of the carriers in relation to each other.

Preferably, the container outer surface treatment device and/or the container inner surface treatment device has a plurality of holding elements. This makes it possible to treat several containers during a recurring movement of the respective treatment device, which increases the throughput.

In a preferred embodiment, a drive device of at least one of the transport devices arranged inside the housing is arranged on a different side with respect to a surface spanned by the transport path than a drive device of at least one other transport device arranged inside the housing. In this way, it can be avoided that all drive devices and possibly necessary lines are arranged on one side of the surface spanned by the transport path. Rather, it is possible that, for example, the drive device for one or more of the transport devices arranged inside the housing is arranged above this surface and that those for at least one other transport device arranged inside the housing are arranged below this plane. This makes it possible to offset these drive devices so that the space inside the housing can be used more efficiently. This enables a more compact design of the container treatment apparatus.

In particular, it is preferred that at least one drive device of at least one of the transport devices arranged inside the housing is arranged outside the housing. In particular, this is a drive device that is arranged above the surface spanned by the transport path. This allows access to the drive device, for example for maintenance work, without having to open the housing.

A particularly preferred embodiment has turned out to be one in which a drive device of the container outer surface treatment device lies on a different side with respect to a plane spanned by the transport path than the drive device of the container inner surface treatment device and at least one further transport device. In particular, it is preferred that a drive device of the container outer surface treatment device is arranged above the plane spanned by the transport path. This has proved to be preferred in particular if the holding elements of the container outer surface treatment device are holding elements gripping the respective container on the inside. With this design, the space below the container outer surface treatment device is at least largely free. The hanging transported containers are thus not disturbed by objects that may protrude into the transport path, such as a supply line to the drive unit. Furthermore, this design offers the advantage that when the holding elements are controlled, for example a displacement of a holding element relative to another holding element, for example in the height direction, by means of a control cam, this control cam is preferably the only element arranged below the carrier of the container outer surface treatment device and is therefore particularly easily accessible for adjustments.

In a preferred embodiment, the container inner surface treatment device comprises a plurality of treatment devices, for example nozzles or beam fingers, each of which can preferably be introduced at least in sections into the interior of a container for the treatment of that container. This also enables an increase in throughput, as the treatment of several containers is made possible during a recurring movement, preferably a rotation about a central axis, of the container inner surface treatment device.

Preferably, at most two further transport devices are arranged inside the housing in addition to the container outer surface treatment device and the container inner surface treatment device. In this way, the volume of the space enclosed by the housing can be further reduced and the container treatment apparatus can be designed to be particularly compact. In a further preferred embodiment, there is only one further transport device for transporting a container through the space enclosed by the housing. This embodiment enables a further reduction of the volume. Furthermore, in this embodiment it is possible to deliver the containers after treatment by the container treatment apparatus to a treatment device following in the transport path in the same way as is the case with treatment apparatus known from the prior art with, for example, five transport devices. Due to the fact that in this embodiment there is also an uneven number of all transport devices within the space surrounded by the housing, the direction of rotation of the first and last transport device along the transport path within the housing is identical.

Preferably, the at least one further transport device has a rotatable carrier. In this way, it can be combined particularly easily with the container outer surface treatment device and/or the container inner surface treatment device and can transfer containers to it and/or pick them up from it. In particular, it is preferred that the further transport device is a transport starwheel. Such transport starwheels are known from the state of the art and their integration into a container treatment apparatus is possible with reasonable effort.

Preferably, the housing encloses a clean room. This is particularly preferred if the container treatment apparatus is a sterilisation device. In this way, at least a partial area can be kept sterile inside the housing and contamination of the containers sterilised inside the housing can be avoided.

Alternatively or additionally, it is preferred that the housing is a radiation barrier. If radiation is used to sterilise a container surface, the escape of this radiation or of scattered radiation resulting therefrom from the housing can thus be prevented. This serves in particular to protect persons who are in the vicinity of such a container treatment apparatus.

Preferably, a distance between two containers directly following each other on the transport path can be changed in the area of the container outer surface treatment device and/or the container inner surface treatment device. This allows the container to be moved past the container treatment device at an individually adjustable speed. Thus, the treatment can be adjusted to the required duration without having to adjust the speed of the entire carrier on which the holding device is arranged. This results in the possibility of a high throughput with sufficient container treatment time at the same time.

Preferably, a holding device of the container outer surface treatment device is a holding device gripping the container internally and/or a holding device of the container inner surface treatment device is a holding device gripping the container externally. These embodiments enable the container to be held, at least at a container treatment device, on one side by a holding device on a container surface which is opposite the container surface to be treated. This means that no parts of the holding device need to contact the container surface to be treated, so that it is freely accessible for the treatment to be carried out by the container treatment device. For example, it is thus possible to apply the entire surface to be treated with a sterilisation medium such as a sterilisation agent solution or sterilising radiation.

In the following, a container is understood to be any container that is suitable for holding a medium. If reference is made to a first container and a second container, these can be identical or different. However, identical containers may have different contents. For example, if the treatment apparatus is a filling device, a first container may contain a gaseous medium and the second container may contain a liquid or other gas. It is also conceivable that the treatment apparatus is a sterilisation device. In this case, a first container could, for example, be a non-sterile container and the second container a sterile container.

Preferably, the (first and/or second) container to be treated is a bottle and/or preform. The treatment apparatus is preferably a sterilisation device or a sterilisation module. However, it is also conceivable that the treatment apparatus also comprises at least one treatment device selected from a group comprising a closure device, blowing station, filling device, heating device, cooling device and labelling device.

Preferably, the container outer surface treatment device and the container inner surface treatment device are arranged directly one after the other along the transport path. This eliminates the need for further transport devices between these two container surface treatment devices, which enables a more compact design of the container treatment device. Furthermore, additional parts to be maintained in this section are avoided, so that the maintenance effort is reduced, which can cause a standstill of the container treatment apparatus as well as the opening of the housing and a possibly resulting contamination of the space enclosed by the housing.

Preferably, the container inner surface treatment device follows the container outer surface treatment device along the transport path. It is therefore preferred that the container outer surface treatment device and the container inner surface treatment device are provided and designed in particular for a transfer of a container from the container outer surface treatment device to the container inner surface treatment device. In the case of sterilisation, for example, this has the advantage that after sterilisation of at least a section of the outer surface, in which the container is preferably held by an internally gripping holding element, the container does not have to be gripped again on the inside. This means that contamination of the interior of the container can be avoided.

In a preferred embodiment, the container outer surface treatment device and/or the container inner surface treatment device has a rotatable carrier and a plurality of holding elements arranged on this carrier and guidable on a circular path and/or on a circumferential path at a variable distance from the centre point. In the following, "circular path" is also to be understood as a circumferential path around a centre point as mentioned above, in which there are slight deviations from the ideal circular path in one or more sectors. These can occur, for example, as described below, by individually changing the distance of individual holding elements from the centre point, for example in order to flatten the circular path in certain areas or even to enable largely linear guidance of holding elements and the containers arranged thereon in a sector. Preferably, a holding element in a first sector of this circular path, in which a container is picked up, has a height relative to a vertical projection of the transport path which is different from that in a second sector, in which a container is delivered. This makes it possible to take over a container at a different height (with respect to the vertical projection of the transport path) than its delivery. This can be advantageous if the adjacent transport devices along the transport path are at different height levels.

In particular, however, this offers an advantage if the treatment by the container outer surface treatment device and/or the container inner surface treatment device provides for a height displacement of the container. In this case, it is not necessary to move the container several times in height, for example up and down again to the starting position. Rather, it is conceivable that during the treatment, the height shift is only carried out over the distance that is absolutely necessary for the process and the holding device is only shifted again to the height at which another container is picked up after the process has been completed and the treated container has been dispensed. This makes it possible, especially in the case of rotating container surface treatment devices, to carry out this displacement of the holding element not occupied by a container in a sector of a circular path in which no treatment of a container is carried out and which would therefore remain unused.

It is advantageous if the container outer surface treatment device and the container inner surface treatment device are arranged directly one after the other along the transport path of the containers. Since a container surface treatment often provides for a displacement of the container along the height direction, a container surface treatment device often has a device for displacing the holding element along the height direction anyway, so that this is particularly easy to implement.

In particular, it is preferred that the container outer surface treatment device and the container inner surface treatment device are provided and designed for a transfer of a container from the container outer surface treatment device to the container inner surface treatment device. Preferably, the container inner surface treatment device thus follows the container outer surface treatment device along the transport path. This often offers an advantage when internally gripping holding elements are used for treating the outer surface of the container. In this case, the container usually hangs below an arm on which the internal gripping holding element is arranged. In order to avoid contact between the arms of the different container surface treatment devices, it is therefore advisable that the transfer to the container inner surface treatment device takes place at a comparatively low height level.

Preferably, a holding element of the container inner surface treatment device has a lower height in the first sector than in the second sector with respect to a vertical projection of the transport path. As described above, it is convenient that the container inner surface treatment device receives a container at a comparatively low height level. The height of a vertical projection of the transport path in the sector of the container pick-up is thus low. Preferably, a displacement of the container in the height direction takes place during the container inner surface treatment. If a (complete) return of the container to the original height (i.e. the height at which it was picked up by the container inner surface treatment device) is not necessary for the container inner surface treatment, the not complete return of the container to the original height offers an advantage. This consists of the fact that, with the same rotational speed of the carrier, the treatment of the inner surface of the container can take place over a longer section of the circular path, as the return of the then unoccupied holding element to the original height can take place after the delivery of the internally treated container.

Preferably, a holding element of the container inner surface treatment device is arranged in a third sector, which lies along the transport path between the first and second sectors, at least in sections with respect to a vertical projection of the transport path at a greater height with respect to a vertical projection of the transport path than in the first sector and in the second sector. Consequently, in this embodiment, the container held by the holding element in the third sector is at least temporarily arranged at a height which is both above the height at which the container is received by the container inner surface treatment device and that at which the container is delivered. This is particularly advantageous if the container is guided along an application device for the treatment of the inner surface of the container and the height of the container is changed thereby. In particular, this enables different height areas of the container to be impacted by the application device (which is preferably immobile in its height position).

In particular, it is preferred that in a fourth sector a container treatment device is arranged at least in sections in the interior of a container. Such a container treatment device can, for example, be a nozzle or a so-called beam finger, which emits sterilising radiation and applies it to a container surface. Such beam fingers are often very sensitive and connected to a radiation and/or high-voltage source. Although it is possible to make such a beam finger movable with respect to a carrier, this is less preferred due to sensitivity and weight. Rather, it is preferred that the container treatment device has a constant height with respect to the vertical projection of the transport path. It is usually much easier to move an inexpensive, usually light and less sensitive container with respect to the container handling device such as a beam finger (fixed with respect to the common support) than to move the often complex and expensive container handling device towards the container in order to create a relative movement between the container handling device and the container necessary for the container handling.

In particular, it is preferred that the container is moved along its longitudinal axis towards the container treatment device, for example a beam finger, wherein the container treatment deco vice preferably penetrates at least in sections into the interior of the container. The container is then removed again from the container treatment device so that the latter is again completely outside the container.

Preferably, a container receptacle or a holding device is a passive element, for example a clamp. Active devices that are necessary for takeover and transfer, for example for pressing a preform into a clamp and pulling it out of a clamp against the holding force of the clamp, are preferably outsourced to the transfer device and the takeover device. In a preferred embodiment, a holding device of the container outer surface treatment device and/or the container inner surface treatment device is an active element. In such an active element, the force with which a container is gripped is preferably variable. For example, this change can be sector-dependent. This embodiment is preferred because with the active holding elements/clamps a better and safer takeover and/or transfer can be ensured.

Furthermore, the object according to the invention is solved by a method for treating containers, in which the containers are transported along a predetermined transport path through a space surrounded by the housing. The containers are transported at least in sections through a container outer surface treatment device and a container inner surface treatment device, wherein they are each held by at least one holding device during transport and/or container treatment.

In a first variant of this method, the solution of the above-mentioned object is achieved by bringing a holding device of the container outer surface treatment device or the container inner surface treatment device at least temporarily into the area of an opening of a housing wall in order to receive a container to be brought into the space surrounded by the housing or to discharge a container to be led out of the space surrounded by the housing. As described above with regard to the apparatus, this offers the possibility of reducing the number of transport devices arranged inside the housing and keeping the volume enclosed by the housing small.

Preferably, a transfer of a container takes place between the container outer surface treatment device and the container inner surface treatment device. This makes it possible to dispense with a transport device arranged between the container outer surface treatment device and the container inner surface treatment device, which can also serve to keep the volume enclosed by the housing low. In particular, it is preferred that a container is transferred from the container outer surface treatment device to the container inner surface treatment device.

Preferably, a height of a container over a vertical projection of the transport path within the space surrounded by the housing is changed at least once, preferably at least twice, more preferably at least three times. The transport path thus not only extends over two dimensions, but also uses a third dimension, in particular preferably a height direction. This is advantageous, for example, in order to bring different areas of a container into an application area of a treatment device. As described above on the apparatus side, the container can be moved relative to a beam finger, for example, in order to bring it into the interior of the container in sections and to ensure that the inner surface of the container is exposed to radiation from a short distance. Multiple displacement of a container along the height direction can be advantageous or even necessary, for example lowering the previously raised container in order to remove the beam finger from the interior of the container again.

A further solution to the object defined above results when the containers are guided, at least in sections, by a holding device of the container outer surface treatment device and/or the container inner surface treatment device on a section of the transport path, the vertical projection of which is a section of a circular path, wherein a container is received in a first sector by a holding element at a first height with respect to the vertical projection of the transport path and is delivered in a second sector at a second height different from the first height.

These and all other solutions shown can be implemented in addition to or as an alternative to the first solution described above. The process steps and embodiments of the described apparatus described in the context of preferred variants are also not limited to the solution in the context of which they are first mentioned. Rather, preferred process steps and embodiments can also provide advantages for processes and/or apparatus that were not described in direct connection with this variant, provided that this combination is technically feasible.

For example, the one-time or multiple changes in the height of a container above a vertical projection of the transport path within the space surrounded by the housing described above with regard to the first solution of the task is also a preferred process variant of the further solution of the object described only afterwards.

In the above-mentioned further solution of the object, changing the height of a container from the height in the first sector to the height in the second sector offers the advantage that a change in the height of the holding element (then not occupied by a container), which is not absolutely necessary for the container treatment, can be made in a fourth sector of the circular path along which the holding element is moved. In this way, the time necessary for this displacement can be shifted from the sector defined by the transport speed and the diameter of the carrier, in which the container treatment takes place, to the fourth sector. The time during which a holding element is in this fourth sector is usually referred to as dead time, since no activity necessary for container handling can be carried out in this sector. The possibility of using this sector for an activity necessary for the container treatment, namely the return of the holding device to the height necessary in the first sector, conversely enables a smaller radius/diameter of the carrier and thus a reduction in the volume of the space enclosed by the housing.

Preferably, the holding device of the container outer surface treatment device and/or the container inner surface treatment device in the first sector receives the container from a container outer surface treatment device or container inner surface treatment device. This process variant offers—as already described above—the possibility of dispensing with an additional transport device between the container outer surface treatment device and the container inner surface treatment device, which also leads to a reduction in the volume of the space enclosed by the housing. Furthermore, a displacement of a container along the height direction in the area of the container outer surface treatment device and/or the container inner surface treatment device is often advantageous in order to enable a treatment of the entire inner or outer surface of the container. Accordingly, at least one of these container surface treatment devices has a device for displacing the container along the height direction, so that this can also be used within the scope of this variant.

In a preferred variant, the container is delivered in the second sector at a second height that is greater (with respect to a perpendicular projection of the transport path on a plane) than the first height at which the container is picked up in the first sector. In particular in the case of a transfer from an internal gripping holding element, in which the container usually hangs below an arm, to an external gripping holding element, a pick-up at a comparatively low height level is suitable in order to avoid contact between arms and/or holding elements of the different container surface treatment devices.

Preferably, a container treatment device applies a treatment agent to the container in a fourth sector located on the transport path between the first and second sectors. As explained above, by carrying out a displacement of the holding element (not occupied by a container) into an area outside this fourth sector, which is not directly necessary for container treatment, the fourth sector can be used to a greater extent (preferably almost completely) for the process steps directly necessary for container treatment.

In a preferred method variant, the holding device is moved in a fourth sector, which is not part of the transport path of the container, from the second height to the first height in which the container is picked up in the first sector. The holding device is preferably not occupied by a container in this fourth sector as described above.

Preferably, the container is moved in the height direction during the treatment of the inner surface of the container. In particular, it is preferred that at least a part of the container is moved towards a treatment device, for example a nozzle or a radiation source. In particular, in the area of the treatment of the inner surface of the container, it is preferred that the container is placed over a (preferably immobile with respect to the carrier) (beam) finger, so that the finger projects at least partially into the interior of the container.

In particular, when a container has to be pulled downwards from an internally gripping holding element during the transfer of a container by the container inner surface treatment device, it often results that the distance that has to be covered in the height direction from the container, to penetrate the container to the area that allows effective sterilisation of the bottom of the container is greater than the distance that must necessarily be travelled when the container is withdrawn from the beam finger in order for the beam finger to be completely removed from the interior of the container. However, as soon as the beam finger is completely outside the container, the container can be transferred to a transport device following in the transport path. The (then unoccupied) holding element can be moved after the container has been dispensed.

The method described above with its preferred variants makes it possible to reduce the transport path of a container in the area of a container surface treatment device, since process steps not directly necessary for the container treatment are carried out in areas outside the transport path of the containers. Accordingly, the portion of the transport path of the treatment apparatus in which treatment of the container takes place can be increased. In this way, the treatment apparatus can be made smaller overall or the number of treatments possible in parallel can be increased. A reduction in weight and diameter is possible with the same performance.

Preferably, the holding device is guided on the movable carrier on a circular path, at least in sections. As explained above and shown in some of the figures described below, the movable carrier is preferably a transport starwheel which is rotatable about a central axis. By being arranged on the movable carrier, the holding element follows this rotation. However, as described above, a holding element can additionally be moved in a vertical or radial direction with respect to the movable carrier.

Preferably, a longitudinal axis of a container extends during its transport along the transport path essentially perpendicular to a plane defined by the transport path. The container thus extends in a height direction that is perpendicular to the transport path or the plane spanned by the transport path. Preferably, the perpendicular of the vertical projection of the transport path is parallel to the height of one, preferably each, container. The height direction above the vertical projection of the transport path is thus parallel to the height direction of the container(s).

A further solution to the problem underlying the present invention of shortening the transport path for plastic containers within a container treatment apparatus consists in a container treatment apparatus for transporting plastic containers and in particular plastic preforms along a predetermined transport path, wherein the container treatment apparatus has at least a first transport device, which has a plurality of holding elements, in particular holding clamps, for holding the plastic containers during transport, and a second transport device, which has a plurality of holding elements, in particular mandrels or holding mandrels, and the plastic containers are transferred from the first transport device to the second transport device.

In this solution—which, however, can also be a supplement to further solutions and embodiments presented within the scope of this invention—the first transport device and the second transport device are each a pitch distribution delay starwheel. Preferably, the first transport device is a (first) pitch distribution starwheel and the second transport device is a (second) pitch distribution starwheel. A pitch distribution starwheel is suitable and intended to change the pitch of successive or adjacently transported plastic containers and in particular to increase and/or decrease it. This is preferably achieved by the holding elements of the first transport device and the holding elements of the second transport device being movably and/or pivotably mounted on the respective transport device/the respective pitch distribution starwheel and, in particular, being pivotably mounted radially or tangentially relative to the transport path of the respective transport device.

Pitch distribution starwheels are therefore always used where pitches are to be varied or changed. If other functions are necessary, these are usually not carried out on the pitch distribution starwheel, but further transport starwheels or transport devices are necessary before and/or after the pitch distribution starwheels. For example, in an apparatus known from the internal prior art of the applicant, two transport starwheels are necessary in order to receive the containers with holding mandrels for an external treatment, and downstream a pitch distribution starwheel, which is only provided for changing a division. According to this, the pitch distribution starwheels known in the prior art can only perform movements horizontally, i.e. radially and/or tangentially to a plane, more precisely a circumference, of the (pitch distribution) starwheel or in relation to a longitudinal direction of the plastic container, but not in other planes such as vertically, i.e. perpendicularly to a plane of the (pitch distribution) starwheel in relation to the circumference of the (pitch distribution) starwheel or in relation to the longitudinal direction of the plastic container. Instead, these movements are usually performed on other or the additional transport units.

Accordingly, it is proposed according to the invention to transfer plastic containers directly from one pitch distribution starwheel to a further pitch distribution starwheel without additional infeed or outfeed starwheels, which are arranged between the pitch distribution starwheels or the first and second transport device. This means that the original treatment starwheel for external sterilisation and the upstream infeed starwheel are omitted inside the housing. This results in a treatment module that only needs a total of three (instead of five) transport devices or starwheels within the housing.

Preferably, a heating device is connected upstream of the container treatment apparatus, which heats the plastic containers and in particular plastic preforms to a predetermined temperature. The first transport device is advantageously arranged downstream of the heating device, so that a transfer of the plastic containers from the heating device to the container treatment apparatus, i.e. from an outlet starwheel (first transport device) of the heating device to an inlet starwheel (second transport device) of the container treatment apparatus is carried out with two pitch distribution starwheels without further transport starwheels or transport devices being arranged between these pitch distribution starwheels.

The above-mentioned housing preferably has an enclosure within which a clean room is preferably formed. The first transport device is preferably arranged outside the housing and thus outside the clean room and the second transport device is preferably arranged inside the housing and in particular inside the clean room. The first transport device thus preferably transfers the plastic containers to the second transport device, which is arranged inside a housing that shields the environment. The second transport device or the second pitch distribution starwheel is therefore preferably aseptic.

In a preferred embodiment, the container treatment apparatus comprises a housing, wherein the transport path is at least partially within the housing.

In a preferred embodiment, the container treatment apparatus has a container outer surface treatment device for treating outer surfaces of the plastic containers, in particular a container outer surface sterilisation device and/or a container inner surface treatment device for treating inner surfaces of the plastic containers, in particular a container inner surface sterilisation device.

The container outer surface treatment device and the container inner surface treatment device are preferably arranged within the housing. Preferably, at least the second transport device, the container outer surface treatment device and the container inner surface treatment device are arranged inside the housing, so that the treatment and in particular the sterilisation of the plastic containers preferably takes place inside the housing or inside the clean room formed by the housing.

The container outer surface sterilisation device and the container inner surface sterilisation device sterilise the containers and in particular preforms preferably by means of electron beams. For this purpose, the container outer surface sterilisation device preferably has at least one so-called surface radiator, which is preferably arranged along the transport path of the containers and is directed towards their outer surfaces, and the container inner surface sterilisation device preferably has at least one and preferably a plurality of beam fingers, which are introduced into the containers.

In a further preferred embodiment, the container outer surface treatment device is arranged on the second transport device. The container outer surface treatment device and, in particular, the container outer surface sterilisation device is therefore preferably arranged directly on the (second) pitch distribution starwheel, so that, as usual in the state of the art, a treatment starwheel specially provided for external sterilisation or external treatment is not required.

The container inner surface treatment device and in particular the container inner surface sterilisation device is preferably arranged on a transport starwheel following the second transport device.

The first transport device or the pitch distribution starwheel arranged downstream of the heating device therefore preferably transfers the plastic containers directly to a further pitch distribution starwheel, at which an external treatment of plastic containers is also carried out directly. In the state of the art, an infeed starwheel is usually first provided after the first pitch distribution starwheel inside the housing, which transfers the containers to the subsequent transport starwheel for external sterilisation, which in turn transfers the containers to the second pitch distribution starwheel after external treatment.

The container treatment apparatus according to the invention or the proposed transfer from a pitch distribution starwheel to a directly following pitch distribution starwheel, on which the external treatment is also carried out, therefore eliminates the inlet starwheel and the treatment transport starwheel arranged in the housing, so that the housing can in particular also be designed smaller overall.

In a preferred embodiment, the housing has a transfer window for transferring the plastic containers from the first transport device, which is arranged outside the housing, to the second transport device, which is arranged inside the housing. Preferably, the transfer window is arranged in a transfer section in which the plastic containers are transferred from the first transport device to the second transport device.

At the transfer window, the pitch of the plastic containers is preferably variable so that the pitch distribution of the first pitch distribution starwheel is optimally designed for or adaptable to the requirements of the second pitch distribution starwheel.

In a preferred embodiment, the transfer window has a width of between 250 mm and 320 mm, preferably between 270 mm and 310 mm and particularly preferably between 285 mm and 300 mm. Advantageously, the transfer window is designed to be as small as possible, so that any sterility inside the housing can be maintained and at the same time the exit window for possible radiation escaping from the housing is reduced. Preferably, the transfer window is designed variably so that its width can be changed. This is advantageous, for example, because the transfer window can thus be adapted to different preform types and sizes. These transfer windows can also be referred to as input or output.

In a further preferred embodiment, the second transport device has a lifting and rotating device which enables a movement of the holding element of the second transport device in a vertical and/or horizontal direction with respect to a longitudinal axis of the plastic container and a rotational movement of the plastic container and/or the holding element along the longitudinal axis. Preferably, each holding element of the second transport device is associated with its own lifting and rotating device, so that the plastic containers can be rotated independently of each other and/or the holding elements can be moved independently of each other. A drive device is preferably assigned to each lifting and rotating device, in particular for carrying out the rotational movement of the plastic container, which is designed in a known manner. The lifting movement of the holding element in vertical direction is preferably realised by one or more lifting curves and at least one guiding curve.

In order to enable the transfer from the first transport device to the second transport device and in particular from the first pitch distribution starwheel to the second pitch distribution starwheel, a lifting and rotating device is therefore additionally arranged on the second transport device/the second pitch distribution starwheel, which is preferably suitable and intended for receiving the plastic containers.

The lifting and rotating device is required in order, on the one hand, to be able to pick up the plastic containers and hold them internally, wherein the transfer from the holding elements and, in particular, holding clamps of the first transport device to the holding elements and, in particular, holding mandrels of the second transport device preferably takes place by moving the holding elements of the second transport device towards the containers and thus preferably in a vertical direction or in the longitudinal direction of the containers, so that the holding element is moved in the direction of the container. On the other hand, the lifting and rotating device serves to rotate the containers about their longitudinal axis in front of the container outer surface treatment device and, in particular, the container outer surface sterilisation device, so that an evenly distributed radiation power on the circumference and, as a result, an even disinfection power can be applied to the containers.

The holding elements of the first transport device are preferably holding clamps which hold the plastic containers on an outer wall and in particular below or above the support ring of the containers. The holding elements of the second transport device are preferably holding mandrels which are inserted into the containers and hold them against an inner wall. The plastic containers are thus preferably transferred from an outer holding element to an inner holding element and in particular from an outer holding clamp to an inner holding mandrel.

Advantageously, the lifting and rotating device also enables the container to be optimally placed on the holding mandrel. The holding mandrel is preferably rotatable so that a rotary movement of the plastic container can be initiated, in particular during the treatment of the container.

In a preferred embodiment, a shielding device is arranged at least in sections in the area of the transfer window, which shields the surroundings of the housing from the interior of the housing. In particular, this is a radiation shielding device for shielding radiation from the container outer surface treatment device and/or the container inner surface treatment device and in particular arising X-rays. Accordingly, the plastic container is preferably transferred into a radiation-shielded housing.

It is therefore proposed to arrange the external sterilisation of the plastic containers and in particular plastic preforms on the second transport device and preferably on the second pitch distribution starwheel. In order to make this possible, the container outer surface treatment device or the surface radiator is preferably arranged on the second transport device or the second pitch distribution starwheel, and the second transport device or the second pitch distribution starwheel is equipped with an additional lifting and rotating device. The transfer from the outlet starwheel of the oven (first transport device) to the radiation-shielded area is therefore preferably carried out by the first pitch distribution starwheel. The second pitch distribution starwheel is therefore arranged within the radiation-shielded area, i.e. within the housing.

In a further preferred embodiment, the first transport device and/or the holding elements of the first transport device follow and accompany the transport path of the second transport device and/or the holding elements of the second transport devices at least partially or in sections during the transfer of the plastic containers to the second transport device. In other words, the plastic container is preferably held at least temporarily and in sections simultaneously by the holding element, in particular the holding clamp, of the first transport device and the holding element, in particular the holding mandrel, of the second transport device at or during the transfer.

During the transfer from the first transport device arranged outside the housing to the second transport device inside the radiation-shielded housing, the first transport device or the holding element of the first transport device preferably accompanies the plastic containers at least temporarily. The transfer is therefore preferably carried out in an accompanying manner.

In order to improve the transfer from the first pitch distribution starwheel (first transport device) to the second pitch distribution starwheel (second transport device) and to make it easier and safer to place on the holding elements and in particular the holding mandrels of the second pitch distribution starwheel, the first pitch distribution starwheel preferably accompanies the transfer of the plastic containers and in particular plastic preforms in sections on a circular path which corresponds to the circular path of the second pitch distribution starwheel.

As mentioned above, the lifting and rotating device preferably carries out a lifting movement of the holding element or holding mandrel, wherein the holding mandrel is preferably moved towards the plastic container and is inserted into the container in order to hold it. In order to enable the lifting movement for attaching the plastic container to the holding mandrel of the lifting and rotating device, a first and a second lifting cam as well as a guide roller are preferably arranged inside the housing, which enable the lifting and lowering of the holding mandrel.

Thereby, the first pitch distribution starwheel preferably leaves its actual transport path, which is preferably an essentially circular path, in order to accompany the transport path and preferably circular path of the second pitch distribution starwheel. The second pitch distribution starwheel preferably moves on a substantially exact circular path, so that a guide roller of the lifting and rotating device can roll on the lifting curve without transverse wear or without slipping. In this context, substantially means that the transport path of the second transport device or of the second pitch distribution starwheel deviates only minimally from a circular path, wherein this also results from the changing distances of the holding elements from each other and the different distances of the holding elements from the axis of rotation of the pitch distribution starwheel. The attachment of the container to the holding mandrel is thus not punctual, but accompanying.

The lifting cam is preferably arranged inside the housing on a stationary side wall of the housing. A lower area of the housing is advantageously designed to be movable and can preferably be lowered completely to allow access for adjustment and maintenance work inside the housing. Such a lowering is described in more detail in DE 10 2013 109 794 A1, for example. The embodiments described therein each also represent preferred embodiments of the lowerable housing part of the present invention. The applicant expressly reserves the right to use features of this document to define preferred embodiments of the present invention.

In addition, a shielding device, such as in particular a radiation protection wall, is arranged inside the housing and preferably at least partially or in sections in the region of the second pitch distribution starwheel and in particular at least in the region of the transfer window, which preferably shields the harmful X-rays produced by the container outer treatment device and/or container inner treatment device from the outer region of the housing.

Preferably, one section of the housing, and in particular an upper section of the housing, is arranged stationary and a further section, in particular a lower section, which is a bottom, is arranged movable and in particular lowerable. The lower section is preferably also a shielding device, such as in particular a radiation protection wall. The arrangement of the two shielding devices is designed in such a way that the lifting and rotating device and in particular at least one guide roller of the lifting and rotating device can move on a track through a gap between the two shielding devices.

In the area of the transfer window, a part of the lower shielding device is preferably arranged on the lifting cam. This part is therefore preferably designed so that it can be dismantled during adjustment work on the container transfer without having to adjust the fastening of the lifting cam. Preferably, the lower shielding device and the lifting cam can be removed together. This means that the radiation shield can be removed to enable or facilitate adjustment without having to remove parts of the transfers.

According to another embodiment, it would also be conceivable that the second pitch distribution starwheel moves towards the first pitch distribution starwheel during the transfer or that both move towards each other at the same time. This could minimise the transfer window in the housing. Preferably, the first pitch distribution starwheel and the second pitch distribution starwheel could also be electrically controlled, for example by means of a long-stator technology or the like.

In order to solve the above-mentioned problem, the present invention is further directed to a method for transporting plastic containers and, in particular, plastic preforms along a predetermined transport path, wherein the plastic containers are transported at least by means of a first transport device, which has a plurality of holding elements, in particular holding clamps, for holding the plastic containers during transport, and a second transport device, which has a plurality of holding elements, in particular mandrels, and are transferred from the first transport device to the second transport device.

In this solution—which, however, can also be a supplement to further solutions and embodiments presented within the scope of this invention—the first transport device and the second transport device are each a pitch distribution starwheel, so that the plastic containers are transferred from one pitch distribution starwheel to a subsequent pitch distribution starwheel. The first transport device is preferably a first pitch distribution starwheel and the second transport device is a second pitch distribution starwheel.

Accordingly, it is also proposed on the process side to carry out a transfer of plastic containers directly from one pitch distribution starwheel to a further and, in particular, directly following pitch distribution starwheel without further transport starwheels, such as additional infeed or outfeed starwheels, being arranged between these pitch distribution starwheels.

In a preferred method, the second transport device is suitable and intended to move the holding elements (of the second transport device) with respect to a longitudinal axis of the plastic containers along a vertical and/or horizontal direction and to rotate the plastic containers or the holding elements about their longitudinal axis.

In a further preferred method, treatment and in particular sterilisation of the outer surfaces of the plastic containers is carried out on the second transport device.

In particular, the apparatus and methods described above are also designed and intended for carrying out this described method, i.e. all features described for the apparatus and methods described above are also disclosed for the method described here and vice versa.

A further solution to the problem underlying the present invention consists in a container treatment apparatus for transporting plastic containers and, in particular, plastic preforms along a predetermined transport path, wherein the container treatment apparatus having at least one transport device which has a plurality of holding elements.

In this solution—which, however, can also be a supplement to other solutions and embodiments presented within the scope of this invention—the transport device is a pitch distribution starwheel which has a movement device which is suitable and intended to enable movement of the holding elements in at least two planes.

In a preferred embodiment, the container treatment device comprises at least a first transport device and a second transport device, wherein the plastic containers are transferred from the first transport device to the second transport device.

The combination of a direct transfer from a first pitch distribution starwheel to a second pitch distribution starwheel and a movement of the holding elements in at least two planes preferably saves space and transport path and allows additional functions for the pitch distribution starwheel as well as additional forms of transfer.

Even without the transfer of the above-mentioned pitch distribution starwheel to a further pitch distribution starwheel, the movement of the holding elements in several and in particular two planes can create an additional function on the pitch distribution starwheel, for which a further transport starwheel was previously necessary, and thus shorten the transport.

The movement in at least two planes is preferably a movement of the holding element in a horizontal and/or vertical direction and/or a rotation of the holding element. Vertical means perpendicular to the transport device or the pitch distribution starwheel in relation to a circumference of the transport device or a transport path of the plastic containers along the transport device or in relation to a longitudinal axis of the plastic container and/or the holding element, which is preferably a holding mandrel. Horizontal means radial and/or tangential to the circumference of the transport device or a transport path of the plastic containers along the transport device or in relation to a longitudinal axis of the plastic container. Rotation in this context means a rotation or a rotation of the holding element about its own longitudinal axis of the holding element, wherein this rotation in particular causes a plastic container held by the holding element to rotate about its longitudinal axis.

The movement device is therefore preferably the lifting and rotating device mentioned above. All the above-mentioned features can therefore also be applied to or combined with this embodiment and vice versa.

In a preferred embodiment, the first transport device and the second transport device are each a pitch distribution starwheel, so that even when the holding element is moved in at least two planes on the pitch distribution starwheel, a transfer takes place in the manner described above from a first pitch distribution starwheel to a second pitch distribution starwheel.

In a further preferred embodiment, the container treatment apparatus also has a container outer surface treatment device for treating outer surfaces of the plastic containers, in particular a container outer surface sterilisation device and/or a container inner surface treatment device for treating inner surfaces of the plastic containers, in particular a container inner surface sterilisation device, wherein the container outer surface treatment device preferably being arranged on the second transport device.

The combination of a direct transfer from a first pitch distribution starwheel to a second pitch distribution starwheel and a movement of the holding elements in at least two planes is particularly advantageous for the external treatment of plastic containers. In particular, the pitch distribution is necessary in order to optimise the spacing of the containers for external treatment. In particular, the vertical position of the container can be varied during circulation, for example relative to the treatment window to optimise the irradiation.

In a further preferred embodiment, the movement device is suitable and intended to enable movement of the holding elements in three planes. Accordingly, the holding element can preferably perform movements in the horizontal and vertical directions described above and rotate.

In a preferred embodiment, the plurality of retaining elements are holding mandrels. These internally gripping mandrels are particularly advantageous in external treatment, as this means that all external surfaces are accessible for treatment and are not covered by holding elements.

In a further preferred embodiment, the transport device comprises at least one lifting cam and at least one guide roller, which together are suitable and intended to allow at least one movement of the holding element in at least one plane. This movement is the movement in vertical direction. Preferably, the at least one lifting cam and the at least one guide roller thus serve to execute the movement of the holding element in the vertical direction. The guide roller is guided on the lifting curve, which has correspondingly higher and lower areas for the movement of the holding element in the vertical direction and in particular an up and down movement of the holding element as seen from the centre of the earth. The movement in the horizontal direction can be carried out in the previously known manner on the pitch distribution starwheel. It would also be conceivable to carry out the vertical movement by means of a drive device, for example.

In order to solve the above-mentioned problem, the present invention is also directed to a method for transporting plastic containers and, in particular, plastic preforms along a predetermined transport path, wherein the plastic containers are transported at least by means of a transport device which has a plurality of holding elements, in particular holding mandrels.

In this solution—which, however, can also be a supplement to further solutions and embodiments presented within the scope of the present invention—the transport device is a pitch distribution starwheel, which enables the holding elements to be moved in at least two planes.

In a preferred method, the transport device is suitable and intended to move the holding elements in a vertical direction and/or a horizontal direction and/or to rotate the holding elements.

In a further preferred method, treatment and in particular sterilisation of the outer surfaces of the plastic containers is carried out on the transport device.

In particular, the apparatus and methods described above are also designed and intended for carrying out this described method, i.e. all features described for the apparatus and methods described above are also disclosed for the method described here and vice versa.

The present invention is further directed to a container treatment apparatus and a corresponding method, in which a treatment and, in particular, a sterilisation of containers is also carried out using a so-called pitch distribution starwheel. The invention is again described with reference to the sterilisation of containers, but it is noted that the invention can also be applied to other units such as, for example, printing units, labelling units or inspection units.

As mentioned above, the sterilisation models known from the applicant's internal prior art sometimes have a high number of transport devices, for example five transport starwheels. This results in a relatively long dwell time within the sterilisation module.

The invention is therefore based on the object of reducing the dwell time of the containers, in particular in the context of sterilisation, but also during other treatments. This is achieved according to the invention by the subject matters of the independent patent claims. Advantageous embodiments and further developments are the subject of the subclaims.

A container treatment apparatus according to the invention comprises a transport apparatus for transporting the container along a predetermined transport path, wherein the transport apparatus comprises at least one transport device for transporting the container, as well as at least one container treatment device for treating the container in a predetermined manner. In this case, this transport device has a (preferably rotatable) carrier on which a plurality of holding devices for holding at least one container are arranged. Instead of this rotatable carrier, the carrier can also be designed as an elongated stator, which preferably forms a component of a linear motor, wherein the holding devices are preferably designed on shuttles which are movable relative to this elongated stator (wherein these shuttles represent the rotors of the linear motor).

In a first embodiment according to the invention, these holding devices are movable with respect to the carrier in such a way that a distance between two containers immediately following each other on the transport path can be changed. Furthermore, this container treatment device is arranged in such a way that it can treat the containers transported by the transport devices.

In a further embodiment according to the invention, the holding device is rotatable in such a way that the container held by this holding device is rotatable with respect to its longitudinal direction.

In a further embodiment according to the invention, as mentioned above, a linear motor drive is provided instead of a transport device with a rotatable carrier. In this embodiment, a long stator with a plurality of magnetic or magnetisable elements is provided, opposite which one or more shuttles can move. Again, preferably, this long stator has a substantially rectilinear section on which, particularly preferably, the treatment device is arranged. In other words, the transport device preferably has a carrier, which is designed as a stator, in particular a stationary carrier, on which a plurality of holding devices, which preferably each have (or form) a runner, are arranged for holding at least one container.

It is pointed out that the above-mentioned task can be achieved by the three above-mentioned embodiments according to the invention. Nevertheless, it is also possible to combine these embodiments with each other, in particular to combine the change of a distance between the holding devices with the rotatability of the holding devices.

In a preferred embodiment, the containers are selected from a group of containers comprising plastic preforms, plastic bottles, glass bottles and the like. In particular, the containers are plastic preforms.

Particularly preferably, the holding devices are arranged on swivelling and/or linearly displaceable arms. Particularly preferably, the holding devices or components of the holding devices are rotatable relative to these swivelling arms. Particularly preferably, the holding devices are pivotable relative to the carrier. In a further preferred embodiment, the holding devices are also movable in a rectilinear direction relative to the carrier.

In a preferred embodiment, the transport device is a so-called pitch distribution starwheel, i.e. a transport device which can change the distribution of the transported containers. Preferably, the pitch distribution starwheel is designed in the manner described below or above in the context of this application.

Particularly preferably, the treatment of the containers takes place in a straight section of the transport path. Particularly preferably, the container treatment device is stationary and the containers move past it.

Particularly preferably, the distance between two containers directly following each other on the transport path can be changed during the movement of the containers. Particularly preferably, containers transported by the transport device can be transported at least in sections along a straight line.

In a further advantageous embodiment, the container treatment device is suitable and intended for treating an outer surface of the containers. In this embodiment, it is possible and preferred that the treatment device is arranged in particular laterally next to a transport path of the containers.

In particular, the treatment device is arranged laterally next to the transport path but at a small distance from it. A small distance is understood to be less than 10 cm, preferably less than 8 cm, preferably less than 6 cm and preferably less than 5 cm.

In a further advantageous embodiment, the transport device has a drive device and preferably a plurality of drive devices by means of which the containers held by the holding devices can be rotated with respect to their longitudinal axis. This can be an electric motor drive, for example, but other drives could also be considered.

Particularly preferably, the at least one drive device generates the rotary movements of the containers and/or their holding devices without contact. For example, a magnetic coupling is conceivable, which can also extend through a housing within which the arrangement is located. This is explained in more detail with reference to the figures.

Particularly preferably, the containers and especially the containers held on the holding devices can be moved in their longitudinal direction. In this way, the treatment of the containers can be improved. It is possible that the containers can be moved together with the holding device holding them or also with respect to the holding device. It is possible that each of the containers can be moved individually in its longitudinal direction. However, it would also be conceivable that a joint movement of the holding devices and/or the containers takes place, for example by means of a lifting curve. In addition, linear motor drive devices could also be provided to achieve this movement in the longitudinal direction of the containers.

In a further advantageous embodiment, the container treatment device is selected from a group of container treatment devices comprising container outer surface treatment devices, in particular container outer surface sterilisation devices, container inner surface treatment devices, in particular container inner surface sterilisation devices, container inspection devices, container printing devices, container marking devices and the like.

In the following, particular reference is made to the sterilisation of a container to be filled or a plastic preform (which is in particular formed into such a container). The sterilisation of a container to be filled is, in addition to the actual filling process, the central process step in an aseptic filling line. Newer developments use ionising radiation, especially electron radiation, to achieve germ reduction. In most applications, this radiation consists of accelerated electrons (but also, or alternatively, ultraviolet radiation), which are generated in a corresponding system and thus reach in or on the container to be sterilised.

Systems known in the prior art of the applicant which are used for sterilisation have an electron-generating device, as well as a beam finger for sterilising the inner surfaces and an electron-generating device and, in addition, also a surface radiator, in particular for sterilising outer surfaces.

In known concepts, the sterilisation of the outer surfaces precedes the sterilisation of the inner surfaces. This is sometimes done on carousels, as already explained above. Usually, such transport devices or carousels are connected to a pitch distribution starwheel. The resulting X-rays should be shielded from the environment by suitable shielding. Thus, the two treatment devices are embedded or enclosed in a radiation-shielding device. In order to ensure radiation shielding also at an outlet starwheel, in each case an inlet starwheel is connected upstream and an outlet starwheel is connected downstream. In this way, the applicant's prior art results in an overall device which is equipped with five stars or carousels.

This results in various disadvantages, which lie primarily in the excessively long transfer, for example from an oven to a blow-moulding machine, or in the long dwell time in the treatment module. This is due to the five-star design. This also results in great difficulties when moulding plastic preforms into finished containers, especially if the plastic preforms have somewhat unfavourable stretching ratios.

In addition, frequent transfers, especially within a poorly accessible radiation-shielding housing, increase the risk of faulty transfers. In the prior art of the applicant, a punctual transfer from a clamping star to an insertion mandrel takes place in particular during a transition from the inlet starwheel to an external treatment module. Mistakes such as misalignment or the like can then lead to a loss of the plastic preform or even damage to the transfer device during subsequent transfers.

With higher outputs, the footprint of the plant also increases because all starwheels or carousels would grow with the higher output.

The invention now proposes to carry out the external sterilisation of the plastic preforms at the pitch distribution starwheel. In order to make this possible, the treatment device, and in particular a surface radiator, is placed on the pitch distribution starwheel and the pitch distribution starwheel is preferably equipped with an additional lifting and rotating unit.

This makes it possible to extend the dwell time of the plastic preforms at the treatment device and preferably at a window of the surface radiator and thus to ensure the required radiation dose for sterilising the plastic preforms.

In order to be able to distribute the dose evenly around the circumference of the plastic preform, the pitch distribution starwheel is preferably equipped with a lifting rotation device which makes it possible to rotate the plastic preform in front of the treatment device and in particular in front of the window of the surface radiator. The rotation should preferably go once completely over 360°, but multiple rotations would also be conceivable and desirable.

However, it is also conceivable to work with slightly smaller rotations than 360°, since the surface radiator treats the entire side of the plastic preform facing it, even if not homogeneously.

By using a pitch distribution starwheel (TVS) to move the plastic preform in front of the surface blaster, it is possible on the one hand to increase the treatment time or the packing density in front of the treatment window and on the other hand also to optimise the running path of the plastic preforms in front of the surface radiator.

This means that ideally a straight path or a maximum circular path can be followed in front of the surface radiator and that the distance at the sides of the blasting window is not increased excessively. This is advantageous because the dose on the plastic preform decreases with increased distance during treatment. The dose distribution over the circumference of the plastic preform would therefore not be uniform.

In a preferred embodiment, the surface radiator has a flat surface or radiating surface.

Inside the module or housing, and in particular at least partially around the inner part of the pitch distribution starwheel, there is preferably a radiation protection wall which protects against the harmful X-ray Bremssstrahlung of the surface radiator, but also against the radiation of the finger emitter is sealed off from the outside.

Preferably, an upper part is fixed to the housing and a lower part is fixed to the lowerable bottom. Both radiation shielding walls are particularly preferably arranged in an overlapping manner and the gap between the two shielding walls is advantageously designed in such a way that the lifting and rotating device can move on a track, in particular through the gap between the two shields which are fixed in operation.

The radiation shielding walls of the housing are advantageously made of a special radiation shielding material, for example of lead encased in stainless steel or of tungsten or of a tungsten-sintered composite or of a material with similar properties.

However, parts of the shielding are also preferably made of stainless steel or cast material. The adaptation of the shielding material to a better radiation tightness results above all in a considerably smaller wall thickness of the shielding and thus the possibility to move with the lifting and rotating unit between the two shielding walls on the track of the pitch distribution starwheel or to let the shielding protrude into the lifting and rotating device without having to widen or enlarge it unduly.

The shielding walls of the housing preferably follow the track of the TVS or are identical or very similar to the plastic preform track. The track of the TVS can also be adapted to allow movement to the side of the surface radiator towards the surface radiator in order to improve the radiation shielding with the shielding that follows the track of the plastic preform (also called preform).

This would make it possible to shield a large part of the X-ray Bremsstrahlung directly at or in the vicinity of the surface radiator without the harmful radiation being able to reach far into the housing. This would also make it possible to quickly reduce the required wall thicknesses, which would save costs and weight.

A further embodiment would be the use of a type of long-stator drive with shuttles that could replace the TVS or take over its functions. The advantage here would be the even freer movement of the travel profile and thus the longer dwell time in front of the surface radiator.

In this embodiment, the use of a linear motor is proposed. As described above, this could also have a straight course in the area of the treatment device or a course with a very high radius of curvature.

The rotary movement is preferably introduced to the lifting and rotating unit in compliance with aseptic aspects and is most advantageously transmitted without contact.

But all other possibilities up to the driven toothed belt are also conceivable.

An essential aspect of this design according to the invention is the attachment of the surface radiator to the pitch distribution starwheel and thus, preferably, making the three-star concept possible. This results in considerable advantages by shortening the dwell time of the plastic preforms in the module or in the apparatus. In addition, the dwell time of the plastic preforms upstream of the treatment device, in particular upstream of the surface radiator, can be increased in order to be able to achieve high sterilisation rates.

The path curve in front of the surface radiator can also be optimised in this way in order to increase the radiation dose at the sides of the surface radiator. The distance in front of the surface radiator can thus be positioned as close as possible to the radiation window or is not raised at the edges.

In a preferred embodiment, a distance between the surface radiator and the container or plastic preform is less than 10 cm, preferably less than 8 cm, preferably less than 6 cm, preferably less than 5 cm, preferably less than 4 cm, preferably less than 3 cm and particularly preferably less than 2 cm.

As mentioned above, the outer surface of plastic preforms is sterilised in a partial step using electron beams. The plastic preform rotates around its longitudinal axis in front of an electron source so that all surface points on the outside of the plastic preform receive as uniform an irradiation dose as possible.

In the prior art, the plastic preform is rotated in front of an electron source by driving its carrier, for example by belts or pinions. The disadvantages here are abrasion and dirt, which inevitably occur due to the contact drive. Especially in an aseptic environment, such potential contamination is a major problem.

A magnetic drive is known from EP 3 431 402 which initiates a rotary movement without contact and therefore almost manages without a drive. However, the uniformity of the rotational speed is a disadvantage here, as strongly varying torques occur due to the magnetic coupling. This can result in the plastic preform not rotating uniformly in front of the radiation source and the dose distribution on the surface of the outside of the plastic preform not being constant.

It is thus proposed to transport the plastic preform not on a transport starwheel with constant pitch in front of the electron radiator, as is usually the case, but on a pitch distribution starwheel (TVS). This allows a variable tangential speed at different points of the starwheel.

In order to rotate the plastic preform around its longitudinal axis, it is proposed to integrate rotation mandrels into this TVS, onto which the plastic preform can be placed, in particular from below. The mandrels are rotated around their longitudinal axis at least in the area of the electron source in order to irradiate the outer shell of the plastic preform as uniformly as possible.

A magnetic drive and/or a contactless drive is used to drive the rotary mandrels.

In a preferred embodiment, the drive has a rotational speed smoothing device that causes the rotary drive not to be subject to high rotational speed variations. This is explained in more detail below.

In a preferred embodiment, the container treatment apparatus has a housing within which at least one transport device is arranged and this housing preferably forms a clean room which shields an interior of this housing from a (particularly non-sterile) environment. Particularly preferably, the pitch distribution starwheel described here is arranged within this housing. Preferably, further transport devices are also arranged within this housing.

Particularly preferably, this housing is designed at least in sections as a radiation shielding housing, in particular for protection against beta and/or gamma radiation, but also against X-ray radiation.

In a further preferred embodiment, at least one wall of the housing runs parallel to a section of the transport path of the containers. Due to this course, the overall size of the housing can be reduced. In particular, this is a wall running in a straight line along the transport path of the plastic preforms.

In a further advantageous embodiment, the container treatment apparatus has at least one further transport device for transporting the containers, and preferably at least two further transport devices, and particularly preferably exactly two further transport devices, which serve to transport the containers and in particular plastic preforms.

In a further preferred embodiment, the container treatment apparatus comprises at least one second container treatment device, wherein this second container treatment device is particularly preferably a container inner surface treatment device and in particular a container inner surface sterilisation device.

As mentioned above, this second treatment device preferably has a plurality of beam fingers which can be introduced into the containers in order to act upon them with electron radiation. Particularly preferably, electron acceleration devices are provided in each case, as well as exit windows for the exit of the electron beams, which are preferably made of titanium.

In a further advantageous embodiment, the drive device generates the rotary movement of the holding devices by means of magnetic forces. As explained in more detail below, a rotor with a plurality of magnets can be arranged on the holding device, the rotary movement of which is generated by a stator which also has a plurality of magnets or magnetic or magnetisable elements.

In a further advantageous embodiment, the container treatment device has a monitoring device for monitoring the rotational movement of the containers. Particularly preferably, this monitoring device has an image recording device or at least one coil. For example, currents or voltages can be induced in a coil, which in turn are a measure for monitoring the rotary movement. It would be possible, for example, for a plurality of coils to be provided which are arranged between magnets, for example within a stator. Preferably, the monitoring device is suitable and intended to detect a standstill of the rotational movement of the plastic preforms and/or a deviation of the rotational speeds of the plastic preforms (or the holding devices holding them).

In a particularly preferred embodiment, the drive device has a rotor coupled to the holding device, on which a plurality of magnets are arranged, and a stator, on which a plurality of magnets or magnetic elements are preferably also arranged. In this way, the rotary movement is transmitted by magnetic forces between a stator and a rotor. It would be possible for this stator to be arranged outside or inside the housing and for the transmission of the magnetic forces to take place through a housing wall.

In a preferred embodiment, the stator is rectilinear and/or the magnetic elements of the stator extend along a rectilinear direction. Particularly preferably, the rotor is circular. In this embodiment, a rectilinear stator therefore interacts with a circular rotor.

Particularly preferably, the magnets or magnetic elements (or a longitudinal direction of these magnets or magnetic elements of the rotor and/or the stator) extend at least in sections obliquely with respect to a direction which is parallel to the axis of rotation of the holding device.

In the vertical arrangement of magnets shown in EP 3 431 402, the attraction forces vary greatly along the direction of transport because at one position the magnets are exactly opposite each other. In this case, no torque is transmitted and at another position there is repulsion and attraction and thus a high torque. This high variance in the torque leads to (unintentional) speed fluctuations. This problem increases with increasing transversal speed of the rollers, i.e. with increasing production rates. Above a certain transversal speed, the torque fluctuations mean that the roller can no longer be synchronised into the magnetic pitch and thus no longer performs a continuous rotary movement.

The improved shape of the permanent magnets described here, in particular on a stator, which is especially preferably designed as a fixed bar, and a rotor (which is designed as a magnetic roller, for example) can have a smoothing effect on the torque curve along the transport path. For example, obliquely toothed magnet arrangements can be provided.

In a preferred embodiment, the magnets and/or magnetic elements run in a straight line but at an angle and/or skew with respect to said axis of rotation. In a further preferred embodiment, the magnets and/or magnetic elements run at an angle to the axis of rotation. In a further preferred embodiment, the magnets or magnetic elements are curved.

In a further preferred embodiment, the individual magnets are spaced apart in the direction of transport of the plastic preforms.

In a preferred embodiment, only one of the two magnetic partners carries magnets and the other has a material with high magnetic permeability, such as iron. By suitably guiding the magnetic fluxes, torque fluctuations can be influenced in a favorable manner. This principle is partly known in reluctance motors, where the torque in the rotor is generated exclusively by the reluctance force and not to a significant extent by the Lorentz force.

In a preferred embodiment, the material of a carrier of the magnets (not the magnet material itself) is chosen to have the lowest possible electrical resistance. For example, the magnet carrier can be made of aluminum.

In a further advantageous embodiment, the drive device comprises a rotor coupled to the holding device and a stator, wherein either the rotor or the stator is made of or comprises a material having a high magnetic permeability, wherein said material preferably being selected from a group of materials containing iron, mu-metal (NiFe), nanocrystalline metals, and amorphous metals) and/or the permeability number of the material is greater than 200, preferably greater than 300.

If the tangential speed is not equal to an ideal rolling speed at the bar or stator, the opposing permanent magnets induce a voltage in the conductive carrier material and cause eddy currents. These brake or accelerate the rotational movement of a roller and push it in the direction of the ideal speed.

This idea is similar to the principle of an eddy current brake, i.e. here too the circumference of the roller is braked and thus the roller itself is set in rotation.

Particularly preferably, the apparatus has a cover for covering the magnets. This can, for example, consist of a material that is a good conductor of electricity in order to create the eddy current effect here. For example, the cover can be made of aluminum.

As mentioned, in a preferred embodiment, coils are inserted in at least one of the drive elements, i.e. the stator or the rotor and in particular in a fixed magnetic bar, which preferably point in the axial direction towards the rotor, i.e. the roller.

As long as the rotor rotates at an ideal speed and "rolls" along the bar as desired, only little voltage is induced in the coils. However, if a roller slips or oscillates at the rotational speed, then relatively much voltage is induced in the coils due to the large change in flux density.

The induced voltages are measured by an electronic control (for example PLC) and can be evaluated either in the coil or as a series connection of the coils.

The present invention is further directed to a method for treating containers, wherein the containers are transported by a transport apparatus along a predetermined transport path, and wherein the transport apparatus comprises at least one transport device for transporting the container, and wherein at least one container treatment apparatus treats the containers in a predetermined manner, wherein said transport device comprising a rotatable carrier on which a plurality of holding devices hold said (plurality of) containers.

In an embodiment according to the invention, these holding devices are moved relative to a carrier in such a way that a distance between two containers immediately following each other on the transport path is changed. Furthermore, the container treatment device treats the containers transported by the transport device.

In a further method according to the invention, the containers held by the holding devices are rotated at least temporarily and preferably during this treatment with respect to a longitudinal direction of the containers and in particular during the treatment, wherein a monitoring device particularly preferably monitors the rotational movement of the containers and in particular monitors it with respect to a rotational speed.

It is therefore also proposed on the process side that the treatment takes place during a rotation of the containers. Preferably, the containers are plastic preforms.

In a preferred method, the container treatment device treats an outer surface of the containers. In particular, the container treatment device sterilises the outer surface of the containers. Particularly preferably, a surface radiator is provided for this purpose, which directs radiation, in particular electron radiation, onto the outer surface of the containers. This surface radiator can be arranged on a housing of the apparatus in such a way that the radiation reaches the containers through an opening in the housing.

Particularly preferably, the container treatment device treats the containers while these containers are transported along a substantially straight transport path section. Alternatively, it may be a transport path section whose radius of curvature is substantially larger than a geometric radius of curvature that would result if all holding devices on the transport equipment were aligned in the same way. Particularly preferably, this radius of curvature is at least twice, preferably at least three times, preferably at least four times and preferably at least five times as large.

Particularly preferably, the containers are also treated with a second treatment device. In particular, an internal sterilisation is carried out as described above. For example, electron beam devices can be introduced into the containers.

Preferably, the containers are moved past the stationary treatment devices. In a further preferred method, the rotation of the containers arranged on the holding devices is transmitted by magnetic forces.

Preferably, the transmission of the rotational movement takes place in such a way that a rotational speed of the containers and/or plastic preforms is smoothed.

In a preferred method, the rotational movement of the containers is smoothed and/or vibration damping is performed by means of eddy currents.

The present invention further relates to an apparatus for treating plastic preforms, in particular for sterilising plastic preforms.

Such apparatus have been known from the state of the art for a long time. In this case, plastic preforms are fed through an entrance in a housing in which a treatment, in particular a sterilisation, is carried out. In these types of apparatus, transport devices are usually attached which transport the plastic preforms along a transport path. After treatment, the plastic preforms are removed via an outlet of the device.

However, the prior art has a disadvantage. In order to be able to remove defective plastic preforms or plastic preforms that do not meet certain requirements, which for example have not been sufficiently treated and in particular sterilised, the entire process would have to be stopped and the housing opened. However, opening the apparatus could re-contaminate plastic preforms that meet the requirements. Also, if the housing is opened, its cleanroom properties are lost and the housing must be sterilised again.

The present invention is therefore based on the object that plastic preforms or, more generally, containers can be removed without interrupting the operating process and/or opening the housing.

According to the invention, these objects are achieved by the subject matters of the independent claims. Advantageous embodiments and further developments are the subject of the subclaims.

An apparatus according to the invention for treating containers, in particular plastic containers and in particular plastic preforms, in particular for sterilising plastic preforms, has a housing which surrounds the apparatus, wherein the containers or plastic preforms being treated inside the housing. At least one transport device is provided inside this housing for transporting the plastic preforms along a predetermined transport path. The apparatus has an entrance through which the plastic preforms can be introduced into the housing and an exit through which the plastic preforms can be removed from the housing.

According to the invention, the apparatus comprises an airlock device and/or a removal device by means of which the plastic preforms can be removed from the housing.

In a further advantageous embodiment, the apparatus has holding devices for holding the plastic preforms. These can be holding mandrels that engage in the mouths of the plastic preforms.

It is noted that the present invention may also be combined with other aspects described within the scope of the present application, for example, the presence of exactly three transport devices within the housing, or the presence of a pitch distribution starwheel or the like.

In a further advantageous embodiment, the transport device has a rotatable carrier on which the holding devices are arranged. This can be a transport starwheel.

Advantageously, the transport device is a pitch distribution starwheel which is suitable for changing and, in particular, increasing the distance between successive plastic preforms. Instead of the pitch distribution starwheel, it would also be conceivable to use an elongated stator that changes the pitch of the plastic preforms.

Preferably, the plastic preforms are removable during an operation of the apparatus, in particular during a sterilisation operation, in particular also during a transport of the remaining plastic preforms.

In a further advantageous embodiment, the containers and in particular plastic preforms can be removed via a further outlet, which is preferably located between the inlet and the outlet. Particularly preferably, a further outlet is arranged closer to the outlet than to the inlet. In a further preferred embodiment, the apparatus has several transport devices and the further outlet is particularly preferably arranged in a region of the last of these transport devices.

In a further advantageous embodiment, the apparatus removes selected and/or defective plastic preforms. Preferably, the apparatus can remove damaged plastic preforms or those that have fallen off. In addition, containers and in particular plastic preforms that have been incorrectly sterilised can also be removed.

In a further advantageous embodiment, the apparatus has an inspection device for inspecting the containers and in particular the plastic preforms. In doing so, the containers and in particular the plastic preforms are inspected for defects and/or are examined as to whether they meet certain requirements. Preferably, this inspection device sends a signal to the airlock device as to whether a container and in particular a plastic preform should be removed.

In a further advantageous embodiment, the apparatus has a sterilisation device for sterilising the plastic preforms. In this case, an electron beam sterilisation device is particularly preferred.

Preferably, the apparatus has a container inner surface treatment device and/or a container outer surface treatment device. As mentioned above, the container outer surface treatment device is preferably designed as a surface radiator and in particular as an electron surface radiator.

In a further preferred embodiment, the container inner surface treatment device is designed as described above, i.e. it has, in particular, rod-like bodies which can be inserted into the plastic preforms and which sterilise the inner wall of the plastic preforms with electron beams.

In a further advantageous embodiment, a discharge starwheel is provided by means of which the plastic preforms can be discharged from the apparatus.

In a further advantageous embodiment, the housing surrounding the apparatus is an isolator. In this case, a clean room is preferably provided, which is particularly preferably kept under a positive pressure (e.g. sterile air). The housing and/or the housing walls are preferably designed to shield against radiation.

According to the invention, the clean room function can also be maintained when plastic preforms are removed through an airlock device.

Advantageously, the airlock device is separable and in particular separable from the housing. Thus, it is possible that an area of the entire apparatus or the electron beam module can be separated from the housing. In particular, this area and/or the airlock device can be separated without destroying the clean room properties. Preferably, this airlock device can also be separated during operation of the apparatus.

In a preferred embodiment, the airlock device is manually separable by an operator. The airlock device and/or said area is preferably separable in such a way that neither radiation nor gases produced during production can enter or leave the housing in a separation area or the sterility of the rest of the machine is endangered.

In a preferred embodiment, the apparatus has a transport device and, in particular, an outlet starwheel by means of which the containers and, in particular, plastic preforms are discharged from the apparatus. This transport device and/or the apparatus can have a radiation protection device which prevents radiation, in particular X-rays, from escaping from the housing.

During operation of the apparatus, it is possible that containers and in particular plastic preforms are guided into the area of the airlock device, in particular if this airlock device is not separated from the apparatus or is located on the apparatus or the housing.

In a further advantageous embodiment, the apparatus has a conveying device which conveys containers and, in particular, plastic preforms into the airlock device and, in particular, into the aforementioned separable part of the apparatus. Such a conveying device can, for example, have inclined surfaces which convey the containers or plastic preforms into the airlock.

The described procedure makes it possible to eject containers or plastic preforms during ongoing production or production does not have to be interrupted. In this way, the plastic preforms can be removed for further testing.

In a preferred embodiment, the airlock device is arranged on a wall of the housing and, in particular, on an opening in this wall via which plastic preforms can pass from the housing into the airlock device.

A movable wall element can be provided in this wall of the housing with which this opening can be closed.

In a further advantageous embodiment, a further transport device and preferably at least two further transport devices are arranged in the housing.

The present invention is further directed to a method for treating plastic preforms, in particular for sterilising plastic preforms. In this process, the plastic preforms are treated and, in particular, sterilised within a housing and are transported along a predetermined transport path by a transport device. The plastic preforms are introduced into the housing via an inlet and, at the end of an operation, are removed from the housing again via an outlet.

According to the invention, a predetermined proportion of the plastic preforms is removed from the housing via an airlock device.

In a further preferred method, the plastic preforms are treated and in particular sterilised with a sterilisation device. In this process, the plastic preforms are particularly preferably treated with a container inner surface treatment device and/or with a container outer surface treatment device and in particular sterilised.

Preferably, the airlock device is at least temporarily separated or removed from the housing.

In summary, the plastic preforms can be transported along a straight line past the treatment device. At this distance, the distance between the plastic preform or container and the treatment device, in particular a surface radiator, also remains essentially the same. Furthermore, the plastic preforms are preferably moved between the treatment device and a radiation shield. This radiation shield can consist of a specially selected material, for example tungsten.

The pitch distribution starwheel allows the plastic preforms to be moved past the treatment device or the surface radiator for a relatively long time. Preferably, the packing density of the plastic preforms can also be increased in front of the surface radiator.

The radiation shield (inside and/or outside the housing) preferably has a contour that prevents radiation from escaping from the housing or insulator. The pitch distribution starwheel allows the plastic preforms to follow the contour of the radiation shield. As mentioned above, a long stator with shuttles or a linear motor drive can also be selected instead of a pitch distribution starwheel.

The present invention further relates to a container treatment apparatus comprising a module for sterilisation with radiation and a rinser and a corresponding method.

In the beverage manufacturing industry, it has long been known that the containers to be filled are sterilised, especially before they are filled. It has proven advantageous not to sterilise the expanded containers first, but to sterilise the preforms before they are formed into containers, as the preforms are much smaller than the resulting containers.

The term "container" therefore also includes in particular a preform, especially a plastic preform.

One method of sterilisation used in the prior art is sterilisation using sterilising gases and in particular hydrogen peroxide. In order to reduce the use of chemicals in the sterilisation of containers, apparatus and methods are also known in the state of the art which sterilise the containers using other measures, such as ultraviolet radiation or electron beams.

For cleaning containers, it is also known to act upon the containers with a flowable medium, so that in particular dust and other impurities located in the containers are removed from the interior of the containers, in order to avoid contamination of the product during the subsequent filling process.

According to the current state of the art, a combination of the different cleaning methods often proves to be difficult.

The invention is therefore based on the object of providing an apparatus and a method by which the best possible cleaning and sterilisation result of the containers can be achieved.

A container treatment apparatus according to the invention, in particular a container sterilisation apparatus, has a plurality of transport devices for transporting a container along a predetermined transport path within a housing, wherein at least one of the transport devices is a container outer surface treatment device and at least one of the transport devices is a container inner surface treatment device, each having at least one holding device for holding at least one container during a container treatment and/or transport along the transport path.

According to the invention, the container outer surface treatment device and/or the container inner surface treatment device comprises at least one radiation source and the container treatment apparatus comprises according to the invention at least one application device which acts upon the container with a flowable medium, in particular ionised air.

In a preferred embodiment, the radiation source is an electron radiation source. Preferably, the container outer surface treatment device and the container inner surface treatment device each have a radiation source, preferably an electron radiation source. It is therefore proposed that radiation, and in particular electron radiation, is used for both container inner sterilisation and container outer sterilisation.

In a preferred embodiment, the container inner surface treatment device has a container inner surface application device. Advantageously, the container inner surface application device acts upon an inner surface of the container with electron radiation. Preferably, the container inner surface application device is insertable into the interior of the container to be sterilised, in particular through a mouth region. Advantageously, the container inner surface application device is suitable for emitting radiation, in particular electron radiation, inside the container for a predetermined period of time.

Preferably, at least one holding device is suitable and provided to hold the container during the container inner surface sterilisation. Advantageously, the container inner surface application device and/or the holding device are movable. Advantageously, the container inner surface application device and/or the holding device are also movable at least in a longitudinal direction of the container. Preferably, the container inner surface application device and/or the holding device are movable in a longitudinal direction of the container at least also during the container inner surface sterilisation. Advantageously, the container can be moved relative to the container inner surface application device in a longitudinal direction of the container at least temporarily at a relative movement speed during a predetermined period of time.

In a preferred embodiment, the container outer surface treatment device has a container outer surface application device. Advantageously, the container outer surface treatment device is always arranged outside the containers to be sterilised, for example laterally along a transport path of the containers. Preferably, the container outer surface treatment device is arranged stationary with respect to the transport path of the containers. In this way, the individual containers are guided past the container outer surface treatment device. Advantageously, the container outer surface application device has a radiation source whose exit window distributes the radiation evenly over a large area, in particular over the outer surface of the containers to be sterilised.

In an advantageous embodiment, the application device is preferably a so-called rinser or rinser unit. The flowable medium is preferably a gaseous medium, particularly preferably compressed air and in particular purified, prepared and/or sterilised compressed air. Advantageously, the flowable medium can also be a liquid medium. It is also conceivable that the flowable medium is a sterile medium, so that no further contamination of the containers is caused.

The combination of an application device with a container outer surface treatment device and/or a container inner surface treatment device has a particularly advantageous effect on the disinfection results and the log rates to be achieved. This applies in particular if the container outer surface treatment device and/or the container inner surface treatment device has a radiation source, in particular an electron radiation source.

In a preferred embodiment, the container treatment apparatus has a further transport device which transports the containers during the treatment process. This transport device is preferably a saw-tooth starwheel.

In a preferred embodiment, the application device has at least one rinser nozzle. Preferably, this can be a static or stationary nozzle. In a static arrangement of the rinser nozzle, the preforms are preferably moved away under the application device and thus cleaned. With such a stationary rinser nozzle, the containers, in particular the plastic preforms, are preferably transported in an upright position, i.e. with their mouths pointing upwards.

In a further preferred embodiment, the at least one rinser nozzle can be moved along with the containers at least temporarily during the transport of the containers. Compared to a stationary nozzle, a moving nozzle enables considerably longer process or rinsing times, which leads to better rinsing results overall.

In a further particularly preferred embodiment, the at least one rinser nozzle can be moved along with the containers and is inserted into a mouth area of the containers. By means of such a moving and inserting rinser nozzle, the highest cleaning results can be achieved, especially with very fine and light particles.

The nozzle position when inserting the rinsing nozzle into the containers is preferably controlled by a mechanical, hydraulic, pneumatic or similar device suitable for this purpose.

Preferably, the height of the nozzle head is detected at the start of the process, before the actual process and during the process. Preferably, the insertion depth of the nozzles in the container and preferably the mouth of the container is adjusted in a targeted manner in order to achieve and guarantee an optimal cleaning result, depending on the type of container.

Compared to static rinsing nozzles, the degree of cleaning of the containers can therefore be increased enormously with moving nozzles, as a container is cleaned by a nozzle for a longer period of time. Both when using a static nozzle and when using a moving nozzle, the cleaning of the containers is preferably carried out during the transport of the containers.

Preferably, if it is a moving nozzle or a moving and inserting nozzle, the containers are transported overhead, i.e. with the mouth downwards.

In a preferred embodiment, the application device is arranged outside the housing. This allows the housing to be as small as possible.

In a further preferred embodiment, the application device is arranged along the transport path upstream of the container outer surface treatment device and/or the container inner surface treatment device. Particularly preferably, the application device is arranged both upstream of the container outer surface treatment device and of the container inner surface treatment device. Preferably, a container is thus first acted upon by the application device with a flowable medium before it is subsequently treated, in particular sterilised, by the container outer surface treatment device and the container inner surface treatment device. This is particularly advantageous because the container can be pre-cleaned by the application device before the outer and/or inner surface of the container is sterilised.

Preferably, the application device is not arranged directly in front of the container outer surface treatment device and/or the container inner surface treatment device. Advantageously, both transport devices and further container treatment devices can be provided between the application device and the container outer surface treatment device and/or the container inner surface treatment device.

In an advantageous embodiment, the container treatment apparatus has a heating apparatus for heating the container. Preferably, the heating apparatus has at least one heating device, particularly preferably several heating devices. Advantageously, the heating device can be a radiation source, for example for infrared or microwave radiation.

Preferably, the heating apparatus is arranged along the transport path upstream of the container outer surface treatment device and/or the container inner surface treatment device.

Particularly preferably, the heating apparatus is arranged upstream of both the container outer surface treatment device and the container inner surface treatment device.

Preferably, a container is thus first heated by the heating apparatus before it is treated, in particular sterilised, by the container outer surface treatment device and the container inner surface treatment device.

In a preferred embodiment, the application device is arranged along the transport path upstream of the heating apparatus and/or the application device is arranged directly upstream of the heating apparatus. Particularly preferably, the application device is integrated into the heating apparatus. Preferably, a container is thus first charged with a flowable medium by the application device before it is subsequently heated by the heating apparatus. This sequence is particularly advantageous if the flowable medium is a liquid medium. In this way, it can evaporate particularly well due to the heating of the container in the heating apparatus.

In a preferred embodiment, the container treatment apparatus has a further transport device which is arranged between the heating apparatus and the container outer surface treatment device and/or the container inner surface treatment device. Advantageously, this is exactly one transport device which is arranged between the heating apparatus and the container outer surface treatment device and/or the container inner surface treatment device. Whether this transport device is arranged between the heating device and the container outer surface treatment device or between the heating device and the container inner surface treatment device depends on whether the container outer surface treatment device or the container inner surface treatment device is arranged upstream in the transport direction.

A particularly preferred embodiment is one in which an application device is arranged first in the direction of transport, followed by a heating apparatus, then a transport device, in particular a single transport device, and then a container outer surface treatment device and a container inner surface treatment device. Advantageously, the application device is thus arranged close to the container outer surface treatment device and the container inner surface treatment device. This minimizes the possibility of re-contamination of the container between the application device and the container outer surface treatment device and the container inner surface treatment device. This enables even better disinfection results to be achieved.

Preferably, the transport device, which is arranged between the heating apparatus and the container outer surface treatment device or the container inner surface treatment device, is arranged outside the housing.

Preferably, at most two further transport devices, particularly preferably only one further transport device, are arranged inside the housing in addition to the container outer surface treatment device and the container inner surface treatment device.

In addition to the advantages already mentioned, this advantageously leads to greater geometric flexibility. In the prior art, five stars are usually arranged in the housing, in particular two treatment carousels and three transfer starwheels. In the prior art, this leads to the fact that essentially only one spatial arrangement of the heating apparatus to the forming device is possible, in which the heating apparatus and the forming device are arranged essentially at a 90° angle.

A 0° set-up of the heating apparatus and forming device cannot be realised in the state of the art. This can lead to considerable restrictions in layout planning on the part of the customer. Likewise, in the known prior art design, it is difficult to load an application device that is integrated into the inlet of the heating apparatus, as collisions would occur due to a lack of available installation space.

The reduction of the transport devices in the housing simplifies the positioning of the transport devices or the container outer surface treatment device and the container inner surface treatment device in relation to each other and thus results in a higher degree of freedom in the arrangement of these. In this way, an arrangement of the heating apparatus and the forming device can be advantageously realised in a 0° position. All other angular positions between 0° and 90° are also conceivable.

This also creates plenty of installation space to equip an integrated application device in the heating apparatus.

In an advantageous embodiment, the transport device between the heating apparatus and the container outer surface treatment device or the container inner surface treatment device is a pitch distribution starwheel. This in turn allows a more clever arrangement of the individual upstream and downstream machine modules.

The present invention is further directed to a method for treating and in particular sterilising containers, in particular plastic preforms. In this process, a container is transported along a predetermined transport path, which lies at least partially within a housing, by several transport devices, wherein the container is treated and, in particular, sterilised on its outer surface at at least one transport device, wherein the container is treated and, in particular, sterilised on its inner surface at at least one transport device, and wherein the container is held by holding devices during container treatment and/or transport along the transport path.

According to the invention, the outer surface of the container and/or the inner surface of the container is acted upon with radiation, in particular electron radiation, and/or the container is acted upon with a flowable medium by an application device.

In particular, the described apparatus is designed and intended for carrying out this described method, i.e. all the features described for the apparatus described above are also disclosed for the method described here and vice versa.

In an advantageous method, the container is acted upon with a flowable medium before the outer surface of the container and/or the inner surface of the container is treated with radiation. In particular, the container is preferably first pre-cleaned with a flowable medium and then sterilised with electron radiation. In this way, particularly good disinfection results can be achieved.

Preferably, the container is acted upon with a flowable medium before the container is heated. This allows any residues of the flowable medium to evaporate better.

Advantageously, the container is transferred directly from the application device to the heating apparatus. On the one hand, this advantageously reduces the risk of contamination, as the shortest possible path between the application device and the container outer surface treatment device and the container inner surface treatment device is realised. On the other hand, it is possible to integrate the application device into the heating apparatus.

The present invention is in particular directed to an improvement in the transport of containers. In the beverage manufacturing industry, it has been known for a long time that the manufacturing process of containers comprises a plurality of container treatment devices and transport devices. It is also known that linear and/or rotating transport devices are used to transport the containers.

In the state of the art, a plurality of holding devices are known which hold the containers during treatment and/or transport. For example, such holding devices are known which grip the containers below the support ring, wherein the latter rests loosely on the holding device. Furthermore, such holding devices are known which grip the containers in the area of a mouthpiece groove (narrow area between closure ring and support ring) or such holding devices which grip the containers in the area of the mouth, for example by means of holding mandrels.

The present invention is described herein with reference to the sterilisation of containers, which is also a particularly preferred application of the invention. However, it is noted that the invention is also applicable to other devices in which holding devices are used to hold containers.

Within the scope of the known manufacturing processes of containers, these must be repeatedly transferred between two transport devices and/or container treatment devices, more precisely between their holding devices, for example between two transport starwheels.

For this purpose, the holding device (clamp) of one transport starwheel opens at the overlap point and releases the container, while the holding device of the other transport starwheel closes and thus clamps or at least encloses the container and transports it further. For this, it is necessary that the container is gripped at different positions by the holding device (clamps). A distinction is made between holding devices (clamps) where the support ring rests and the container is clamped slightly below the diameter and holding devices (clamps) that grip between the closure ring and the support ring, the so-called mouthpiece groove. The distance between the lower edge of the support ring and the mouthpiece groove is very small, which means that there is very little space between the holding devices (pairs of clamps) during transfer, which greatly limits the design of the holding devices (clamps).

The holding devices known in the prior art for gripping the container underneath the support ring have the disadvantage that the support ring of the container only rests and the alignment is not ensured by the closure ring and the support ring as in the case of a holding device with a mouthpiece groove clamp. Especially when using containers with a smaller support ring or similar, the container may not sit straight in the holding device.

In addition to possible problems during the transfer between two transport devices, problems can also occur during the treatment of the containers, for example during internal sterilisation by electron beams, in which a beam tube is inserted into the container. If the container is at an angle, the tube collides and the sterility of the container cannot be guaranteed, which means that it has to be removed from the production chain. In addition, a collision can also destroy the beam tube and thus the entire electron beam emitter.

The present invention is therefore based on the object of providing suitable holding devices which simultaneously ensure stable gripping of the containers and at the same time guarantee safe transfer of the containers between two transport devices. According to the invention, this object is achieved by an apparatus and a method according to the independent claims. Advantageous embodiments and further developments are the subject of the subclaims.

A container treatment apparatus according to the invention, in particular a container sterilisation device, has a transport device for transporting a container along a predetermined transport path, wherein the transport device having at least one container treatment device, preferably a container outer surface treatment device and/or particularly preferably a container inner surface treatment device, wherein the container, in particular a plastic preform or a plastic bottle, having a head region with a mouth, a closure ring, a mouthpiece groove and a support ring.

In addition, the transport device comprises at least one first transport device and at least one second transport device, wherein the first transport device comprises at least one first holding device for holding a container and the second transport device comprises at least one second holding device for holding a container during container treatment and/or transport along the transport path.

According to the invention, the support ring of the container, in particular the outer surface of the support ring and/or preferably the underside of the support ring and/or particularly preferably the upper side of the support ring, is through the at least one first holding device and the mouthpiece groove of the container, in particular directly abutting the underside of the closure ring, graspable by the at least one second holding device.

The proposed holding devices offer the advantage that a container held in this way is fixed, i.e. the support ring or the mouthpiece groove is clamped in place, and thus lateral tilting or an oblique arrangement of the container in the holding device can be effectively avoided.

Preferably, a container treatment apparatus, in particular a container sterilisation device, comprises at least one container treatment device, particularly preferably a plurality of container treatment devices. Preferably, the at least one container treatment device is selected from a group of container treatment devices comprising a container outer surface treatment device (in particular a container outer surface sterilisation device), a container inner surface treatment device (in particular a container inner surface sterilisation device), a heating device, a forming device, a filling device, a closing device, an inspection device and the like.

Preferably, the transport apparatus comprises at least one first transport device and at least one second transport device. In an advantageous embodiment, the at least one first and/or second transport device has a rotatable carrier and is preferably a transport starwheel.

However, it would also be possible here to use a long stator on which a plurality of shuttles are arranged, as described above.

In a further advantageous embodiment, the at least one first and/or second transport device is associated with a container treatment device which is suitable and intended for treating the container during transport. Particularly preferably, the at least one first and/or second transport device is part of a container treatment device.

Preferably, the container to be treated is a plastic bottle and particularly preferably a plastic preform. The container preferably has a head portion comprising a mouth, an (external) thread, a closure ring, a mouthpiece groove and a support ring.

Preferably, the closure ring has a smaller diameter than the support ring. Particularly preferably, the container has a (so-called) mouthpiece groove between the closure ring and the support ring.

Preferably, a first transport device has at least one first holding device for holding a container and particularly preferably a plurality of such holding devices. Preferably, a second transport device has at least one second holding device for holding a container and particularly preferably a plurality of such holding devices. Particularly preferably, the first and the second holding device differ by an area of the container to be gripped and/or by contact or receiving areas which are suitable and intended for gripping this area of the container.

Preferably, the at least one first and/or second holding device is suitable and intended to (firmly) grip a container and is capable of stabilising the container, and particularly preferably capable of preventing lateral tilting of the container. Preferably, the at least one first and/or second holding device at least partially encloses the container, in particular a part of the head area of the container.

In an advantageous embodiment, the at least one first and/or the at least one second holding device is designed in a clamp-like manner.

Preferably, the at least first and/or second holding device is constructed in two parts, wherein preferably two holding elements or clamp elements (or clamp arms) are movably arranged on a common pivot axis. Preferably, the at least first and/or second holding device can be operated in a closed or gripping position and/or in an open position, wherein preferably the distance between the two ends of the holding elements or clamp elements in this position is greater than the diameter of the container and/or an outer diameter of a mouth region of the container.

In particular, the at least one first holding device is suitable and intended to grip the support ring of the container. In particular, the at least one second holding device is suitable and intended to grasp the mouthpiece groove of the container. In an advantageous embodiment, the first holding device comprises a holding groove for grasping the support ring of the container. Preferably, the at least one first holding device grasps the underside of the support ring of the container at least in sections and/or the outer side of the support ring at least in sections and/or the upper side of the support ring at least in sections. Particularly preferably, the at least one first holding device encloses the underside, the top side and the outer side of the support ring at least in sections. This offers the advantage that the container is (optimally) fixed in the at least one first holding device and is secured against lateral tilting.

Preferably, the at least one second holding device is suitable and intended to grip the container in the area of the mouthpiece groove. Particularly preferably, the upper region of the mouthpiece groove is gripped, wherein the at least one second holding device resting against the underside of the closure ring of the container.

In an advantageous embodiment, the at least one first transport device and the at least one second transport device are arranged adjacent to each other within the container treatment apparatus.

In an advantageous embodiment, the container treatment apparatus has at least one transfer area in which the container can be transferred between the at least one first transport device and the at least one second transport device.

Preferably, the transfer area is designed in such a way that the at least one first and the at least one second transport device run tangentially to each other. Particularly preferably, the transport path of the at least one first holding device arranged on the at least one first transport device and the transport path of the at least one second holding device arranged on the at least one second transport device overlap.

In an advantageous embodiment, the at least one first holding device and the at least one second holding device can be arranged in the transfer area overlapping each other and/or substantially perpendicular to a longitudinal axis of the container.

This means that in the transfer area where the transport paths of the at least one first and second holding devices intersect, the two holding devices are (essentially) parallel to each other and (essentially) perpendicular to the longitudinal axis of the container. Since the two holding devices engage both the support ring and the directly adjacent area of the mouthpiece groove, the two holding devices come very close to each other, which would not be possible with the holding devices currently used in the state of the art.

Particularly preferably, sections of the first holding device and the second holding device overlap in an area of the transfer of the containers.

In an advantageous embodiment, the end of the at least one first and the at least one second holding device facing the container is tapered, in particular complementary to each other.

This offers the advantage that the first and second holding devices can be placed very close to each other without touching. By using holding devices according to the present invention, it is possible to transfer a container between two transport devices, both of which grip the container firmly and protect the container against lateral tilting.

In the prior art, such a transfer (between a transport device with a holding device that grips the support ring and a transport device with a holding device that grips the mouthpiece groove) requires an additional transport device, for example another transport starwheel, which grips another area of the container, for example below the support ring.

The use of the proposed holding devices offers the advantage that a further transport starwheel can be dispensed with and thus the technical effort and the spatial expansion of the system can be significantly reduced.

The present invention is further directed to a method for treating containers. The proposed method may have all the features described in connection with the above-described container treatment apparatus, individually or in combination with one another, and/or carry them out.

Furthermore, the present invention is directed to a method for treating containers with a container treatment apparatus, in particular with a container sterilisation device. The container treatment apparatus comprises a transport apparatus which transports a container along a predetermined transport path, wherein the transport device comprises at least one container treatment device and the container comprises a head portion with a mouth, a closure ring, a mouthpiece groove and a support ring. The transport apparatus comprises at least one first transport device and at least one second transport device, wherein the first transport device comprises at least one first holding device for holding a container and the second transport device comprises at least one second holding device for holding a container during container treatment and/or transport along the transport path.

According to the invention, the at least one first holding device grips the support ring of the container, in particular the outer surface of the support ring and/or preferably the underside of the support ring and/or particularly preferably the upper side of the support ring, and the at least one second holding device grips the mouthpiece groove, in particular directly on the underside of the closure ring of the container.

The proposed method offers the advantage that both the first and the second holding device enable a firm grip of the container and at the same time offer protection against lateral tilting.

In an advantageous embodiment, the transfer of the container between the at least one first transport device and the at least one second transport device takes place in a transfer area, wherein the at least one first holding device and the at least one second holding device are arranged to overlap during the transfer. In particular, the first and second holding devices are arranged in a direction perpendicular to the transport path of the containers (in particular overlapping).

In a preferred method, at the time of transfer, the at least one first holding device and the at least one second holding device are arranged directly above each other, while the container is held by one of the two holding devices.

In an advantageous embodiment, the transfer of the container between the at least one first transport device and the at least one second transport device is synchronised and/or takes place without the at least one first holding device and the at least one second holding device touching each other.

Preferably, the gripping of the at least one first holding device or the at least one second holding device and the opening (release) of the at least one second holding device or the at least one first holding device take place simultaneously and preferably synchronised with each other. Particularly preferably, the transfer of the container (gripping or opening) is synchronised with the movement of the at least one first transport device and/or the at least one second transport device.

Furthermore, the present invention is directed to a holding arrangement for holding a container during a container treatment and/or a transport along a predetermined transport path, in particular with at least one first and with at least one second transport device, in particular in a transfer area between the at least one first and the at least one second transport device.

The holding arrangement comprises at least one first holding device and at least one second holding device, wherein preferably the at least one first holding device is associated with the at least one first transport device and the at least one second holding device is associated with the at least one second transport device, wherein the at least one first and the at least one second holding device each comprise at least two holding elements, preferably clamp elements, which are suitable and intended for gripping a head region of a container.

The head portion of the container preferably has a mouth, an optional closure ring, a mouthpiece groove and a support ring. The at least two holding elements are each pivotally mounted about a common pivot axis and are suitable and intended to be arranged in a position gripping the container or in a position releasing the container.

According to the invention, the at least two holding elements each have a closing region which faces the container to be held and is tapered, wherein the at least one first and the at least one second holding device can be arranged in an overlapping manner.

Preferably, the container is transferred from the at least one first transport device to the at least one second transport device or in reverse order in a transfer position in which the at least one first and the at least one second holding device are arranged directly above one another (overlapping). Preferably, in this transfer position, the at least one first holding device and the at least one second holding device overlap such that the tapered region of the holding elements of one holding device overlap with a non-tapered region of the other holding device. Particularly preferably, the at least one first and the at least one second holding device, in particular their holding elements, never touch each other.

In an advantageous embodiment, the tapered closing portions of the holding elements of the at least one first holding device and the at least one second holding device face each other and are complementary to each other.

In an advantageous embodiment, the at least one first and the at least one second holding device are identical in construction and can preferably be arranged on the at least one first transport device and/or the at least one second transport device and, particularly preferably, can be arranged in two different positions. The two positions differ formally by being mirrored on a horizontal plane. Preferably, the tapered area of the holding elements can thus point either upwards or downwards.

Preferably, the at least one first and the at least one second holding device, in particular their holding elements (clamps), are designed in such a way that both a protruding part of the container, in particular the support ring of the container, can be gripped and a flat section of the container, in particular the mouthpiece groove, can preferably be gripped directly below the closure ring.

BRIEF DESCRIPTION OF THE DRAWINGS

Further advantages and embodiments can be seen in the attached drawings.

In the drawings:

FIG. 4 shows a schematic representation of an exemplary profile of the displacement of a holding device and/or a container along the height direction on a container surface treatment device;

FIG. 17 shows an illustration of the generation of rotational movements of the holding device;

FIG. 18 shows a representation for the magnetic transmission of rotational movements in a first embodiment;

FIG. 19 shows an illustration for the magnetic transmission of rotational movements in a second embodiment;

FIG. 20 shows a representation for the magnetic transmission of rotational movements in a third embodiment;

FIG. 21 shows a representation for the magnetic transmission of rotational movements in a fourth embodiment;

FIG. 22 shows a representation for the magnetic transmission of rotational movements in a fourth embodiment;

FIG. 23 shows an illustration of a relationship between a rotational speed and a generation of eddy currents;

DETAILED DESCRIPTION OF THE INVENTION

Figure 1:
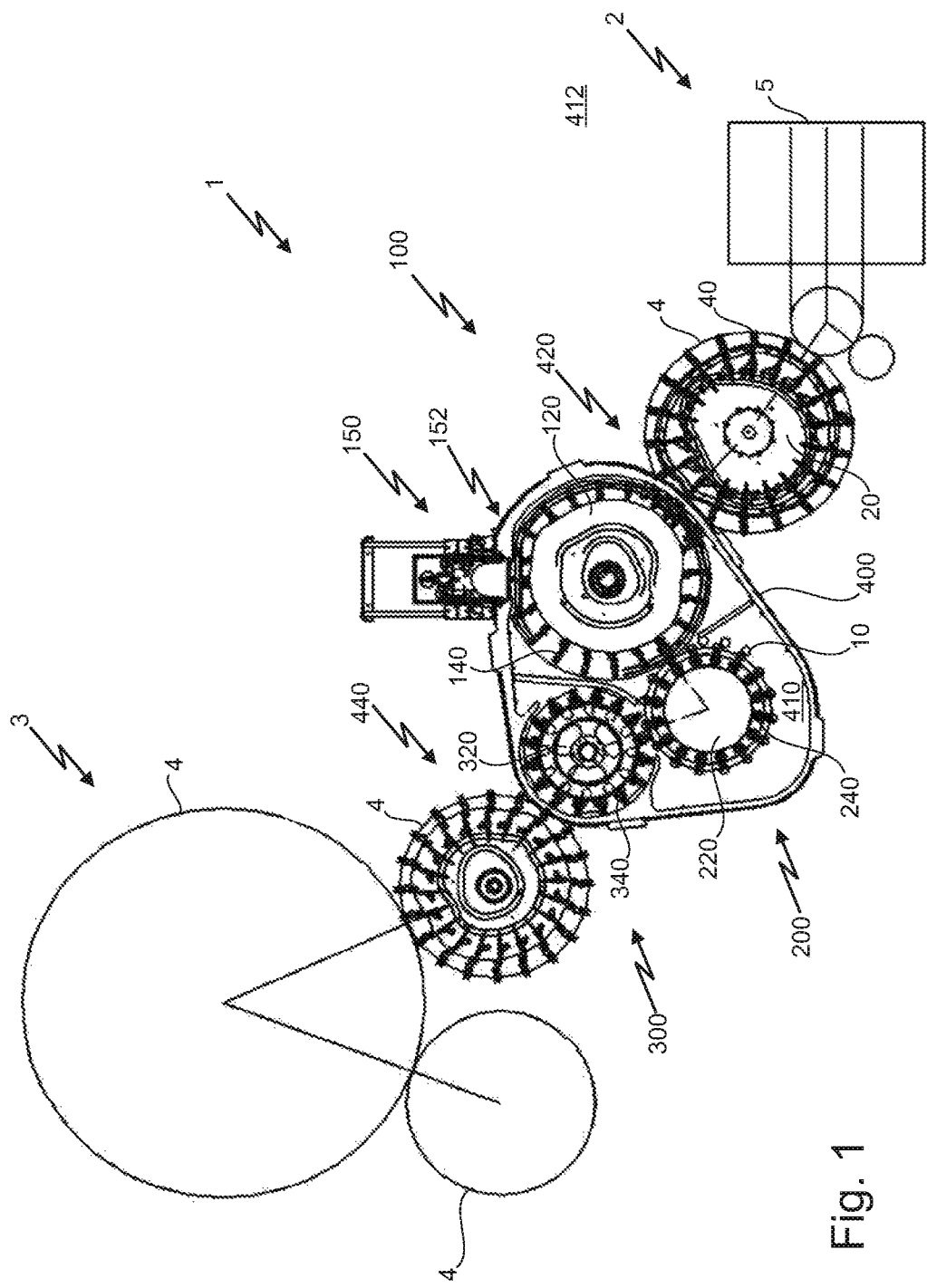
FIG. 1 shows a schematic view of a container treatment device in an exemplary embodiment.

FIG. 1 shows a schematic view of a container treatment device 1 in an exemplary embodiment. The container treatment device 1 shown, which in the example shown is a container sterilisation device, has several transport devices 100, 200, 300 for transporting a container 10 along a transport path within a housing 400, which is not highlighted in this illustration. One of these transport devices 100, 200, 300 is a container outer surface treatment device 100 and another is a container inner surface treatment device 200, each comprising a plurality of holding devices 140, 240 for holding at least one container 10 during container treatment and/or transport along the transport path.

At least one holding element 140 of the container outer surface treatment device 100 can be brought at least temporarily into the region of an opening 420 of the housing wall 400. This enables this holding element 140 to receive a container from a space 412 outside the housing 400 from a transport device 4 arranged there upstream with respect to the transport path. This embodiment makes it possible to dispense with an additional transport device inside the housing, which picks up the container from outside and forwards it to the container outer surface treatment device 100.

In the embodiment shown, the transport device 4 is arranged downstream of a heating device 2 comprising at least one heating device 5 such as an oven or a (for example infrared or microwave) radiation source. The transport device 4 has a plurality of holding elements 40 for holding the containers 10, which are arranged together on a rotatable carrier 20.

Part of the container outer surface treatment device 100 shown is a container outer surface application device 150, which in the example shown is a radiation source 150. However, it would also be conceivable to design it as a nozzle or nozzle arrangement by means of which a fluid medium such as a sterilisation solution or a sterilising gas is applied to the container surface to be sterilised.

In the container outer surface treatment device 100, the containers are transported past the container outer surface application device 150 by the holding elements 140 in a container outer surface application area 152. During this transport, they are acted upon with the sterilising medium—in this case sterilising radiation. Advantageously, the containers 10 are not only moved along the transport path, but are also moved in at least one further direction, as described elsewhere. This movement may comprise a rotation (about a longitudinal container axis and/or a transverse container axis) and/or a displacement perpendicular to the drawing plane (i.e. in height direction H). Such individual movement of the container to be treated makes it possible to treat all (outer) surfaces to be sterilised with a single container outer surface application device 150. Permanent shadowing of individual (outer) surfaces of the container 10 by other sections of the same container can be avoided.

In the embodiment shown in FIG. 1, a container 10 is transferred directly to a container inner surface treatment device 200 after treatment by the container outer surface treatment device 100. This also comprises a plurality of holding devices 240 which are arranged on a rotating carrier 220. A container inner surface application device is also provided. The container inner surface application device is not clearly visible in the depiction shown, as it is designed as a plurality of beam fingers each overlapping with a position for receiving a container 10. Each holding element 240 is thus associated with one such beam finger. During rotation of the carrier 220, the containers are moved relative to the beam finger associated with the holding element 240 occupied by that container 10. This movement takes place in a section between the pick-up of a container 10 by the container inner surface treatment device 200 and the delivery to a transport device 300 following along the transport path.

Preferably, this transport device 300 is a transport starwheel 300 with a rotatable carrier 320 and a plurality of holding elements 340 arranged thereon. This transport starwheel 300 receives the containers 10 treated by the container inner surface treatment device 200 and transfers them to a further transport device 4 arranged outside this housing 400. Preferably, the further transport also takes place under conditions which prevent contamination of the containers 10 treated by the container treatment device 1, for example in a clean room.

As shown in the example shown in FIG. 1, the area 410 enclosed by the housing 400 is particularly small, which can be justified, among other things, by the fact that there is only one further transport device 300 in addition to the container outer surface treatment device 100 and the container inner surface treatment device 200 within the housing 400.

As a further treatment of the containers downstream of the treatment in the container treatment apparatus 1, their forming into other containers 10, such as bottles, for example, can be carried out by a forming device 3, which is only indicated schematically. In addition or as an alternative, the containers 10 treated by the container treatment device 1 could be filled (and possibly closed).

Figure 2:
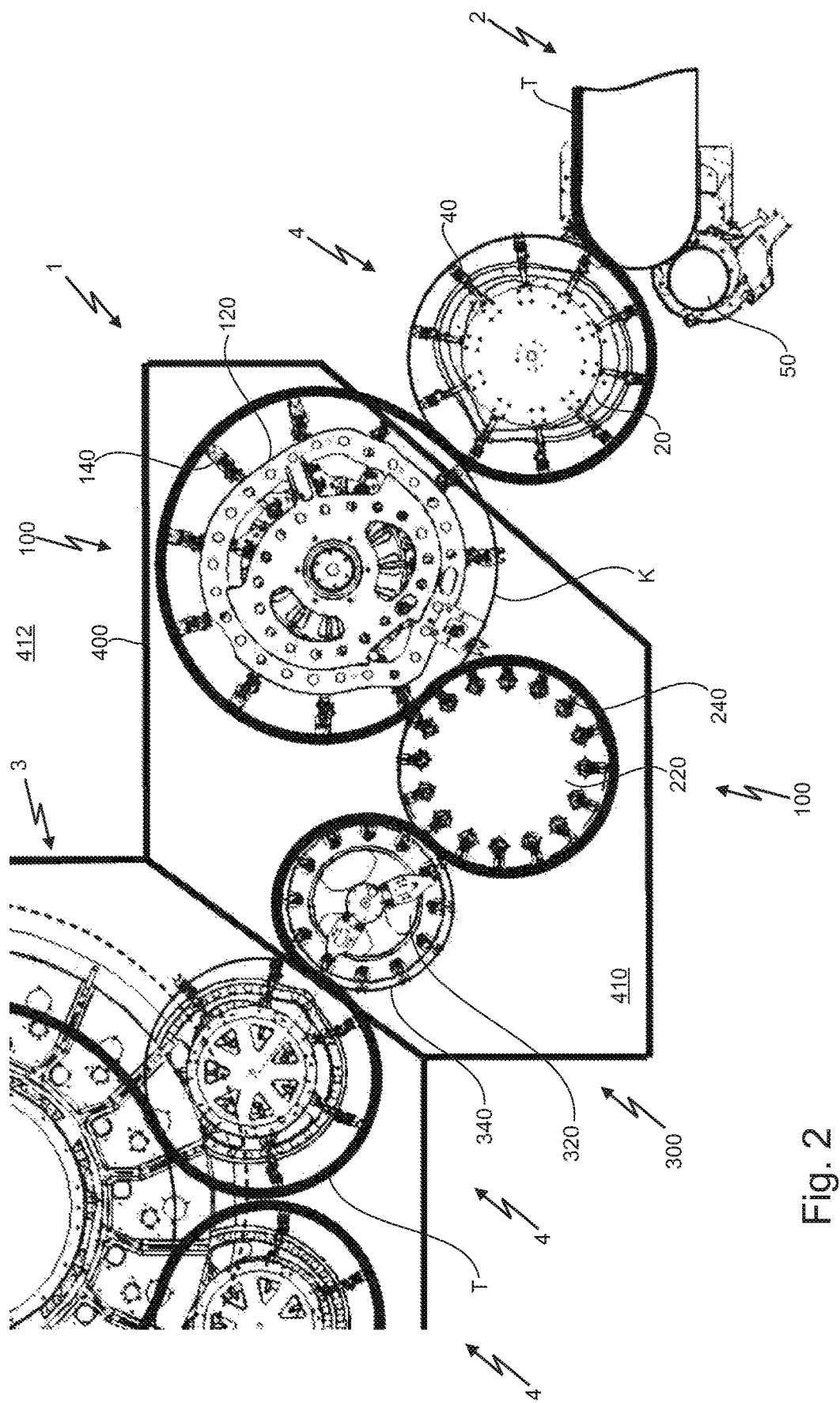
FIG. 2 shows a further schematic view of a container treatment device in a further exemplary embodiment with a vertical projection of a transport path.

FIG. 2 shows a further schematic view of a container treatment device 1 in a further exemplary embodiment. Unlike in FIG. 1, a transport path T is shown along which the containers 10 (not shown in this figure) are guided during their transport. The transport path T is shown in a vertical projection. Displacements of the containers during transport in the height direction H, perpendicular to the drawing plane (and thus also to the projection of the transport path), are therefore not visible in this illustration.

In the embodiment example shown, the section of the transport path T shown extends from a heating apparatus 2 via a transport device 4 into the treatment device 1 and from this via a further transport device 4 first to a forming device 3 and then further via a further transport device 4 for discharging the containers from the forming device 3. Along the transport path, a container is guided by holding devices 40, 140, 240, 340, which are each arranged on rotatable carriers 20, 120, 220, 320. The distance between two containers 10 or holding devices 40, 140, 240, 340 directly following each other along the transport path can be changed at least once, preferably several times. In particular, this is preferred in the area of an application device (not shown in detail in FIG. 2) and/or in the area of the passage through a wall of the housing 400, since the treatment time can be extended in the case of a slowed movement along the transport direction in these areas, or the window in the housing wall can be made smaller, in each case at the same rotational speed of the carrier. Details of this are described elsewhere.

In the embodiment shown in FIG. 2, exactly three transport devices 100, 200 and 300 are also arranged inside the housing 400, namely the container outer surface treatment device 100, the container inner surface treatment device 200 and a transport starwheel 300. Unlike in FIG. 1, the holding elements 140 of the container outer surface treatment device 100 are designed as externally gripping clamps 140 and not as mandrels. The design of the holding elements 140 can be adapted to the respective requirements. Preferred designs of the holding elements 140 of the container outer surface treatment device 100 are also described in more detail elsewhere. As can also be seen from FIG. 2, it may be possible for the holding elements 140 of the container outer surface treatment device 100 to be arranged, at least temporarily and in sections, outside the housing 400 in the environment 412 of the housing 400 in order to receive a container outside the housing 400 and then introduce it into the interior 410 of the housing.

Figure 3:
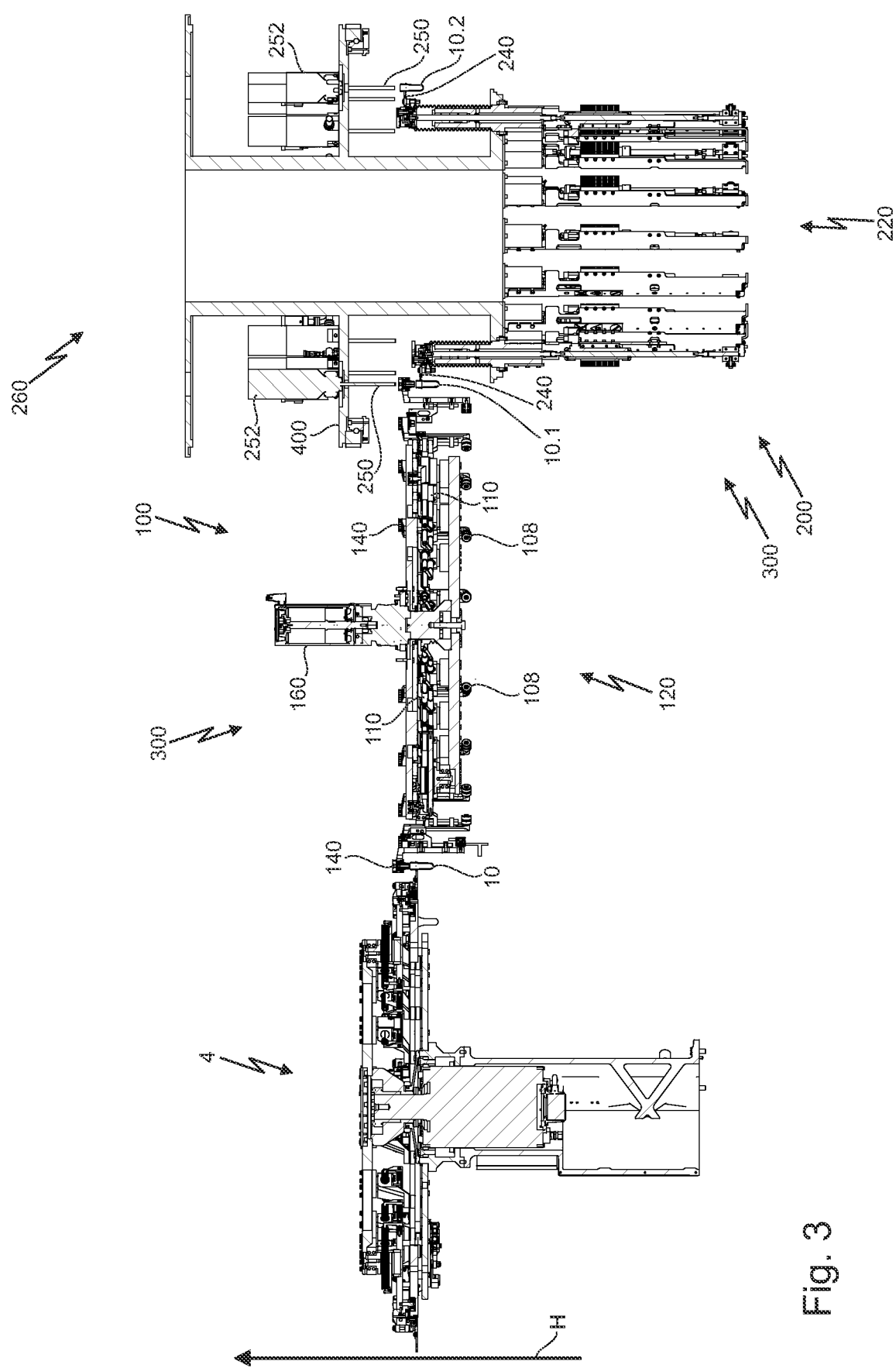
FIG. 3 shows a schematic representation of parts of two container surface treatment devices.

FIG. 3 shows a schematic representation of parts of transport devices 4, 100, 200, 300 between which a container 10 is transferred during its movement along the transport path. In the example shown, the transport devices 300 are a container outer surface treatment device 100 and a container inner surface treatment device 200. The container outer surface application device or radiation source of the container outer surface treatment device 100 is not shown in this illustration. The transport device 4 is a transport device arranged outside the housing (not shown), which transfers the containers to the container outer surface treatment device 100. This transport device 4 is not discussed in detail in the description of the illustration according to FIG. 3.

The drive devices 160 and 260 of the two container surface treatment devices 100, 200 (arranged inside the housing not shown) are arranged on the side opposite the drive device 6 of the transport device 4 with respect to the transport path of the containers 10 not shown. Thus, the drive device 160 of the container outer surface treatment device 100 and the drive device 260 of the container inner surface treatment device 200 are arranged above the transport path and the drive device 6 of the transport device 4 is arranged below the transport path. Preferably, they are located outside the housing 400, which is only shown in sections, so that they can be serviced without having to open the housing 400.

The "suspended" arrangement of the carrier 120 of the container outer surface treatment device 100 with the holding devices 140 arranged thereon on the drive device makes it possible to provide a comparatively large free space within the housing not shown below the carrier 120. For example, a control cam, which is not shown, can be arranged in this space, along which guide rollers 108 of the container outer surface treatment device 100 can roll. The space described above is particularly advantageous in order to be able to obtain easy access to the control cam and to be able to adjust it. Likewise, when changing the containers 10 to be treated, for example, it would be conceivable to remove a control cam unit from the housing and replace it with another control cam unit. Since no other components of the container outer surface treatment device 100 are permanently arranged in the area of the control cam unit below the carrier, such a control cam unit can be removed without having to disassemble it. This allows for quick changeover, especially when repeatedly switching between several containers. The respective control cam units could then be used immediately. A new adjustment to the container to be treated can be omitted—except for a possibly necessary fine adjustment.

In addition to the guide rollers 108, which, as described above, enable displacement of the holding device 140 and thus also of the containers 10 guided by it in sections in the vertical direction, i.e. along the height direction H, the container outer surface treatment device 100 also comprises a displacement mechanism 110, by means of which it is possible to displace a single holding device 140 perpendicularly to the height direction H. This displacement can comprise, for example, a displacement in the circumferential direction or a displacement in the radial direction with respect to the carrier 120. Of course, displacements having both a component in the circumferential direction and one in the radial direction are also conceivable and advantageous in some applications. In addition to this and independently of this, displacement along the horizontal direction H as described above is of course also possible, for example due to the interaction of the guide rollers 108 with the cam. In particular, combinations of displacements in at least two directions in the region of the (not shown) container outer surface application device 150 are advantageous in order to be able to guide a container 10 as linearly as possible at a defined distance along the container outer surface application device 150, despite the curvature of the circumferential path of the rotating carrier 120. If necessary, a further movement of the container is possible during this guidance, for example a rotation about a horizontal (tilting) or vertical (rotating) axis in order to be able to avoid permanent shadowing of certain surfaces by other parts of the container.

The container inner surface treatment device 200 is also a transport device 300, since the container is also transported along the transport path during treatment by the container inner surface treatment device 200. For this purpose, a container 10 is first taken over by the upstream transport device 300, in this case the container outer surface treatment device 100. This is done at a first height level. This low height level is necessary because an internally gripping holding device 140 of the container outer surface treatment device 100 is arranged between the beam finger 250 of the container inner surface treatment device 200 and the container.

In the example shown, the container 10 to be taken over is picked up by the container inner surface treatment device 200, more precisely by one of its holding devices 240, and then lowered to a lower height level. This is advantageous for removing the container from the internal gripping holding device 140 of the container outer surface treatment device 100. Alternatively or additionally, it would also be conceivable to raise the holding device 140 of the container outer surface treatment device 100, wherein the space available for this is limited by the beam finger 250.

After the container 10 has been withdrawn by the holding devices 240 of the container inner surface treatment device 200, it is at a lower height level as shown for the container 10.1. Subsequently, the container 10 is raised again, thereby moving relative to a container inner surface application device 250, preferably a beam finger 250. The relative movement takes place in such a way that the beam finger 250 projects at least in sections into the interior of the container 10. This enables the inner surfaces of the container 10 to be acted upon from a short distance, which is particularly efficient.

Preferably, the relative movement between the container 10 and the beam finger 250 is effected by a movement of the container towards the beam finger 250. In this case, the beam finger 250 or the container inner surface application device 250 can remain unchanged in position with respect to the carrier 220. This has the advantage that only the comparatively light and inexpensive container has to be moved and not the sensitive beam finger 250 with the radiation generating device 252 and possibly existing connections and/or supply lines. This radiation generating device 252 and any connections and/or supply lines that may be present are preferably—as shown in the example shown—located outside the housing 400, which is only shown in sections, in order to enable maintenance even when the housing is closed. The movement of a container 10 or a holding device 240 during a rotation of the carrier 220 of the container inner surface treatment device 200 is described in detail in connection with FIG. 4.

The delivery of the treated container 10.2 to a transport device not shown following along the transport path preferably takes place immediately after the beam finger 250 has completely left the container 10.2. A lowering of the container 10.2 to the first height level at which the pick-up of the container 10.1 has taken place is not necessary, but would reduce the sector available for the container treatment, as described in connection with FIGS. 4 and 5.

FIG. 4 shows a schematic representation of an exemplary profile 280 of the displacement of a holding device 240 and/or a container 10 along the height direction H on a container inner surface treatment device 200. In the region 270, the container 10 is received by the holding device 240 of the container inner surface treatment device 200. As described above, it is first lowered in order to remove it from the internally gripping holding device 140 of the container outer surface treatment device 100. For a short time, the container 10 is thus at a height level which is below the height level at which the first contact with the holding device 240 took place. The abscissa axis is marked with both t and θ. This is to symbolise that the profile can be both time dependent and angle dependent. Since the rotation of the support takes a certain amount of time anyway, the profile will usually be time-dependent and angle-dependent when using a rotating carrier 220.

As soon as the container 10 has been taken over by the holding device 240 and both have moved sufficiently away from the container outer surface treatment device 100 due to the rotation of the rotating carrier 220, the actual treatment process 272 can begin. For this purpose, the container is lifted, i.e. moved along the height direction H. The container is then moved to the highest point. At the highest point, the container inner surface treatment device 250, which is schematically shown as a beam finger 250, is located in sections inside the container. There and on the way there and away from it, it can act upon the inner surfaces of the container with a medium or radiation. As soon as the container has been lowered to such an extent that the container inner surface application device 250 is arranged completely outside this container, the container is delivered in the area 274 to a transport device arranged downstream. This delivery takes place at a different, in particular higher, height level than when the container is picked up in area 270.

The necessary displacement of the holding device 240, which is then not occupied by a container, to the first height level, namely the height level for the container pick-up, takes place in a time interval, or angular range 276, in which no treatment of the container 10 can take place. Thus, this time interval 276, which is usually referred to as "dead time", is no longer unused, but can actively contribute to the preparation for the next treatment step or for the next container pick-up 270. As illustrated in particular by FIGS. 5a and 5b, the time 272 available for the actual treatment process or the container treatment sector 272 can thus be increased. For a given treatment time or the arc length used for this purpose, the circumference of the circle swept by the holding elements can be reduced. This enables a smaller radius and thus smaller dimensions of the rotating carrier 220.

Figure 5B:
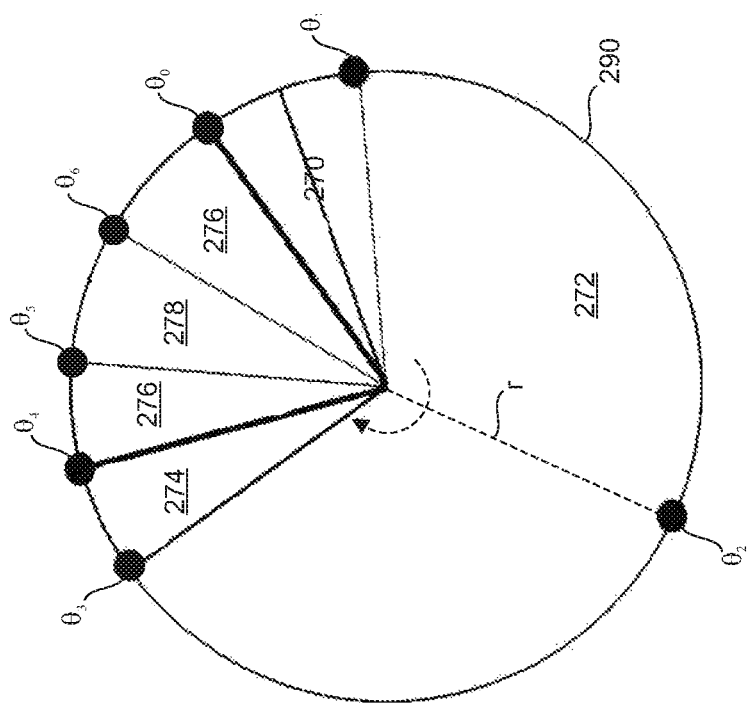
FIG. 5b shows an exemplary assignment of different sectors of a circular path to different process steps in a treatment device according to the preferred embodiment of the present invention.
Figure 5A:
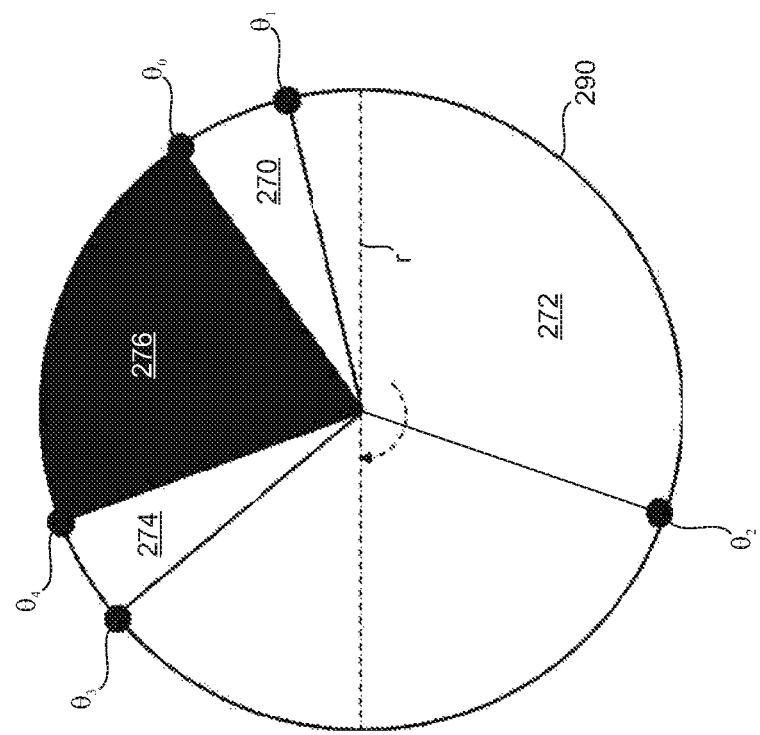
FIG. 5a shows an exemplary assignment of different sectors of a circular path to different process steps in a treatment device according to the state of the art.

FIG. 5a shows an exemplary assignment of different sectors of a circular path to different process steps in a treatment device according to the state of the art. In sector 270, a container is taken over by a holding device. The arc of a circle belonging to this sector must necessarily have a minimum length, since the insertion of the beam finger can only take place when the holding device 140 of the transport device arranged upstream must be completely removed from the range of movement of the holding device 240 and the container 10 picked up by it. Therefore, only after leaving this sector the insertion of the beam finger into the container can begin at the point marked θ1.

The following sector 272 is available for container treatment. During treatment, the container is guided along the arc 290. The point θ2 in this sector marks the turning point from which the beam finger is guided out of the container. The sector 272 extends to the point $θ_3$ at which the beam finger is completely removed from the container. As soon as this is ensured, the treated container 10 can be delivered to a downstream transport device 300 in sector 274.

Since the upstream transport device and also the downstream transport device 300 each occupy a certain space, the sector of the dead volume 276 cannot be reduced at will. Depending on the dimensions of the adjacent transport devices, this sector usually spans a range of about 75°-90°. Thus, the point θ4 is usually about 270°-285° with respect to the point of the beginning of the pick-up of the container $θ_0$. This sector cannot be used for container treatment.

FIG. 5b shows an exemplary assignment of different sectors of a circular path to different process steps in a treatment device according to a preferred embodiment of the present invention. Sectors and process steps analogous to those shown in FIG. 5a are marked with the same reference signs. Accordingly, in a container inner surface treatment device 200 according to the present invention, the transfer of a container 10 takes place in sector 270, starting at point $θ_0$. Since the lowering of the holding device 240 preferably takes place in this sector anyway, in which it is not yet possible to raise the holding device 240 to avoid collisions with the holding device 140 of the transport device 100 arranged upstream, the starting point $θ_1$ of the treatment is similar to the example from the prior art, despite the lowering.

The container treatment takes place in sector 272. The point $θ_2$ also marks the turning point from which the beam finger is guided out of the container. Only direct comparison shows that sector 272 is wider than the sector available for treatment according to FIG. 5a. The greater width of sector 272 can be achieved because the transfer to a subsequent transport device 300 in sector 274 takes place immediately when the holding device has been lowered so far that no section of the beam finger is any longer inside the container 10. The return of the holding element to the height level, which must be present at point $θ_0$, does not occur until sector 278, which is a section of sector 276 that marks the dead time. In the example shown, sector 278 extends over an angle of 25°, namely from $θ_5$=310° to $θ_6$=335° (in each case with respect to $θ_0$).

Since for a given length L of the circular arc 290 (for example, by the rotation speed and the treatment time), the radius r can be reduced according to the formula L=2π·r·θ/360 as the angle θ increases. According to the above formula, increasing the angle by 10° while keeping the arc length L the same allows the radius r to be reduced by almost 20%. Since the radius is even included with $r^2$ in the circular area required for the carrier 220, even small increases in the sector 272 usable for treatment or in the angle between $θ_1$ and $θ_3$ result in a large saving in area and also in material and weight for the container inner surface treatment device 200.

Figure 6:
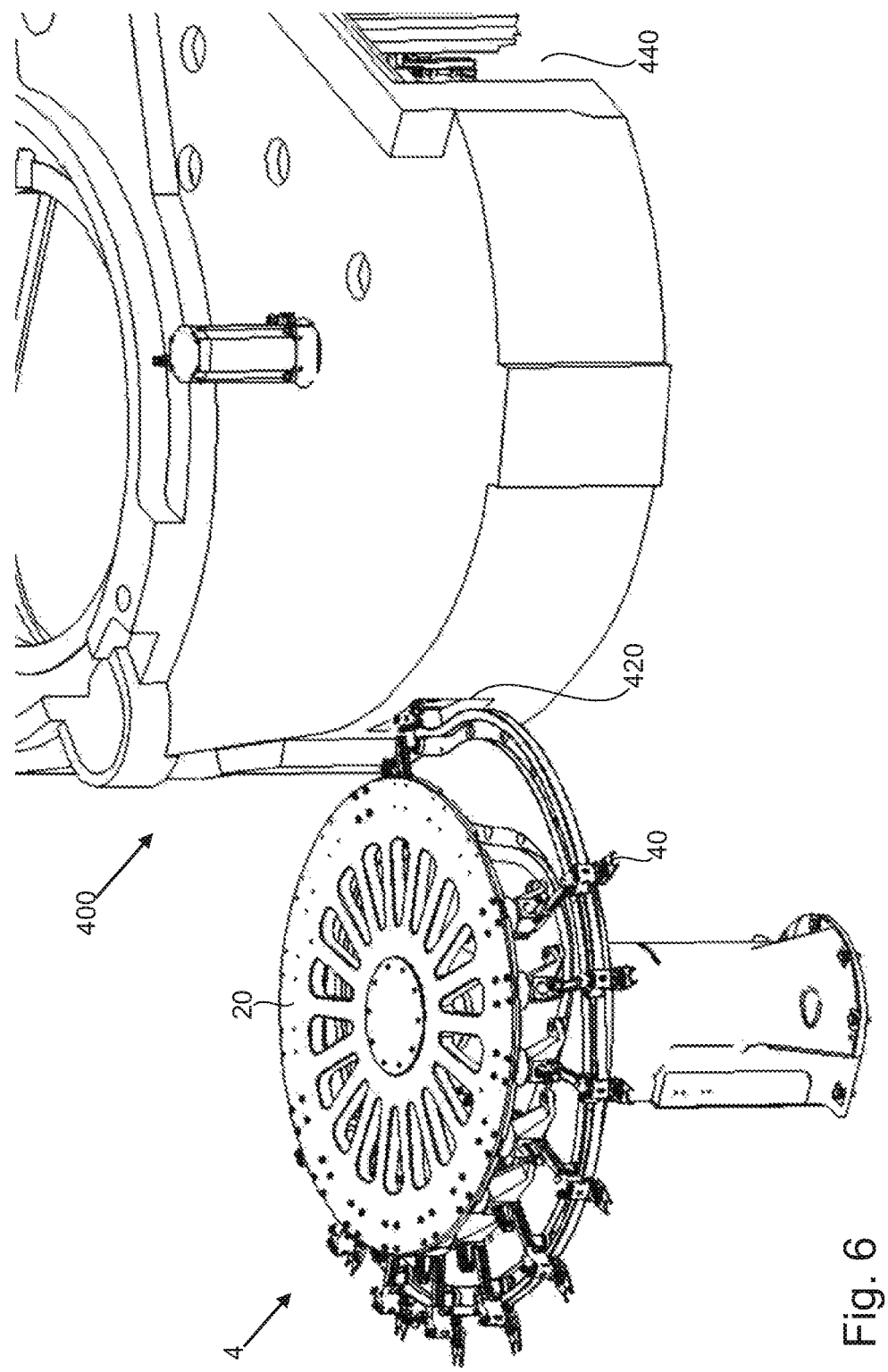
FIG. 6 shows a schematic representation of a transfer from the first transport device to the second transport device.

FIG. 6 shows a schematic representation of a transfer from the first transport device 4 to the second transport device. In this representation, the second transport device is arranged inside the housing 400 and is therefore not visible. The first transport device 4 is a first pitch distribution starwheel, which is designed to change a pitch between adjacently transported plastic containers. This is made possible by the pivotable mounting of the holding elements 40.

The first transport device 4 has a rotatable carrier and transfers the plastic containers via a (transfer) window 420 to the second transport device arranged inside the housing 400. The reference sign 152 indicates the container outer surface application area in which the outer treatment of the plastic containers is carried out.

Figure 7:
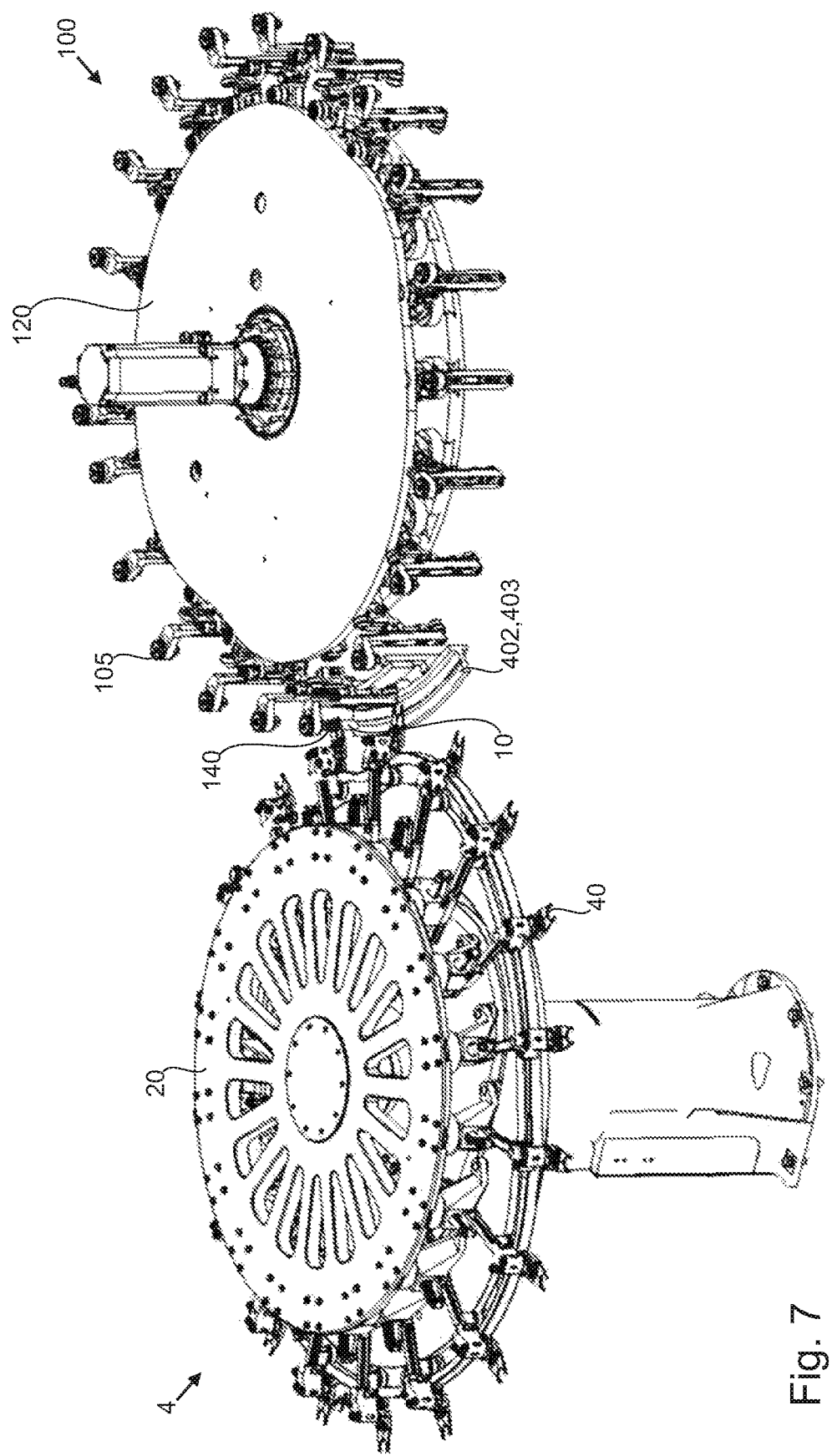
FIG. 7 shows a further schematic representation of a transfer from the first transport device to the second transport device.

FIG. 7 shows a further schematic representation of a transfer from the first transport device 4 to the second transport device 100. For a more precise representation of this transfer, it is shown in FIG. 7 without the housing. In particular, the moment of transfer is shown, during which the plastic container 10 is held both by the holding element 40 of the first transport device 4 and by the holding element 140 of the second transport device 100. The second transport device 100 is a second pitch distribution starwheel, which is also designed to change a division between adjacently transported plastic containers.

The second transport device 100 has a lifting curve 402, 403 at least in the area of the actual transfer, along which a guide roller 406 is guided so that a safe transfer is possible. The reference sign 105 indicates a lifting and rotating device which enables a lifting movement of the holding element 140 towards the plastic container 10 during the transfer, whereby the holding element 140 is inserted into the plastic container 10 in order to hold it. The reference symbol 120 indicates the rotatable carrier of the second transport device 100.

Figure 8:
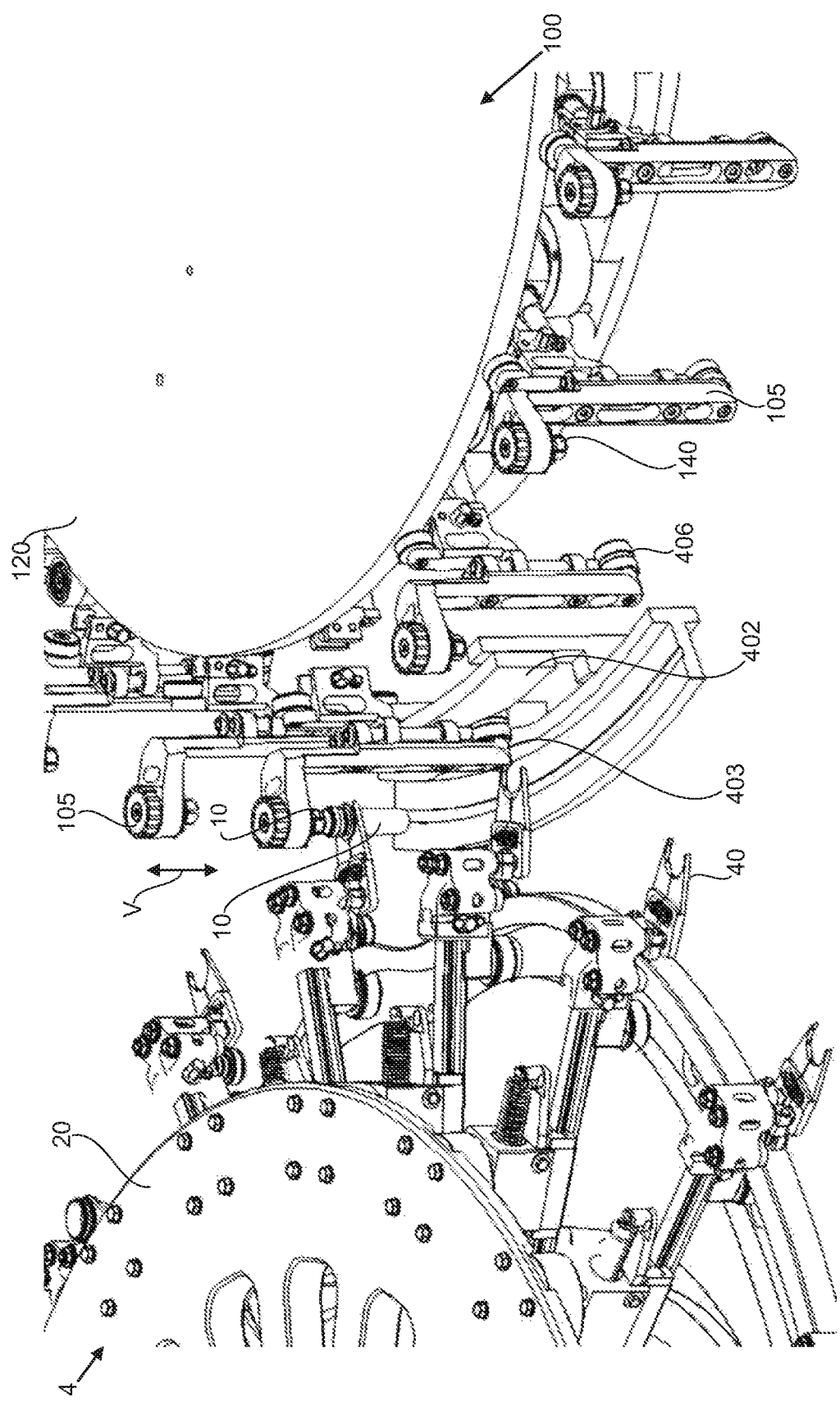
FIG. 8 shows a detailed view of a transfer from the first transport device to the second transport device.

FIG. 8 shows a detailed representation of a transfer from the first transport device 4 to the second transport device 100. As in FIG. 7, the plastic container 10 is held in this representation both by the holding element 40 of the first transport device 4 and by the holding element 140 of the second transport device 100.

The first lifting curve 402 and the second lifting curve 403 between which a guide roller 406 of the lifting and rotating device 105 is guided are clearly visible in this illustration. The lifting and rotating device 105 is suitable and intended for moving the holding element 140 along the vertical direction v in the direction of the container.

Figure 9:
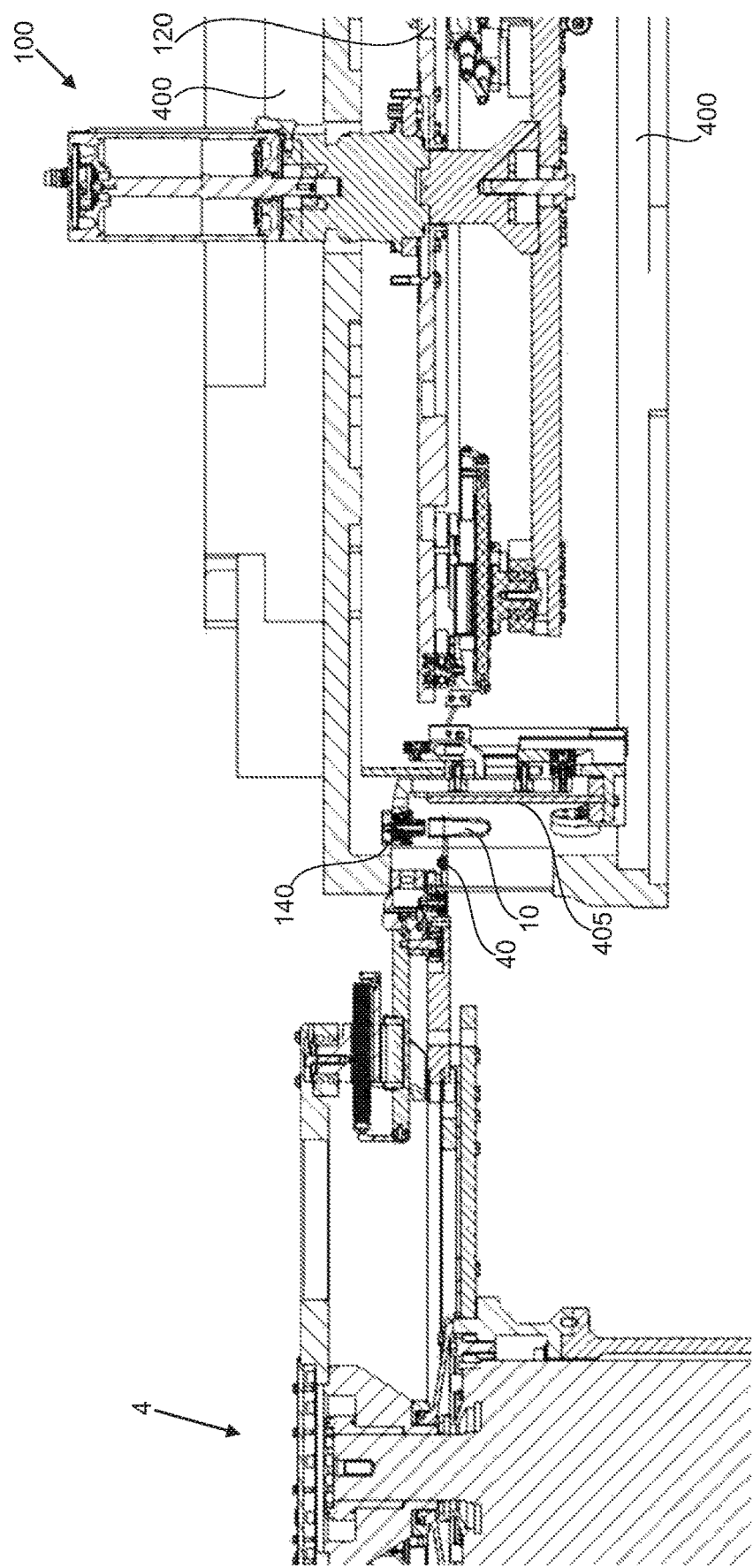
FIG. 9 shows a sectional view of a transfer from the first transport device to the second transport device.

FIG. 9 shows a sectional view of a transfer from the first transport device 4 to the second transport device 100, wherein the time of the transfer shown in FIGS. 7 and 8 is also shown here. The reference sign 405 indicates a shielding device which shields the environment from the interior of the housing 400 so that, for example, radiation and in particular X-rays produced during sterilisation of the containers do not reach the environment.

Figure 10:
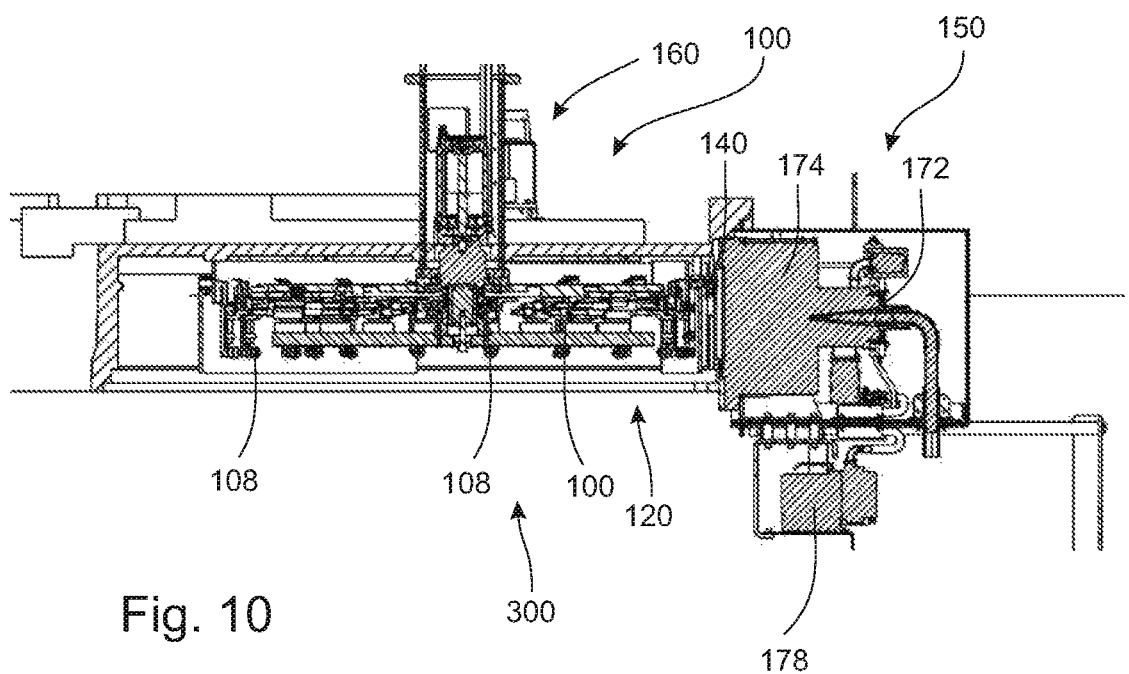
FIG. 10 shows a further illustration of a transport device with an external sterilisation device.

FIG. 10 shows a further embodiment of the device according to the invention. Here again the transport device (inside the housing) is shown with the rotatable carrier 120. To avoid repetition, please refer to the above description of FIG. 3.

The reference sign 150 identifies the container outer surface application device in its entirety. This has an electron generation device 172 which ends in a vacuum chamber 174. The reference sign 178 identifies a vacuum pump, in particular for achieving a rough vacuum. The reference sign 140 indicates a holding device such as a holding mandrel for holding the plastic preforms.

Figure 11:
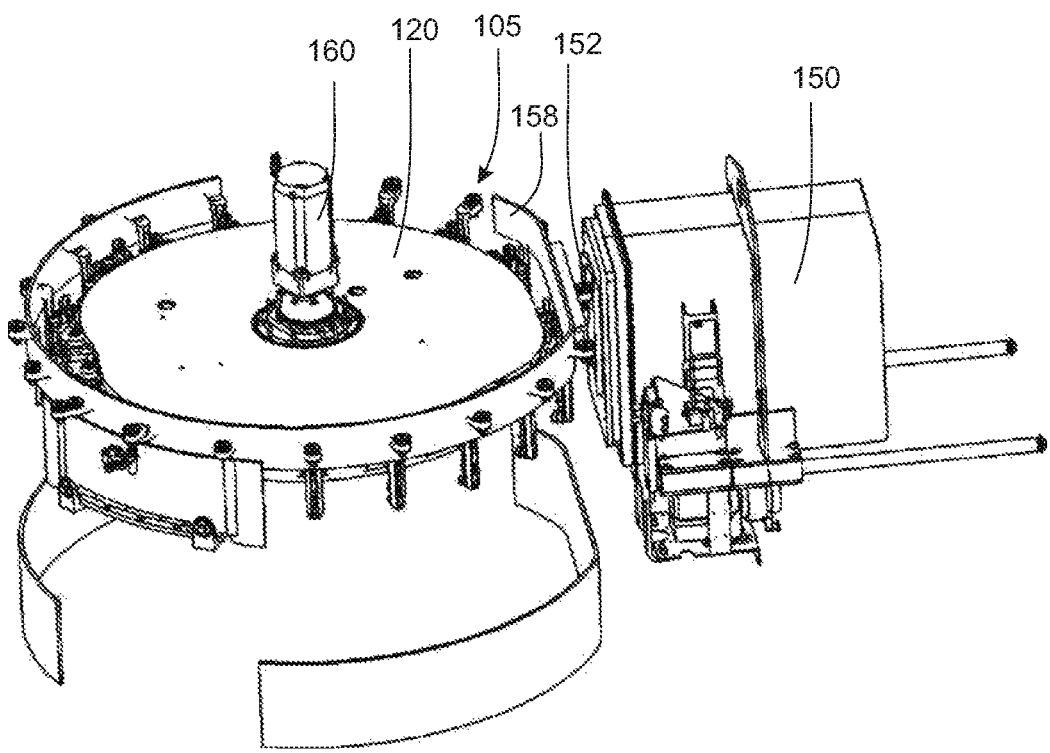
FIG. 11 shows an oblique view of the apparatus shown in FIG. 10.

FIG. 11 shows a further illustration of a preferred embodiment of the invention. Here, the drive device 160 is provided, as well as a wall 158. The reference sign 152 indicates the container outer surface application area, in which the outer sterilisation of the container is carried out. The reference sign 105 again indicates the lifting and rotating device. Reference signs 182 and 183 refer to the upper and lower shields within the (not shown housing). As mentioned above, the upper shield 183 is stationary and the lower shield 182 can be lowered.

Figure 12:
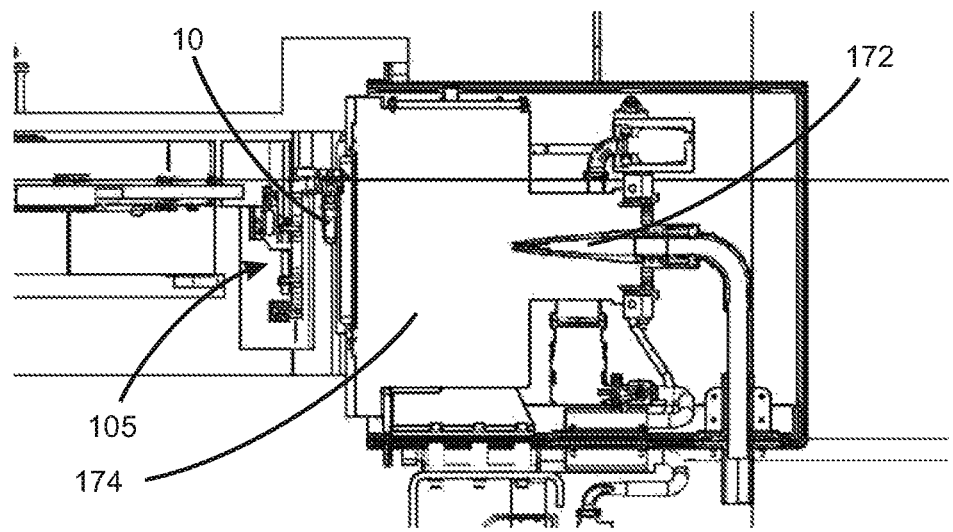
FIG. 12 shows a detailed view of the outer treatment device.

FIG. 12 shows a further illustration of the embodiment shown in FIG. 11. A plastic preform 10 is also shown here, which is held by the lifting and rotating device and sterilised on its outer surface. It can be seen that the plastic preform is moved very close to the outer sterilisation device.

Figure 13:
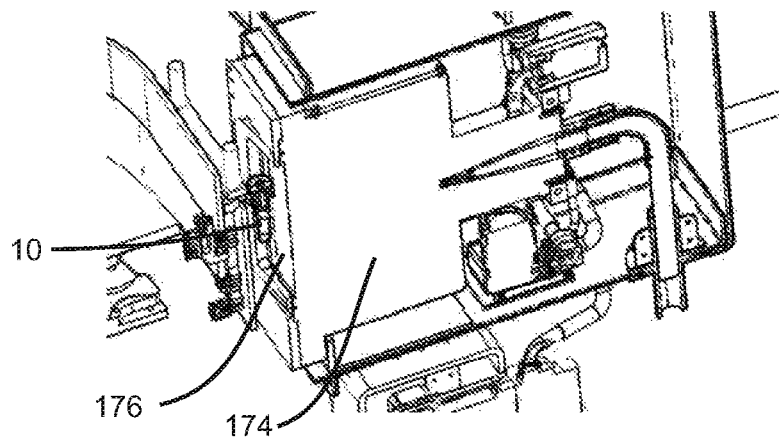
FIG. 13 shows a sectional view of the outer treatment device.

FIG. 13 shows a further sectional view of the embodiment shown in FIG. 12. The reference sign 176 indicates the radiator surface of the surface radiator 150 (i.e. of the outer surface sterilisation device). It can be seen that the entire outer surface sterilisation device is arranged within a housing, wherein the housing is preferably a radiation-shielding housing.

Figure 14:
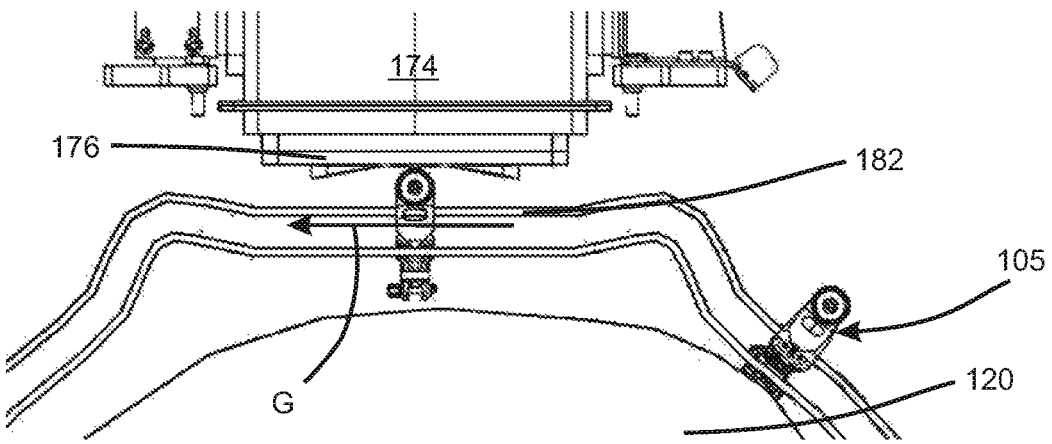
FIG. 14 shows a representation of the transport of the plastic preforms.

FIG. 14 illustrates the outer sterilisation of the plastic preform. An area of shielding 182 is provided which causes the plastic preforms to be transported in a straight line along the line G in the area of the radiator surface in order to improve the sterilisation effect.

Preferably, this part of the shielding is modelled on the track of the plastic preform path, which is not shown. Due to the constrictions on both sides, which are directed towards the surface radiator, an improvement of the radiation shielding can be achieved here.

In addition, it would also be possible for the plastic preforms to be moved more slowly in this section than in other sections of the transport path. At the same time, the plastic preforms are rotated in this section with respect to their longitudinal axes.

Figure 15:
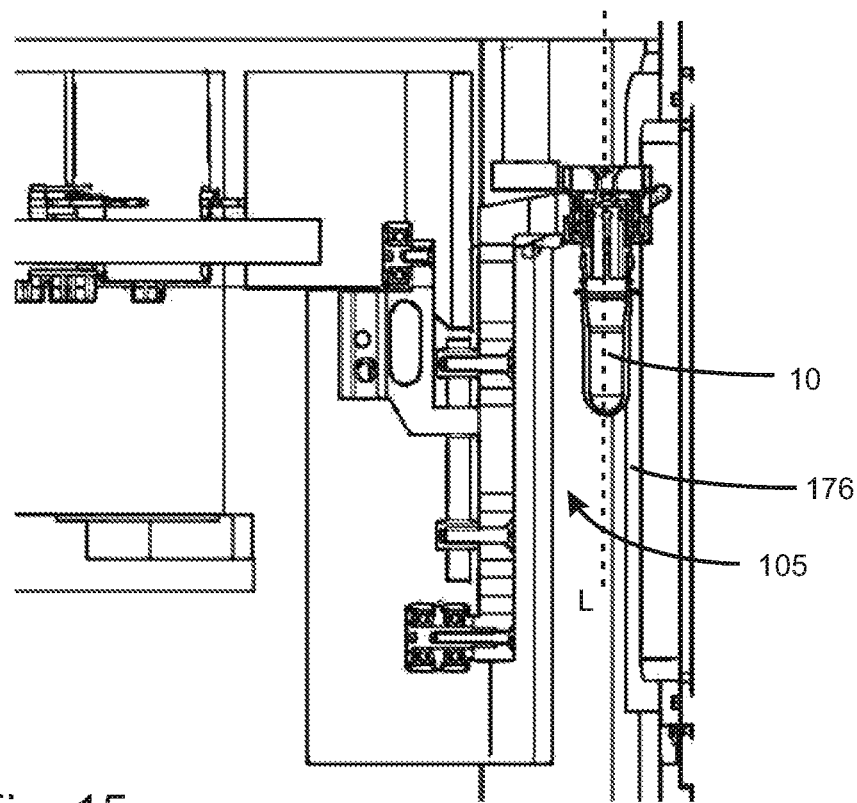
FIG. 15 shows a representation of a lifting and rotating device with a plastic preform.

FIG. 15 shows a detailed illustration of the illustration shown in FIG. 14. Here you can again see the plastic preform which, held by the lifting and rotating device, is moved past the radiator surface. In addition, the plastic preform is also rotatably mounted with respect to its longitudinal direction L or is rotated with respect to this longitudinal direction L.

The arrangement of the upper and lower radiation shields shown in FIG. 11 can also be seen, which are spaced apart so that the lifting and rotating device with the carrier of the rotating unit can pass through them.

Figure 16:
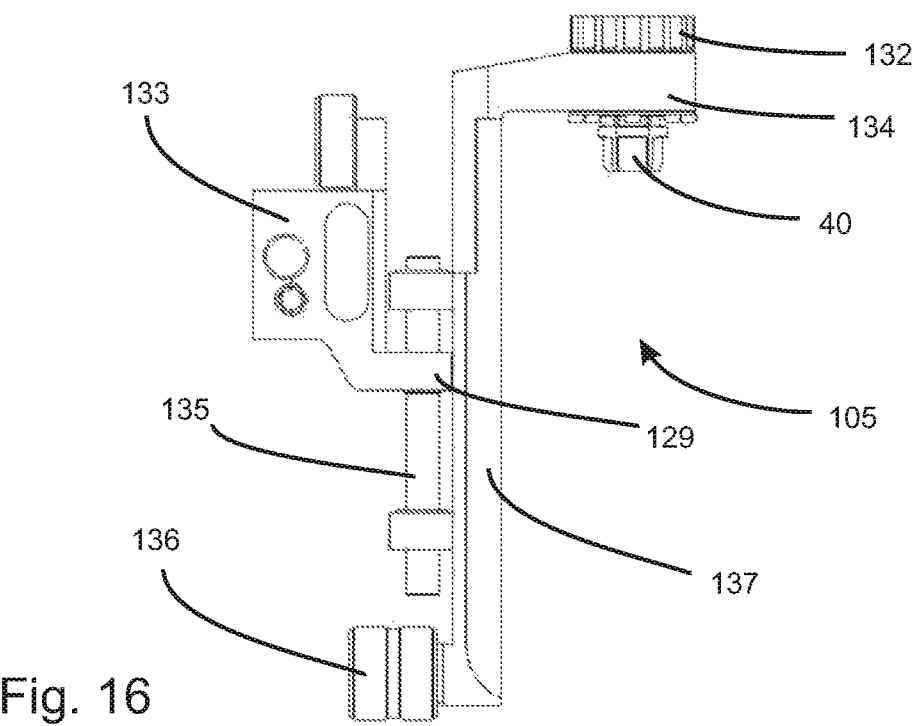
FIG. 16 shows an illustration of the lifting and rotating device.

FIG. 16 shows a more detailed illustration of the lifting and rotating device 105, which comprises a rotor 132 that is non-rotatably coupled to the holding mandrel 30 and is rotatably mounted on the arm or boom 134.

The reference sign 137 indicates a carrier on which the boom 134 is arranged. This carrier 135 is mounted so that it can move linearly in relation to a guide device 135 and is attached to a holder 133. The reference sign 136 indicates a cam roller which, together with a guide cam (not shown), can trigger the linear movement of the holding mandrel.

FIG. 17 illustrates the generation of the rotary movement of the rotor 132 and thus of the plastic preform held thereon. In addition to the rotor 132, a stator 180 is also provided. This stator can be arranged on an inner wall of the housing of the apparatus. The stator here has a plurality of magnets, which are constructed by their magnetic north poles NP and their magnetic south poles SP.

The reference sign 184 shows a stator carrier on which the magnets are arranged. FIG. 17 also shows a problem with the transmission of the torques M. In the situation shown in the left part of the figure, the transmission of torque to the rotor is at a maximum and in the situation shown in the right part of the figure, it is 0. For this reason, there is an uneven transmission of torque and thus, especially at high transport speeds, the plastic preform no longer rotates continuously.

FIGS. 18-20 show an improved design of the stator 180 and the rotor 132. It can be seen here that the magnets NP and SP do not extend parallel to the axis of rotation as in FIG. 17, but in sections at an angle. In the embodiment shown in FIG. 18, the magnets extend in a straight line, but at an angle to the axis of rotation or the longitudinal direction L of the plastic preform, in the embodiment shown in FIG. 19, they take on an overall arrow-like or jagged course, and in the embodiment shown in FIG. 20, they take on an arcuate curved course.

In this way, the magnets are arranged with oblique teeth, which has a smoothing effect on the torque transmission (although the maximum transmitted torque may be lower).

The reference sign Z indicates spaces between the individual magnets SP and NP.

In the embodiment shown in FIG. 21, no magnets are provided either on the stator 180 or on the rotor 132 (here on the stator 180), but a material with a high magnetic permeability, such as iron (Fe). By suitably guiding the magnetic fluxes, the torque fluctuations can be influenced in a favourable manner. This principle is also used in reluctance motors.

Preferably, the material of the magnet carrier, as explained above, is selected so that it has the lowest possible specific electrical resistance.

FIG. 22 shows a further illustration of this. In this embodiment, the carrier 184 of the stator and the carrier 131 of the rotor are each made of this material with low specific resistance.

FIG. 23 illustrates the effect of this design. Whenever the tangential speed is not equal to the ideal rolling speed on the bar, the opposing permanent magnets induce a voltage in the conductive carrier material and cause eddy currents. These brake or accelerate the roller and push it in the direction of the ideal speed.

Basically, the idea corresponds to the principle of the eddy current brake, i.e. here the circumference of the roller is "braked" and thus the roller itself is set in rotation.

For reasons of corrosion protection, the surface may need to be coated.

Figure 24:
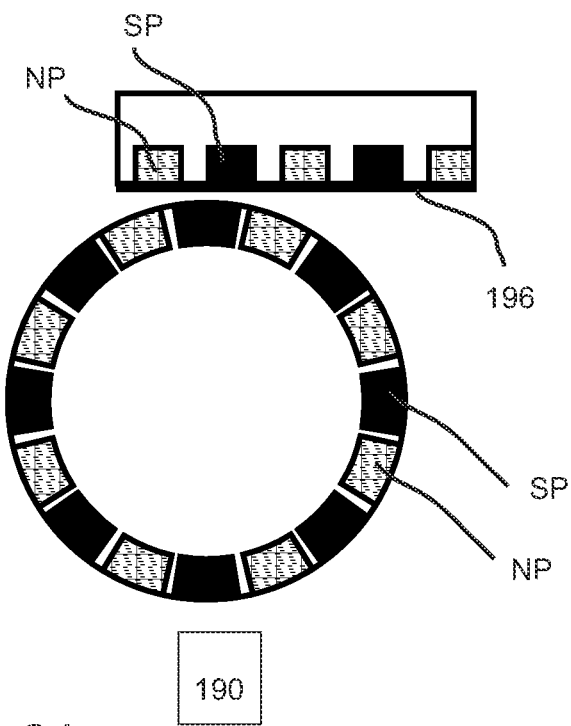
FIG. 24 shows a representation for the magnetic transmission of rotational movements in a fifth embodiment.

FIG. 24 illustrates an embodiment in which the magnets are covered with a cover 196, for example a plate-like body made of aluminium.

The reference sign 190 roughly schematically indicates a monitoring device that monitors the transmission of the rotary movement to the rotor 132. This can be, for example, a camera that is aligned with the rotor. In addition, other non-contact sensors could also be used to monitor the rotary motion. One problem here is that the rotors themselves move along the transport path of the plastic preforms.

Figure 25:
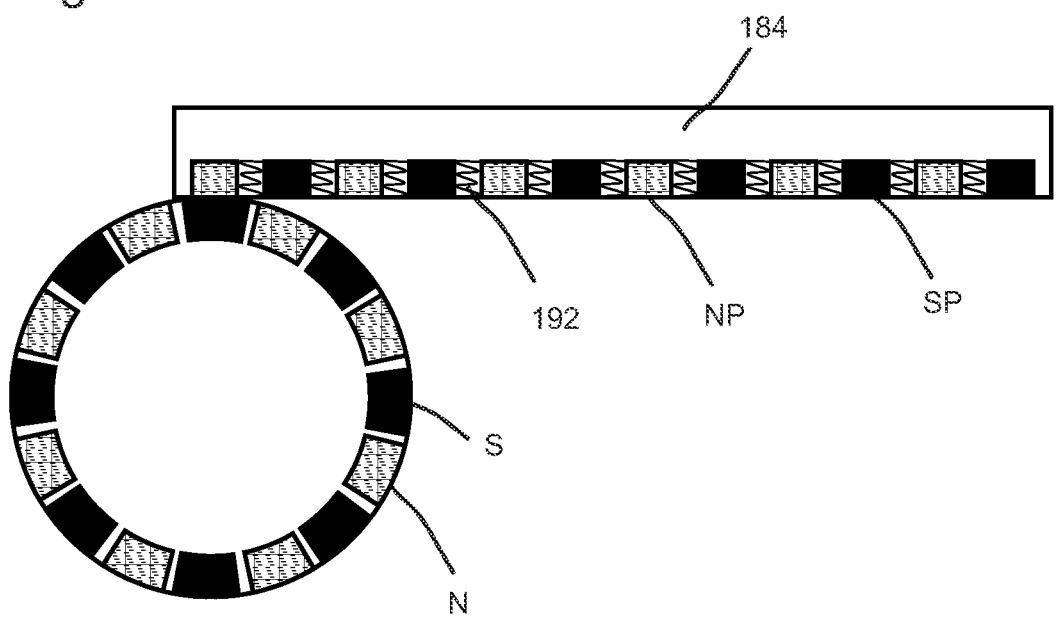
FIG. 25 shows an illustration for the magnetic transmission of rotational movements in a sixth embodiment.

FIG. 25 shows a further advantageous design which enables monitoring of the transmitted torques or the rotary movement of the rotor. In this design, as mentioned above, coils 192 are arranged between the magnets NP and SP, which here point axially in the direction of the roller. As long as the roller or rotor 132 rotates at the ideal speed and "rolls" along the bar or stator as desired, only a little voltage is induced in the coils. However, if the roller slips or oscillates at its rotational speed, then relatively much voltage is induced in the coils due to the large change in flux density.

Figure 26:
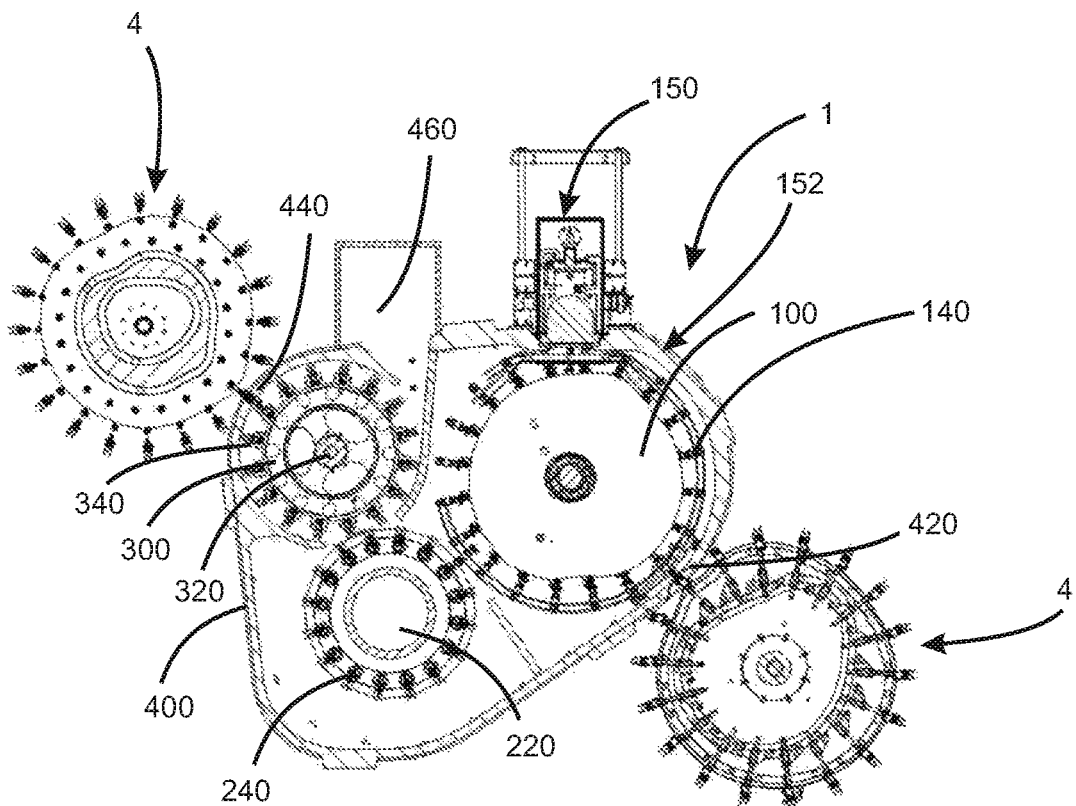
FIG. 26 shows a representation of an advantageous apparatus with a airlock device.

FIG. 26 shows an advantageous apparatus 1 for treating containers, in particular plastic preforms 10. In this case, the plastic preforms 10 are transferred via a transport device 4, which is located outside the housing 400 of the apparatus 1, through an inlet or the window 420 or onto a transport device 100, in particular a transport starwheel.

This transport device 100 is located on a rotatable carrier (or has such a carrier) and conveys the plastic preforms through or to a container application device 150 for acting upon the outer surfaces. The preforms are then transferred to a further transport device 200, in particular a transport starwheel, which is located on a rotatable carrier 220 or has such a carrier.

A container application device, in particular a plurality of beam fingers for acting upon the inner area of the plastic preforms 10, is arranged on this transport device.

Finished plastic preforms 10 are transferred via a transport device 300, in particular a transport starwheel through an outlet 440 to a further transport device 4, which is arranged outside the housing.

The reference sign 152 indicates a container application area. The plastic preforms 10 are conveyed on a transport device 100 in this area and are acted upon there by a container application device 150. The outer surfaces of the plastic preforms 10 are acted upon.

The reference signs 140, 240 and 340 indicate holding elements, in particular holding mandrels for holding the plastic preforms 10. These are designed to enable a transition between the transport devices.

The reference sign 460 indicates an airlock device which removes defective plastic preforms 10 or plastic preforms 10 which cannot meet certain requirements from the apparatus 1 via the transport device 300.

Figure 27:
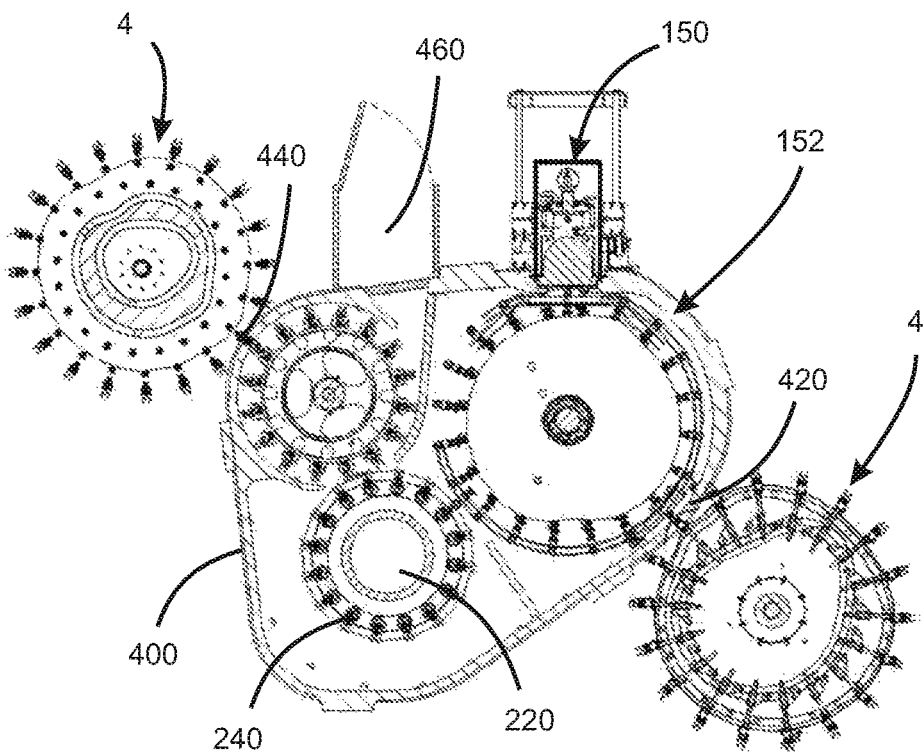
FIG. 27 shows a further illustration of an advantageous apparatus with an airlock device.

FIG. 27 shows an apparatus 1 according to the invention with a airlock device 460, which is in an open state.

Figure 28:
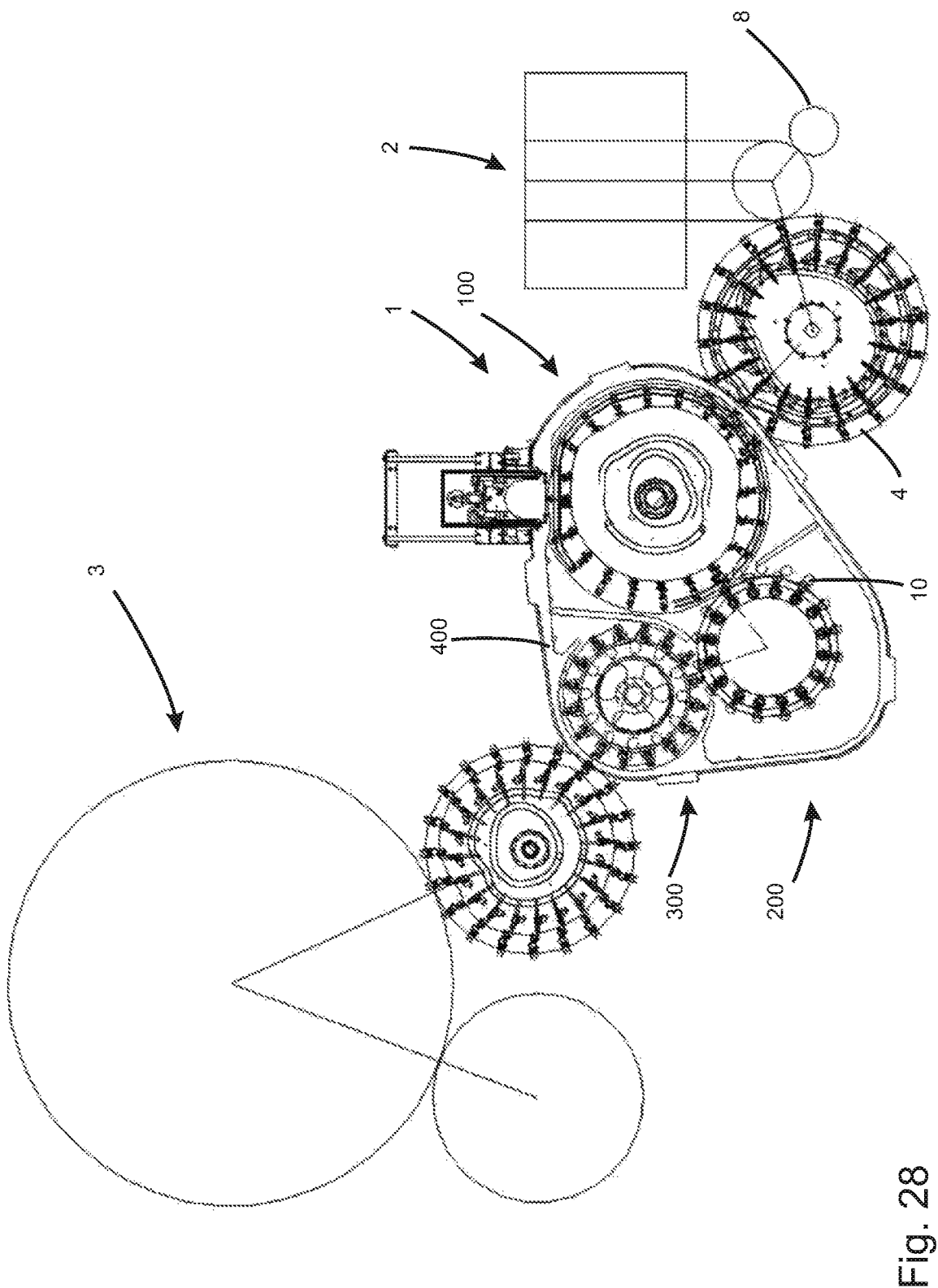
FIG. 28 shows a representation of an advantageous apparatus with a rinser.

FIG. 28 also shows a schematic view of a container treatment apparatus 1 in an exemplary embodiment. In particular, the transport devices 100, 200, 300 for transporting a container 10 along a transport path within a housing 400, which is not highlighted in this illustration, can be seen. Also in FIG. 13, the transport device 100 is a container outer surface treatment device 100 and the transport device 200 is a container inner surface treatment device 200.

Also visible in FIG. 28 are the heating apparatus 2 and the further transport device 4, which is arranged between the heating apparatus 2 and the container outer surface treatment device 100 and outside the housing 400. Immediately in front of the heating apparatus 2 is an application device 8 which can act upon a container with a flowable medium.

The reference sign 3 indicates a forming device, in particular a blow-moulding machine for forming plastic preforms into plastic containers. It can be seen that the heating apparatus 2 is arranged at a different angle to the forming device 3 than is the case, for example, in FIG. 1. Whereas in FIG. 1 the heating apparatus 2 and the forming device 3 are arranged essentially at a 90° angle to each other, in FIG. 28 they are arranged at a 0° angle to each other. This is particularly advantageous if an application device 8 is integrated in the heating apparatus 2.

Figure 29:
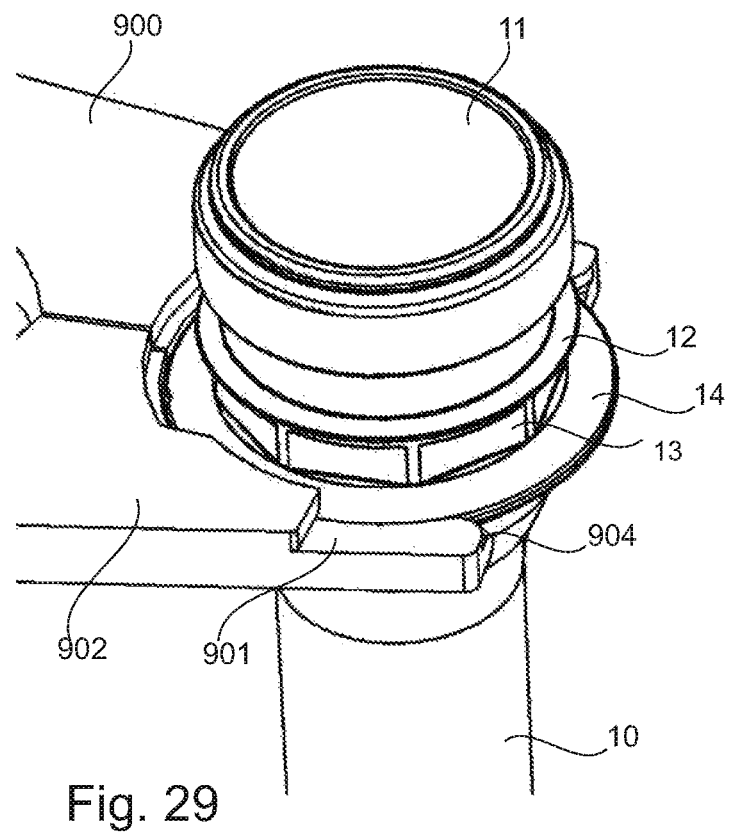
FIG. 29 shows a representation of a holding device for holding plastic preforms.

FIG. 29 shows a container 10, in particular a plastic preform, whose head area comprises a mouth 11, a closure ring 12, a mouth groove 13 and a support ring 14.

The container 10 is held by a first holding device 900, which is designed as a two-part clamp. The first holding device 900 has a holding groove 903 which contacts the outer surface of the support ring 14. The first holding device 900 is configured such that the underside of the support ring 14 is contacted in the entire area of the first holding device 900. In addition, the first holding device 900 has an area 902 which contacts the upper side of the support ring 14.

Overall, therefore, the support ring 14 of the container 10 is clamped both laterally and from above and below by the first holding device 900 and is thereby fixed and secured against unintentional lateral tilting.

It can also be clearly seen that the end of the first holding device 900 facing the container 10 or the two ends of the individual clamps have a tapered area 901. A more detailed description of the tapered area is given in connection with the description of FIG. 2.

Figure 30:
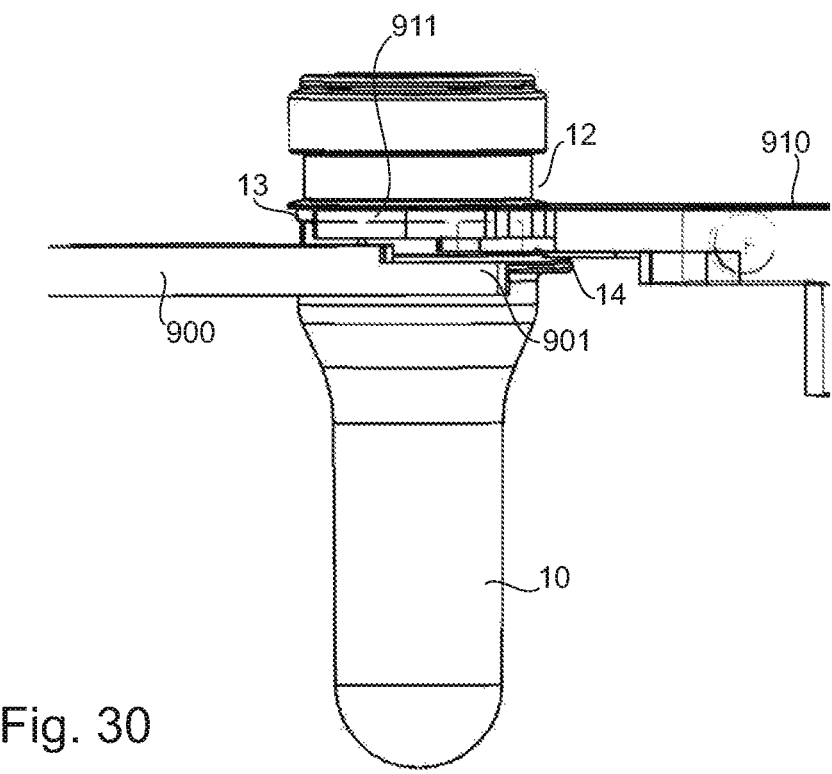
FIG. 30 shows a further illustration of a holding device for holding plastic preforms.

FIG. 30 shows a holding arrangement with a container 10 on which a first holding device 900 and a second holding device 910 are arranged, for example at the time of transfer between a first and a second transport device.

It can be seen, analogous to FIG. 29, that the first holding device 900 engages the support ring 14 of the container 10 and the tapered portion 901 of the first holding device 900 points in the direction of the second holding device 910. The second holding device 910 engages in the mouthpiece groove 13 of the container 10, wherein the second holding device 910 resting against the underside of the closure ring 12.

The second holding device 910 also shows a tapered area 911, which points in the direction of the first holding device 900. Furthermore, it can be seen that the tapered areas 901 and 911 are complementary to each other. This ensures that the two holding devices 900 and 910 do not touch each other.

The applicant reserves the right to claim all features disclosed in the application documents as essential to the invention, provided they are individually or in combination new compared to the prior art. Furthermore, it is pointed out that the individual figures also describe features which may be advantageous in themselves. The skilled person immediately recognizes that a certain feature described in a figure can also be advantageous without adopting further features from this figure. Furthermore, the skilled person recognizes that advantages can also result from a combination of several features shown in individual figures or in different figures.

LIST OF REFERENCE SIGNS 1 container treatment apparatus
2 heating apparatus
3 container forming device
4 transport device, transport starwheel (outside the housing)
5 heating device
6 drive device of the transport device or transport starwheel 4
10 container, preform
11 mouth of the plastic preform
12 closure ring
13 mouth groove
14 support ring
20 rotatable carrier
40 holding element, mandrel
100 container outer surface treatment device, transport device
105 lifting and rotating device
110 displacement device, displacement mechanism
120 rotatable carrier
131 rotor support
132 rotor of the lifting and rotating device
133 guide device
134 boomer
135 guide device
136 cam roller
137 carrier
140 holding element, holding device, mandrel
150 container outer surface application device, radiation source
152 container outer surface application area
158 wall
160 drive device (of the rotatable carrier of the container outer surface treatment device)
172 high voltage cable with plug
174 vacuum chamber
176 radiation surface of the surface radiator
178 vacuum pump
180 stator
182 lower shielding
183 upper shielding
184 stator carrier
190 monitoring device
192 coils
196 shielding
200 container inner surface treatment device, transport device
220 rotatable carrier
240 holding element, holding device, clamp
250 container inner surface application device, beam finger
252 radiation generating device
260 drive device (of the rotatable carrier of the container inner surface treatment device)
270 container receiving area, container transfer area, sector
272 container treatment area, sector
274 container delivery area, container transfer area, sector
276 dead time
278 area/sector of displacement of the unoccupied holding device
280 profile, height profile
290 (available for internal container treatment) circular arc
300 transport device, transport starwheel (inside the housing)
320 rotatable carrier
340 holding element, holding device, clamp, mandrel
400 housing
402 first lifting curve
403 second lifting curve
405 shielding device 406 guiding role
410 space inside the housing, housing interior, cleanroom
412 space outside the housing, environment
420 window (for introducing into the interior of the housing)
440 window (for discharging from inside the housing)
460 airlock
900 holding device
901 tapered area
902 area
904 holding groove
910 holding device
911 tapered area
v vertical direction
T transport path
L longitudinal direction of the plastic preform
K circuit
t time
S sector
G straight line direction of movement
H height direction
Θ angle
$_1Θ$-$Θ_8$ point on circle (-arc)
R radius
M torque
NP (magnetic) north pole
SP (magnetic) south pole
Z gaps between magnets

The invention claimed is:

1. A container treatment apparatus, having several transport devices configured for transporting a container along a predetermined transport path, wherein at least one of the transport devices has at least one holding device configured for holding at least one container during container treatment and/or transport along the transport path,
wherein
the transport device has a rotatable carrier and a plurality of holding elements arranged on this carrier, wherein at least one of these holding elements in a first sector, in which a container is received, has a height with respect to a vertical projection of the transport path which is different from that in a second sector, in which a container is dispensed from the rotatable carrier, and wherein a third sector, in which an at least partial compensation of the height difference of the holding elements takes place, is located along a direction of rotation of the carrier after the second sector and before the first sector, and wherein at least one of the holding elements in a fourth sector, which lies along the transport path between the first and second sector, is arranged, at least in sections with respect to the vertical projection of the transport path, at a greater height than in the first sector and than in the second sector.

2. The container treatment apparatus according to claim 1, wherein
a housing within which the transport path extends at least in sections and wherein at least one of the transport devices is a container outer surface treatment device and at least one of the transport devices is a container inner surface treatment device.

3. The container treatment apparatus according to claim 2, wherein
the container outer surface treatment device and the container inner surface treatment device are arranged in direct succession along the transport path.

4. The container treatment apparatus according to claim 3, wherein
the container outer surface treatment device and the container inner surface treatment device are arranged in direct succession along the transport path, wherein the container outer surface treatment device and the container inner surface treatment device are configured for a transfer of a container from the container outer surface treatment device to the container inner surface treatment device.

5. The container treatment apparatus according to claim 1, wherein
at least one of the holding elements, has a lower height in the first sector with respect to the vertical projection of the transport path than in the second sector.

6. The container treatment apparatus according to claim 1, wherein
in a fourth sector, a container treatment device is arranged at least in sections in-side a container, wherein the container treatment device having a constant height with respect to the vertical projection of the transport path.

7. A method for the treatment of containers, wherein the containers are transported along a predetermined transport path, wherein the containers are each held by at least one holding device during the transport and/or the container treatment,
wherein
the containers are guided at least in sections by at least one of the holding devices of a transport device on a section of the transport path whose vertical projection comprises a section of a circular path, wherein a container is received in a first sector by a holding element at a first height with respect to the vertical projection of the transport path and is dispensed in a second sector from the rotatable carrier at a second height different from the first height, wherein an at least partial compensation of the height difference of the holding elements takes place in a third sector which lies along a direction of rotation of the carrier after the second sector and before the first sector, wherein at least one of the holding elements in a fourth sector, which lies along the transport path between the first and second sector, is arranged, at least in sections with respect to the vertical projection of the transport path, at a greater height than in the first sector and than in the second sector.

8. The method according to claim 7,
wherein
the transport path extends at least in sections through a housing and wherein the containers are transported at least in sections through a container outer surface treatment device and a container inner surface treatment device.

9. The method according to claim 7,
wherein
the container is delivered in the second sector at a second height which is greater than the first height at which the container is received in the first sector.

10. The method according to claim 7,
wherein
the container in the fourth sector, which is arranged on the transport path between the first and the second sector, is acted upon by a container treatment device with a treatment agent.

11. The method according to claim 8, wherein the holding device of the container outer surface treatment device and/or the container inner surface treatment device in one section receives the container from a container outer surface treatment device or container inner surface treatment device in another section.

\* \* \* \* \*